(12) United States Patent
Wagner

(10) Patent No.: US 12,397,040 B2
(45) Date of Patent: Aug. 26, 2025

(54) METHODS FOR TREATING AND REDUCING TRAUMATIC BRAIN INJURY-ASSOCIATED IMPAIRMENTS USING SGP130

(71) Applicant: UNIVERSITY OF PITTSBURGH—OF THE COMMONWEALTH SYSTEM OF HIGHER EDUCATION, Pittsburgh, PA (US)

(72) Inventor: Amy Kathleen Wagner, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 1044 days.

(21) Appl. No.: 17/135,946

(22) Filed: Dec. 28, 2020

(65) Prior Publication Data
US 2021/0220439 A1 Jul. 22, 2021

Related U.S. Application Data

(63) Continuation of application No. PCT/US2019/039912, filed on Jun. 28, 2019.
(Continued)

(51) Int. Cl.
*A61K 38/17* (2006.01)
*A61K 47/68* (2017.01)
(Continued)

(52) U.S. Cl.
CPC ...... *A61K 38/1793* (2013.01); *A61K 47/6811* (2017.08); *A61P 25/28* (2018.01);
(Continued)

(58) Field of Classification Search
None
See application file for complete search history.

(56) References Cited

U.S. PATENT DOCUMENTS 9,034,817 B2 * 5/2015 Watzig .................. A61P 37/08
514/18.7
2002/0009444 A1 1/2002 Grillo-Lopez
(Continued)

OTHER PUBLICATIONS

Kumar et al., Brain Behav Immun. Mar. 2016; 53: 183-193 (Year: 2016).*

(Continued)

*Primary Examiner* — Karl J Puttlitz
(74) *Attorney, Agent, or Firm* — Baker Botts L.L.P

(57) ABSTRACT

The present disclosure relates to methods and compositions for treating traumatic brain injury (TBI) and TBI-associated impairments and improving outcome in subjects that have sustained traumatic brain injury comprising administering to the subject a sgp130 or an agent that promotes the binding of sgp130 and sIL-6R and/or reduces sIL-6R mediated trans-signaling. The present disclosure also relates to methods and kits for identifying a subject that is at risk of developing a TBI-associated impairment (e.g., headache, depression, cognitive deficits, and seizure) or monitoring the responsiveness to a treatment regimen for a TBI-associated impairment in the subject, using biomarkers (e.g., white blood cells indices (e.g., Neutrophil-Lymphocyte Ratio (NLR), absolute lymphocyte counts), sIL-6R, sgp130, IL-6, sgp130:sIL-6R ratio, sIL-2Ra, IL-2, sIL-2Ra:IL-2 ratio, TNFα, TNFRI, and TNFRI:TNFα ratio).

5 Claims, 56 Drawing Sheets

Related U.S. Application Data

(60) Provisional application No. 62/692,405, filed on Jun. 29, 2018.

(51) Int. Cl.
    *A61P 25/28*         (2006.01)
    *G01N 33/68*        (2006.01)

(52) U.S. Cl.
    CPC . *G01N 33/6896* (2013.01); *G01N 2333/5412* (2013.01); *G01N 2333/7155* (2013.01); *G01N 2800/52* (2013.01)

(56) References Cited

U.S. PATENT DOCUMENTS

| | | |
|---|---|---|
| 2005/0130230 A1 | 6/2005 | Davalos et al. |
| 2005/0220761 A1 | 10/2005 | Haggiag et al. |
| 2015/0197567 A1 | 7/2015 | Garcia-Martinez et al. |
| 2017/0291950 A1 | 10/2017 | Fakhroo et al. |

OTHER PUBLICATIONS

Woiciechowsky et al., The Journal of Trauma: Injury, Infection, and Critical Care 52(2): p. 339-345, Feb. 2002 (Year: 2002).*
Jostock et al., Eur. J. Biochem.268, 160-167 (2001) (Year: 2001).*
Matsumoto et al., J Immunol (2010) 184 (3): 1543-1551 (Year: 2010).*
Postoll, Melissa (2018) Longitudinal characterization of headache after TBI and potential immunological target. Master Essay, University of Pittsburgh, downloaded Jun. 19, 2024 from https://d-scholarship.pitt.edu/35769/ (Year: 2018).*
Ruff et al., F1000Res. Aug. 31, 2016;5:F1000 Faculty Rev-2116 (Year: 2016).*
Sung et al., SHOCK, vol. 40, No. 6, pp. 471Y475, 2013 (Year: 2013).*
Ranganathan et al., A06-11, SGP130 Moderates the Relationship Between Chronic IL-6/SIL-6R Complex in Differentiating Outcome After Severe TBI, downloaded Oct. 30, 2024 from https://core.ac.uk/download/pdf/216270798.pdf (Year: 2017).*
Abelson et al., "HPA axis activity in patients with panic disorder: review and synthesis of four studies," Depress Anxiety, 24(1):66-76 (2007).
Allocca et al., "Anti-IL-6 treatment for inflammatory bowel diseases: next cytokine, next target," Curr. Drug Targets 14, 1508-1521 (2013).
Atreya, et al., "Blockade of interleukin 6 trans signaling suppresses T-cell resistance against apoptosis in chronic intestinal inflammation: Evidence in Crohn disease and experimental colitis in vivo," Nat. Med., 6, 583-588 (2000).
Baker et al., "Plasma and cerebrospinal fluid interleukin-6 concentrations in posttraumatic stress disorder," Neuroimmunomodulation. 9(4):209-217 (2001).
Baran et al., "The balance of interleukin (IL)-6, IL-6-soluble IL-β receptor (sIL-6R), and IL-6-sIL-6R-sgp130 complexes allows simultaneous classic and trans-signaling," Journal of Biological Chemistry. May 4, 2018, Epub Mar. 20, 2018, vol. 293, No. 18; pp. 6762-6775; p. 6763, 1st column, 2nd paragraph; p. 6769, 2nd column, 2nd paragraph; DOI:10.1074/jbc.RA117.001163.
Barton et al., "Protective role of interleukin 6 in the lipopolysaccharide-galactosamine septic shock model," Infect Immun, 61(4):1496-1499 (1993).
Beeton et al., "Circulating levels of interleukin-6 and its soluble receptor in patients with head injury and fracture," The Journal of Bone & Joint Surgery, vol. 86. No. 6; pp. 912-917 (2004) DOI: 10.1302/0301-620X.8666.14176.
Bell et al., "Interleukin-6 and interleukin-10 in cerebrospinal fluid after severe traumatic brain injury in children," Journal of Neurotrauma, 14(7):451-457 (1997).
Bigal et al., "Chronic migraine in the population: Burden, diagnosis, and satisfaction with treatment," Neurology, 71(8):559-566 (2008).

Bomyea et al., "Neuropsychiatric Predictors of Post-Injury Headache After Mild-Moderate Traumatic Brain Injury in Veterans," Headache: The Journal of Head and Face Pain, 56(4):699-710 (2016).
Burton et al., "Inhibition of interleukin-6 trans-signaling in the brain facilitates recovery from lipopolysaccharide-induced sickness behavior," J Neuroinflammation. 2011;8:54 (2011).
Calabrese et al., "IL-6 biology: implications for clinical targeting in rheumatic disease," Nat. Rev. Rheumatol. 10, 720-727 (2014).
Campbell et al., "Trans-signaling is a dominant mechanism for the pathogenic actions of interleukin-6 in the brain," J. Neurosci, 34, 2503-2513 (2014).
Caplan et al., "Do Microglia Play a Role in Sex Differences in TBI?," Journal of Neuroscience Research, 95:509-517 (2017).
Carlozzi et al., "Traumatic Brain Injury Patient-Reported Outcome Measure: Identification of Health-Related Quality-of-Life Issues Relevant to Individuals With Traumatic Brain Injury," Arch Phys Med Rehabil, 92(10 Suppl):S52-S60 (2011).
Chalaris et al., "The soluble Interleukin 6 receptor: generation and role in inflammation and cancer," Eur. J. Cell Biol., 90, 484-494 (2011).
Codispoti et al., "Efficacy of nonprescription doses of ibuprofen for treating migraine headache. A randomized controlled trial," Headache, 41(7):665-679 (2001).
Corrigan et al., "Neurogenic inflammation after traumatic brain injury and its potentiation of classical inflammation," Journal of Neuroinflammation. 2016;13:264 (2016).
Daban et al., "Hypothalamic-pituitary-adrenal Axis and Bipolar Disorder," Psychiatr Clin North Am, 28(2):469-480 (2005).
Dichgans et al., "Mutation in the neuronal voltage-gated sodium channel SCN1A in familial hemiplegic migraine," The Lancet, 366(9483):371-377 (2005).
Donders et al., "Clinical Utility of the Patient Health Questionnaire-9 in the Assessment of Major Depression after Broad Spectrum Traumatic Brain Injury," Arch Phys Med Rehabil., 98(12):2514-2519 (2017).
Empl et al., "Soluble Interleukin-2 Receptors Increase During the Active Periods in Cluster Headache," Headache: The Journal of Head and Face Pain, 43(1):63-68 (2003).
Eugster et al., "IL-6-deficient mice resist myelin oligodendrocyte glycoprotein-induced autoimmune encephalomyelitis," European Journal of Immunology. 1998;28(7):2178-2187).
Failla et al., "Variation in the BDNF gene interacts with age to predict mortality in a prospective, longitudinal cohort with severe TBI," Neurorehabilitation and Neural Repair, 29(3):234-246 (2015).
Fann et al., "Validity of the Patient Health Questionnaire-9 in assessing depression following traumatic brain injury," J Head Trauma Rehabil, 20(6):501-511 (2005).
Finkel et al., "Which matters more? A retrospective cohort study of headache characteristics and diagnosis type in soldiers with mTBI/concussion," Headache: The Journal of Head and Face Pain, 57(5):719-728 (2017).
Garbers et al., "Inhibition of classic signaling is a novel function of soluble glycoprotein 130 (sgp130), which is controlled by the ratio of interleukin 6 and soluble interleukin 6 receptor," J Biol Chem, 286(50): 42959-42970 (2011).
Gorst-Rasmussen, "tt: Treelet transform with Stata," Stata Journal, 12(1):130-146 (2012).
Gorst-Rasmussen et al., "Exploring Dietary Patterns By Using the Treelet Transform," Am J Epidemiol., 173(10):1097-1104 (2011).
Halker et al., "Chronic daily headache: an evidence-based and systematic approach to a challenging problem," Neurology, 76(Issue 7, Supplement 2):S37-S43 (2011).
Hays et al., "Item Response Theory Analyses of Physical Functioning Items in the Medical Outcomes Study," Med Care, 45: S32-S38 (2007).
Headache Classification Committee of the International Headache Society (IHS), Cephalalgia 2018, vol. 38(1) 64-73 (2018).
Hoffman et al., "Natural History of Headache a er Traumatic Brain Injury," J Neurotrauma., 28(9):1719-1725 (2011).
Hoge et al., "IL-6 controls the innate immune response against Listeria monocytogenes via classical IL-6 signaling," J Immunol, 190:703-711 (2013).

(56) References Cited

OTHER PUBLICATIONS

Hoh et al., "BCL2 Genotypes: Functional and Neurobehavioral Outcomes after Severe Traumatic Brain Injury," Journal of Neurotrauma, 27(8):1413-1427 (2010).
Hong et al., "The course of headache in patients with moderate-to-severe headache due to mild traumatic brain injury: a retrospective cross-sectional study," J Headache Pain, 18(1) (2017).
Hong et al., "Recombinant soluble gp130 protein reduces DEN-induced primary hepatocellular carcinoma in mice," Sci Rep. 6, 24397 (2016).
Hu et al., "Is Age Associated With the Severity of Post-Mild Traumatic Brain Injury Symptoms?" Canadian Journal of Neurological Sciences, 44(4):384-390 (2017).
Hunter et al., "IL-6 as a keystone cytokine in health and disease," Nature Immunology, 16(5):448-457 (2015).
International Search Report and Written Opinion dated Sep. 20, 2019 in International Application No. PCT/US2019/039912.
Jaramillo et al., "A cohort study examining headaches among veterans of Iraq and Afghanistan wars: Associations with traumatic brain injury, PTSD, and depression," Headache: The Journal of Head and Face Pain, 56(3):528-539 (2015).
Jennett et al., "Assessment of Outcome After Severe Brain Damage," The Lancet, 1(7905):480-484 (1975).
Jones et al., "Therapeutic strategies for the clinical blockade of IL-6/gp130 signaling," J Clin Invest, 121(9):3375-3383 (2011).
Jostock et al., "Soluble gp130 is the natural inhibitor of soluble interleukin-6 receptortranssignaling responses," Eur. J. Biochem. 268, 160-167 (2001).
Juengst et al., "Development and Content Validity of the Behavioral Assessment Screening Tool (BAST)," Disabil Rehabil., 41(10):1200-1206 (2019).
Kamins et al., "Posttraumatic Headache: Basic Mechanisms and Therapeutic Targets," Headache, 58(6):811-826 (2018).
King et al., "Plasma Cortisol Levels after Head Injury," Ann Surg., 172(6):975-984 (1970).
Kjeldgaard et al., "Chronic post-traumatic headache after mild head injury: a descriptive study," Cephalalgia, 34(3):191-200 (2014).
Kossmann et al., "Interleukin-6 released in human cerebrospinal fluid following traumatic brain injury may trigger nerve growth factor production in astrocytes," Brain Research, 713(1-2):143-152 (1996).
Kroenke et al., "The PHQ-9: A New Depression Diagnostic and Severity Measure," Psychiatric Annals, 32(9):509-515 (2002).
Krupp et al., "The fatigue severity scale: application to patients with multiple sclerosis and systemic lupus erythematosus," Arch Neurol., 46(10):1121-1123 (1989).
Kumar et al., "Epidemiology of Comorbid Conditions Among Adults 50 Years and Older with Traumatic Brain Injury," J Head Trauma Rehabil, 33(1):15-24 (2018).
Kumar et al., "Principal Components Derived from CSF Inflammatory Profiles Predict Outcome in Survivors after Severe Traumatic Brain Injury," Brain Behav Immun., 53:183-193 (2016).
Kumar et al., "Chronic Inflammation After Severe Traumatic Brain Injury: Characterization and Associations with Outcome at 6 and 12 Months Postinjury," J Head Trauma Rehabil, 30(6):369-381 (2015).
Kumar et al., "Acute CSF interleukin-6 trajectories after TBI: Associations with neuroinflammation, polytrauma, and outcome," Brain, Behavior, and Immunity, 45:253-262 (2015).
Lachman et al., "Monitoring Cognitive Functioning: Psychometric Properties of the Brief Test of Adult Cognition by Telephone," Assessment, 21(4):404-417 (2017).
Lanctôt et al., "Genetic predictors of response to treatment with citalopram in depression secondary to traumatic brain injury," Brain Inj. BI 24, 959-969 (2010) doi:10.3109/02699051003789229.
Lee et al., "Treelets—A Tool for Dimensionality Reduction and Multi-Scale Analysis of Unstructured Data," Proceedings of the Eleventh International Conference on Artificial Intelligence and Statistics, PMLR 2:259-266 (2007).
Lenze et al., "Elevated Cortisol in Older Adults with Generalized Anxiety Disorder is Reduced by Treatment: A Placebo-Controlled Evaluation of Escitalopram," Am J Geriatr Psychiatry, 19(5):482-490 (2011).
Leung et al., "rTMS in Alleviating Mild TBI Related Headaches—A Case Series," Pain Physician, 19:E347-E354 (2016).
Levin et al., "Chronic Daily Headache: Challenges in Treatment," R I Med J, 98(2):22-25 (2014).
Lipton et al., "Efficacy and Safety of Acetaminophen in the Treatment of Migraine: Results of a Randomized, Double-blind, Placebo-Controlled, Population-Based Study," Arch Intern Med., 160(22):3486-3492 (2000).
Lucas et al., "A prospective study of prevalence and characterization of headache following mild traumatic brain injury," Cephalalgia, 34(2):93-102 (2014).
Lucas et al., "The role of inflammation in CNS injury and disease," Br J Pharmacol., 147(Suppl 1): S232-S240 (2006).
Maes et al., "Targeting classical IL-6 signalling or IL-6 trans-signalling in depression?," Expert Opin. Ther. Targets 18(5):495-512 (2014).
Matsumoto et al., "Essential Roles of IL-6 Trans-Signaling in Colonic Epithelial Cells, Induced by the IL-6/Soluble-IL-6 Receptor Derived from Lamina Propria Macrophages, on the Development of Colitis-Associated Premalignant Cancer in a Murine Model," J Immunol Baltim. Md 1950 184 (3) 1543-1551 (2010).
Minen et al., "Post-concussive syndrome: a focus on post-traumatic headache and related cognitive, psychiatric, and sleep issues," Curr Neurol Neurosci Rep, 16:100 (2016).
Morieri et al., "Interleukin-6 "Trans-Signaling" and ischemic vascular disease: the important role of soluble gp130," Mediators Inflamm, 1396398 (2017).
Moye et al., "From blast to bench: A translational mini-review of posttraumatic headache," J Neurosci Res. 95(6):1347-1354 (2017).
Muñoz et al., "Cerebrospinal Fluid Cortisol Mediates Brain-Derived Neurotrophic Factor Relationships to Mortality after Severe TBI: A Prospective Cohort Study," Front Mol Neurosci., 10:44 (2017).
Nagin, "Group-Based Trajectory Modeling: An Overview," Ann Nutr Metab, 65:205-210 (2014).
Nakase-Richardson et al., "Prospective evaluation of the nature, course, and impact of acute sleep abnormality after traumatic brain injury," Arch Phys Med Rehabil. 94(5):875-882 (2013).
Niyonkuru et al., "Group-Based Trajectory Analysis Applications for Prognostic Biomarker Model Development in Severe TBI: A Practical Example," J Neurotrauma, 30:938-945 (2013).
Özge et al., "Chronic daily headache in the elderly," Curr Pain Headache Rep., 17(12):382 (2013).
Patrick et al., "Quality of life following intensive care," J Gen Intern Med., 3(3):218-223 (1988).
Penkowa et al., "Impaired inflammatory response and increased oxidative stress and neurodegeneration after brain injury in interleukin-6-deficient mice," Glia, 32(3):271-285 (2000).
Plummer et al., "Screening for anxiety disorders with the GAD-7 and GAD-2: a systematic review and diagnostic metaanalysis," Gen Hosp Psychiatry, 39:24-31 (2016).
Ranganathan et al., "Longitudinal sex and stress hormone profiles among reproductive age and post-menopausal women after severe TBI: A case series analysis," Brain Injury, 30(4):452-461 (2016).
Rappaport et al., "Evaluation of Coma and Vegetative States," Arch Phys Med Rehabil., 73(7):628-634 (1992).
Rochfort et al., "Cytokine-mediated dysregulation of zonula occludens-1 properties in human brain microvascular endothelium," Microvasc Res., 100:48-53 (2015).
Rose-John et al., "Interleukin-6 biology is coordinated by membrane-bound and soluble receptors: role in inflammation and cancer," J Leukoc Biol., 80(2):227-236 (2006).
Rose-John et al., "IL-6 trans-Signaling: The Heat is on," Immunity, 20(1):2-4 (2004).
Santarsieri et al., "Variable Neuroendocrine-Immune Dysfunction in Individuals with Unfavorable Outcome after Severe Traumatic Brain Injury," Brain Behav Immun., 45:15-27 (2015).

(56) References Cited

OTHER PUBLICATIONS

Scheffer et al., "Generalized epilepsy with febrile seizures plus. A genetic disorder with heterogeneous clinical phenotypes.," Brain, 120 ( Pt 3):479-490 (1997).
Scheller et al., "Updating interleukin-6 classic- and trans-signaling," Signal Transduction., 6(4):240-259 (2006).
Schwedt et al., "Persistent post-traumatic headache vs. migraine: an MRI study demonstrating differences in brain structure," J Headache Pain, 18(1):87 (2017).
Seidl et al., "Factors related to satisfaction with life in veterans with mild traumatic brain injury," Rehabilitation Psychology, 60(4):335-343 (2015).
Soares et al., "Interleukin-10 is an Independent Biomarker of Severe Traumatic Brain Injury Prognosis," Neuroimmunomodulation, 19(6):377-385 (2012).
Spitzer et al., "A brief measure for assessing generalized anxiety disorder: the GAD-7," Arch Intern Med, 166(10):1092-1097 (2006).
Stacey et al., "Natural history of headache five years after traumatic brain injury," Journal of Neurotrauma, 34(8):1558-1564 (2016).
Theeler et al., "Post-Traumatic Headaches in Civilians and Military Personnel: A Comparative, Clinical Review," Headache: The Journal of Head and Face Pain, 53(6):881-900 (2013).
Theeler et al., "Prevalence and impact of migraine among US Army soldiers deployed in support of Operation Iraqi Freedom," Headache: The Journal of Head and Face Pain, 48(6):876-882 (2008).
Tulsky et al., "TBI-QOL: Development and Calibration of Item Banks to Measure Patient Reported Outcomes Following Traumatic Brain Injury," J Head Trauma Rehabil, 31(1):40-51 (2016).
Van Houdenhove et al., "Does hypothalamic-pituitary-adrenal axis hypofunction in chronic fatigue syndrome reflect a 'crash' in the stress system?" Med Hypotheses, 72(6):701-705 (2009).
Wagner et al., "Association of KIBRA rs17070145 polymorphism and episodic memory in individuals with severe TBI," Brain Injury, 26(13-14):1658-1669 (2012).
Wagner et al., "Acute Serum Hormone Levels: Characterization and Prognosis after Severe Traumatic Brain Injury," J Neurotrauma, 28:871-888 (2011).
Weaver et al., "Genetic polymorphisms and traumatic brain injury: the contribution of individual differences to recovery," Brain Imaging and Behavior, 8(3):420-434 (2014).
Webster et al., "Sleep apnea in adults with traumatic brain injury: a preliminary investigation," Arch Phys Med Rehabil., 82(3):316-321 (2001).
Zaloshnja et al., "Prevalence of Long-Term Disability from Traumatic Brain Injury in the Civilian Population of the United States, 2005," J Head Trauma Rehabil, 23, 394-400 (2008).

\* cited by examiner

Santarsieri et al. Brain Behav Immun. 2015

Proposed Mechanism for IL-6 Signaling and HPA Axis

Hypothesis: IL6 signaling interacts with cortisol to impact outcome

Morieri et al. Mediators of Inflammation. 2017

| | Low | Recurs | Chronic | P-value |
|---|---|---|---|---|
| IL6 | 19.55 (5.9) | 14.29 (2.1) | 12.57 (1.3) | 0.837 |
| sgp130 | 159973 (6724) | 155197 (6459) | 147396 (6800) | 0.689 |
| sIL6R | 26433 (1395) | 23725 (1210) | 27839 (1316) | 0.115 |
| sgp130:sIL6R | 6.32 (0.36) | 6.72 (0.32) | 5.40 (0.20) | 0.005 ** |

Fig. 20

| Variables for Linear | Beta | P-value |
|---|---|---|
| IL6 0-5 days | -0.00383 | 0.0098 |
| Sgp130/sIL6R 0-5 days | 0.14876 | 0.0359 |
| Age | -0.05184 | 0.5246 |
| GCS | 0.25700 | 0.5710 |
| Years_Education_6M | 0.86045 | 0.1484 |

| Variables for Logistic | OR | P-value |
|---|---|---|
| Sgp130/sIL6R 0-5 days | 0.960 (0.920, 1.003) | 0.0668 |
| IL6 0-5 days | 1.001 (1.000, 1.002) | 0.1435 |
| Age | 1.007 (0.962, 1.054) | 0.7620 |
| GCS | 1.011 (0.786, 1.302) | 0.9297 |
| Years of Education | 0.721 (0.495, 1.051) | 0.0891 |

Higher ratios equal higher test performance (linear) and lower impairment (Logistic)

Fig. 21

| GV Variable | Beta | P-value |
|---|---|---|
| IL-6 0-3 months | -0.04431 | 0.3537 |
| Sgp130/sIL6R 0-3 days | 0.74658 | 0.0761 |
| Age | 0.04310 | 0.4174 |
| GCS | 0.87242 | 0.0018 |
| Years of Education | 2.05008 | <.0001 |

| LM | Beta | P-value |
|---|---|---|
| IL-6 0-3 months | -0.06772 | 0.1240 |
| Sgp130/sIL6R 0-3 days | 0.92572 | 0.0199 |
| Age | -0.01273 | 0.7794 |
| GCS | 0.90230 | 0.0001 |
| Years of Education | 1.25780 | 0.0017 |

Fig. 22

| | Point Estimate (CI) | P value |
|---|---|---|
| Sgp130/sIL6Rm 0-3 months | 0.771 (0.608, 0.979) | 0.0330 |
| IL6 0-3 months | 1.033 (0.994, 1.074) | 0.0967 |
| Age | 0.994 (0.965, 1.025) | 0.7193 |
| GCS | 0.756 (0.635, 0.901) | 0.0017 |
| Years of Education | 0.646 (0.485, 0.861) | 0.0028 |

Higher ratios equal lower impairment
Higher IL-6 levels equal higher impairment

Fig. 23

| | Point Estimate (CI) | P value |
|---|---|---|
| Sgp130/sIL6Rm 0-3 months | 0.753 (0.586, 0.968) | 0.0270 |
| IL6 0-3 months | 1.019 (0.989, 1.050) | 0.2183 |
| Age | 1.005 (0.978, 1.032) | 0.7357 |
| GCS | 0.780 (0.669, 0.911) | 0.0017 |
| Years of Education | 0.707 (0.549, 0.910) | 0.0072 |

Higher ratios equal lower impairment

IL-6 Family Biomarkers at mo 0-3 by Time until First Seizure up to 1 year

|  | PTE (n=23) | No PTE (n=101) | p-value |
|---|---|---|---|
| IL6, (Mean, SE) | 215.45 (143.84) | 96.86 (24.52) | 0.953 |
| IL6R, (Mean, SE) | 27338.32 (1597.74) | 24035.99 (738.85) | 0.062 |
| SGP130, (Mean, SE) | 172662.93 (8147.83) | 146721.34 (3447.81) | 0.006* |
| SGP130:IL6R, (Mean, SE) | 6.76 (0.43) | 6.68 (0.24) | 0.908 |

Fig. 27A

Cox Proportional Hazards Regression: IL-6 Family Biomarkers at mo 0-3 by Time until First Seizure to 1 year

|            | HR (95% CI)       | p-value |
|------------|-------------------|---------|
| IL-6       | 0.89 (0.55, 1.43) | 0.628   |
| IL-6R      | 1.42 (0.94, 2.12) | 0.093   |
| SGP130     | 2.03 (1.31, 3.16) | 0.002*  |
| SGP130:IL6R| 1.04 (0.69, 1.58) | 0.837   |

Adjusted models have sample size of n=113

Fig. 27B

| Marker       | HR (95% CI)          | p-value |
|--------------|----------------------|---------|
| IL-6         | 1.134 [0.859, 1.496] | 0.3761  |
| IL-6R        | 1.316 [0.887, 1.952] | 0.1730  |
| SGP130       | 1.590 [1.027, 2.462] | 0.0374  |
| SGP130:IL6R  | 0.933 [0.628, 1.386] | 0.7314  |

| Marker | OR (95% CI) | p-value |
|---|---|---|
| SGP130 | 1.713 [1.013, 2.895] | 0.0446 |

Fig. 30

Linear regression PHQ-9 Scores 12M

| | Beta | P-value |
|---|---|---|
| sgp130 0-3 months | 0.00006151 | 0.0031 |
| IL6 0-3 months | 0.40402 | 0.0002 |
| IL6*sgp130 | -0.00000233 | 0.0019 |
| Age | -0.00519 | 0.8415 |
| GCS | -0.18894 | 0.1513 |
| Gender | -0.62801 | 0.5486 |
| Premorbid Depression | 1.45824 | 0.1640 |

Fig. 31

Logistic regression
PHQ-9 Impaired status 12M

| | Point estimate (CI) | P-value |
|---|---|---|
| IL6_0_3 | 1.036 (1.007, 1.065) | 0.0146 |
| sgp130_0_3 | 1.000 (1.000, 1.000) | 0.2012 |
| sIL6R_0_3 | 1.000 (1.000, 1.000) | 0.4791 |
| Age | 0.986 (0.947, 1.027) | 0.5073 |
| GCS | 1.094 (0.905, 1.322) | 0.3543 |
| Men vs. Women | 0.704 (0.155, 3.199) | 0.6494 |
| Premorbid yes vs. no | 2.906 (0.781, 10.820) | 0.1117 |

Fig. 32

| Variable | Beta | P-values |
|---|---|---|
| Log IL-6 0-3 months | 4.82701 | 0.0016 |
| Sgp130 above/below q1 | 9.84214 | 0.0390 |
| Sgp130 above/below*log IL-6 | -3.54746 | 0.0360 |
| Age | -0.00841 | 0.7629 |
| GCS | -0.10638 | 0.4353 |
| Gender | -0.87842 | 0.4255 |
| Premorbid depression | 1.13633 | 0.3001 |

R^2=0.1593

Linear regression to 12M PHQ-9 Total Scores

| Variable | Beta | P-value |
|---|---|---|
| Log IL-6 0-3 months | 4.65181 | 0.0010 |
| Sgp130 above/below q1 | 9.40185 | 0.0365 |
| Sgp130 above/below*log IL-6 | -3.47732 | 0.0297 |
| Age | -0.00486 | 0.8626 |
| GCS | 0.02684 | 0.8544 |
| Gender | -1.62814 | 0.1621 |

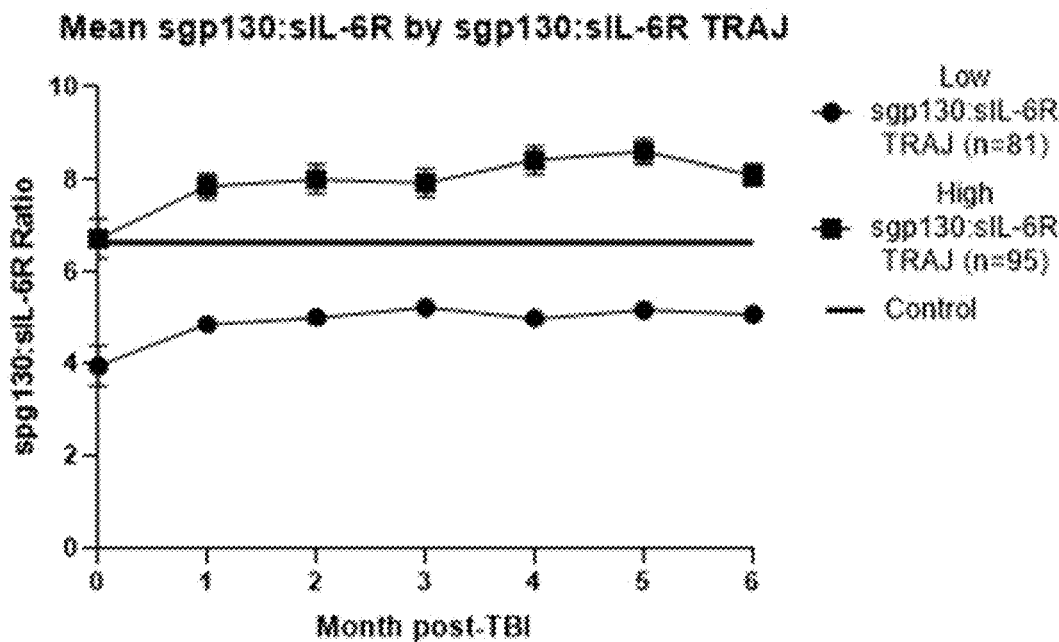

Fig. 41

| | Stratified Inflammatory Profiles | Low sIL-6R TRAJ | High sIL-6R TRAJ | Low sgp130:sIL-6R TRAJ | High sgp130:sIL-6R TRAJ |
|---|---|---|---|---|---|
| ACUTE PHENOMENA | Lymphopenia (Low Lymphocyte TRAJ) | 30.88 | 40.74 | 41.18 | 32.1 |
| | Neutrophilia (High Neutrophil TRAJ) | 53.73 | 44.43 | 55.88 | 65 |
| | Lymphopenia + Neutrophilia (High NLR TRAJ) | 23.53 | 35.8 | 41.18 | 20.99 |
| | Acute Hospital-Acquired Infection | 55.73 | 63.09 | 52.94 | 53.75 |
| CHRONIC PHENOMENA | Persistent Hypogonadotropic Hypogonadism | 37.93 | 36.36 | 42.62 | 31.75 |
| | Post-traumatic Depression (6mo.) | 31.48 | 29.03 | 32 | 26.79 |
| | Cognitive Impairment (6mo. Overall) | 40 | 57.89 | 50 | 46.44 |
| | Headache (Chronic Headache Trajectory) | 21.05 | 46.81 | 54.05 | 20.69 |
| | Seizure Incidence | 22.37 | 26.09 | 25.97 | 23.08 |
| OVERALL OUTCOME | Unfavorable GOS Score (6mo. Score=2,3) | 40.58 | 39.74 | 39.06 | 40.96 |
| | DRS Score (6mo. Moderate to Severe Disability) | 32.84 | 41.56 | 37.5 | 37.5 |

A

B

C

D

E

0-6M Cortisol Levels by sIL-6R TRAJ Group

F

0-6M Cortisol Levels by SGP130:sIL-6R TRAJ Group

Figs. 46A-46C
A
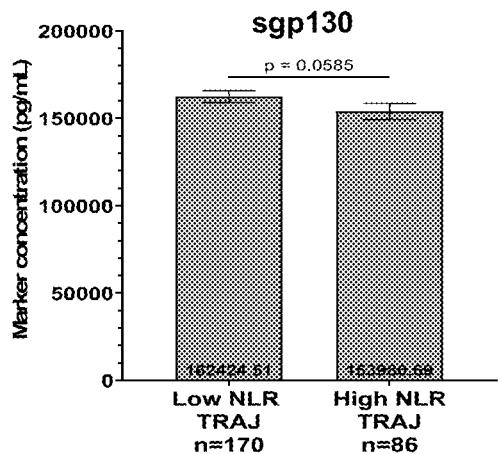
B
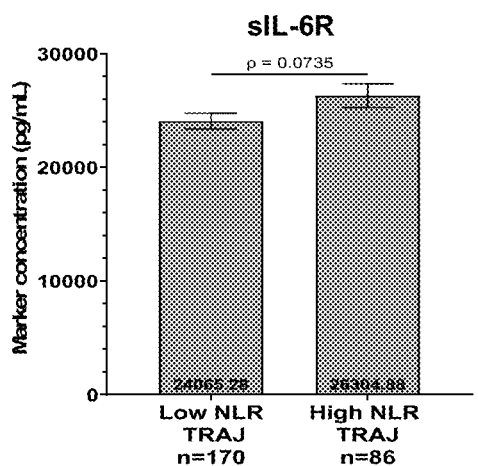
C
| % of TRAJ reported | Low NLR | High NLR |
|---|---|---|
| Low sIL-6R TRAJ | 76.47 | 23.53 |
| High sIL-6R TRAJ | 64.2 | 35.8 |
| Concordance | X2=2.64, p=*0.1041* | |
| Low sgp130:sIL-6R TRAJ | 58.82 | 41.18 |
| High sgp130:sIL-6R TRAJ | 79.01 | 20.99 |
| Concordance | X2=7.15, **p=*0.0075* | |

A

B

C

D

E

F

G

H

I
6M TNFa Levels by sIL-6R TRAJ Group

J
6M TNFa Levels by SGP130:sIL-6R TRAJ Group

K
6M TNFRI Levels by sIL-6R TRAJ Group $P=0.0059$

L
6M TNFRI Levels by SGP130:sIL-6R TRAJ Group $P=0.0100$

Fig. 58

Demographic characterization of the cohort and associations of demographic and clinical variables with sgp130:sIL-6R.

| | Total sample (n=79) | Association with sgp130:sIL-6R | p-value |
|---|---|---|---|
| Age, mean (SD) | 40.18 (2.13) | -0.047 | 0.707 |
| BMI, mean (SD) | 29.91 (1.62) | -0.048 | 0.816 |
| Gender, n (%; male) | 57 (72.2%) | -0.062 | 0.877 |
| GCS, mean (SD) | 8.31 (0.62) | 0.118 | 0.347 |
| Race, n (%) | | | |
| African American | 2 (3.0%) | -0.713 | 0.511 |
| White (referent) | 63 (95.5%) | - | - |
| Other | 1 (1.5%) | -1.597 | 0.296 |
| Mechanism of Injury, n (%) | | | |
| Motor Vehicle (referent) | 33 (55.9%) | - | - |
| Falls | 22 (37.3%) | 0.466 | 0.275 |
| Other | 4 (6.8%) | -0.255 | 0.786 |
| History of Anxiety, n (%) | 20 (26.3%) | -0.03 | 0.942 |
| History of Depression, n (%) | 23 (30.3%) | -0.019 | 0.963 |
| History of Alcoholism, n (%) | 3 (8.6%) | -0.153 | 0.766 |
| History of Headaches, n (%) | 19 (25.3%) | 0.082 | 0.839 |
| Ever smoke, n (%) | 57 (79.2%) | 0.35 | 0.46 |
| Ever illicit drug use, n (%) | 33 (47.1%) | -0.825 | 0.027 |

Demographic characterization of the cohort and associations of demographic and clinical variables with sgp130:sIL-6R. Bolded p-values indicate statistical significant differences (p<0.05) for Chi-Square associations between sgp130:sIL-6R and categorical variables and for Pearson correlations between sgp130:sIL-6R and continuous variables. BMI: Body Mass Index. GCS: Glasgow Coma Scale.

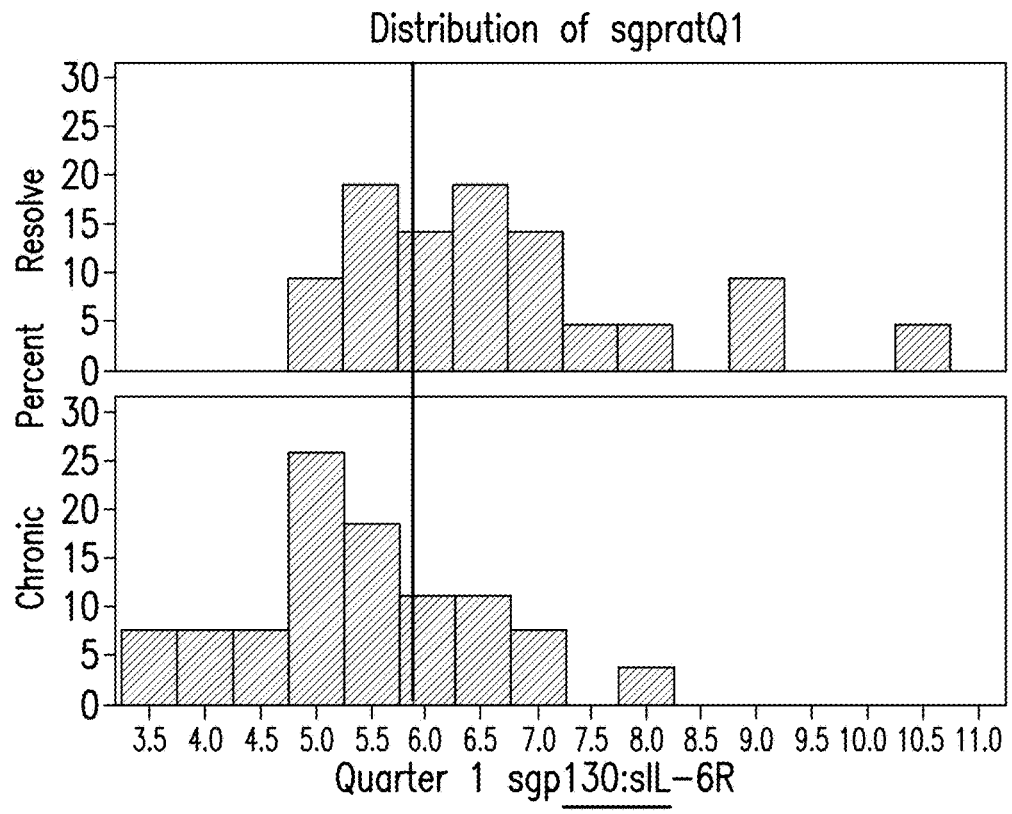

FIG. 61

Demographic characterization of the cohort by TRAJ group.

|  | Low (n=21) | Resolve (n=23) | Chronic (n=35) | pvalue |
|---|---|---|---|---|
| Age, mean (SD) | 49.14 (4.61) | 37.61 (3.47) | 36.49 (2.99) | 0.047 |
| BMI, mean (SD) | 27.11 (1.8) | 30.87 (3.0) | 31.24 (3.1) | 0.577 |
| Gender, n (%; male) | 17 (81.0) | 15 (65.2) | 25 (71.4) | 0.504 |
| GCS, mean (SD) | 9.62 (1.2) | 7.43 (1.1) | 8.09 (1.0) | 0.338 |
| Race, n (%) |  |  |  | 0.169 |
| African American | 0 | 0 | 2 (7.4) |  |
| White | 16 (94.1) | 22 (100) | 25 (92.6) |  |
| Other | 1 (5.9) | 0 | 0 |  |
| Mechanism of Injury, n (%) |  |  |  | 0.934 |
| Motor Vehicle | 8 (50) | 12 (63.2) | 13 (54.2) |  |
| Falls | 7 (43.8) | 6 (31.4) | 9 (37.5) |  |
| Other | 1 (6.2) | 1 (5.3) | 2 (8.3) |  |
| History of Anxiety, n (%) | 4 (21.1) | 6 (27.3) | 10 (28.6) | 0.892 |
| History of Depression, n (%) | 4 (21.1) | 8 (36.4) | 11 (31.4) | 0.558 |
| History of Alcoholism, n (%) | 0 | 0 | 3 (21.4) | 0.099 |
| History of Headaches, n (%) | 4 (20) | 5 (21.7) | 12 (34.3) | 0.489 |
| Ever smoke, n (%) | 9 (81.8) | 6 (60) | 9 (60) | 0.497 |
| Ever illicit drug use, n (%) | 7 (43.8) | 10 (52.6) | 17 (58.6) | 0.622 |

Bolded p-values indicate statistical significant differences (p<0.05) between TRAJ groups. BMI: Body Mass Index. GCS: Glasgow Coma Scale.

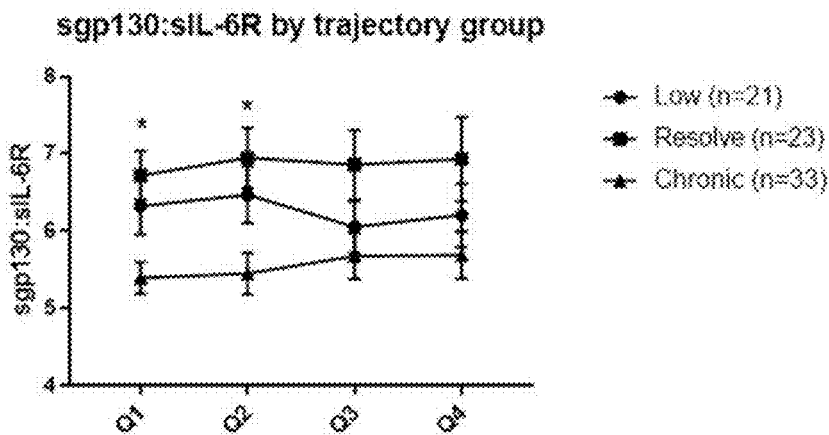

Fig. 64

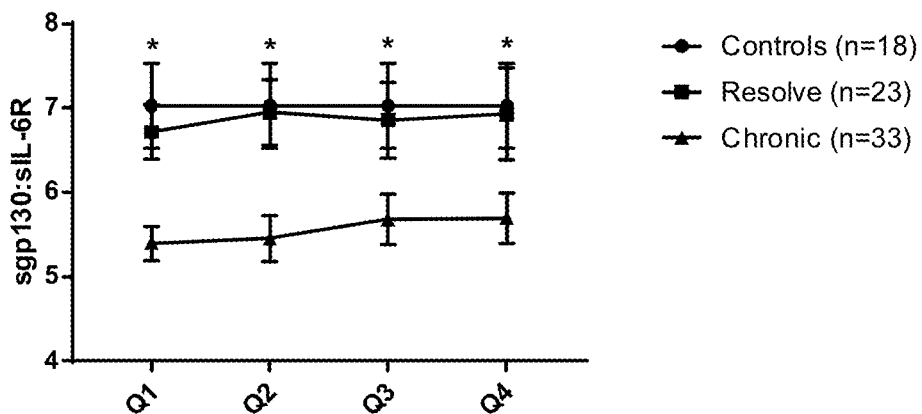

Fig. 65

Univariate and Multivariate models for Q1 sgp130:sIL6R.

| | Logistic Regression Model for *Chronic* vs. *Resolve* Headache TRAJ Groups | | | |
|---|---|---|---|---|
| | Univariate | | Multivariate | |
| | OR (95% CI) | pvalue | OR (95% CI) | pvalue |
| Q1 sgp130:sIL6R | 0.262 [0.104, 0.660] | 0.005 | 0.241 [0.087,0.669] | 0.006 |
| Age | | | 0.951 [0.896,1.010] | 0.103 |
| Sex | | | 2.881 [0.417,19.876] | 0.283 |
| GCS | | | 1.003 [0.758,1.327] | 0.986 |
| Pre-injury history of alcoholism | | | 0.502 [0.034,7.420] | 0.616 |
| Pre-injury history of headaches | | | 7.868 [0.600,103.270] | 0.116 |

The multivariate model was adjusted for age, sex, GCS, pre-injury history of alcoholism, and pre-injury history of headaches. Bolded p-values indicate statistical significance (p<0.05). GCS: Glasgow Coma Scale.

Figs. 66A-66B

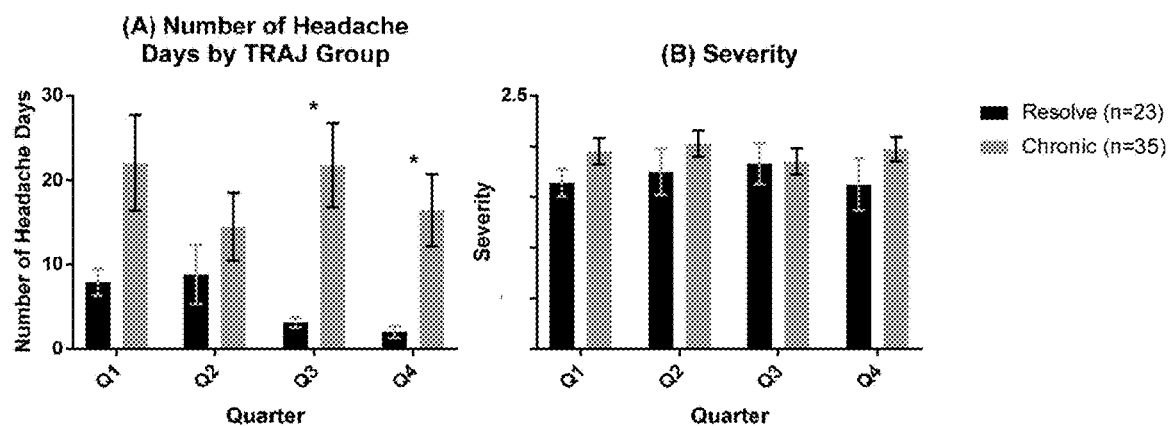

Fig. 67

Quality of life by TRAJ group

|  | Low (n=21) | Resolve (n=23) | Chronic (n=35) | pvalue |
|---|---|---|---|---|
| Total 6mo | 88.59 (3.2) | 76.21 (6.5) | 72.28 (5.0) | 0.063 |
| Total 12mo | 88.24 (3.3) | 84.58 (3.5) | 78.10 (3.3) | 0.113 |
| Physical 6mo | 87.65 (4.3) | 65.93 (8.4) | 72.60 (5.2) | 0.023 |
| Physical 12mo | 89.41 (4.1) | 87.53 (3.6) | 74.66 (4.8) | 0.016 |
| Emotional 6mo | 88.12 (4.8) | 77.86 (9.1) | 77.60 (4.9) | 0.324 |
| Emotional 12mo | 89.94 (3.5) | 92.26 (3.3) | 82.25 (3.5) | 0.075 |
| Cognitive 6mo | 83.82 (6.1) | 82.50 (7.0) | 71.00 (5.8) | 0.093 |
| Cognitive 12mo | 90.06 (3.4) | 87.89 (3.9) | 80.59 (3.8) | 0.127 |

Quality of Life was measured by self-reported percent back to pre-injury normal functioning and stratified by TRAJ group. Mean (stderr) of total, physical, emotional, and cognitive percentages back to normal were reported at 6 and 12 months. Statistically significant differences between TRAJ groups are indicated by bolded p-values ($p<0.05$).

| | Quarter | Low (n=21) | Resolve (n=23) | Chronic (n=35) | pvalue |
|---|---|---|---|---|---|
| GAD-7 | 1 | 1.74 (0.8) | 4.88 (1.4) | 4.27 (1.2) | 0.105 |
| Row a | 2 | 2.19 (0.9) | 2.85 (0.8) | 3.67 (0.7) | 0.249 |
| | 3 | 1.90 (0.9) | 3.36 (0.9) | 4.61 (0.8) | 0.021 |
| | 4 | 1.60 (0.8) | 2.96 (0.8) | 3.72 (0.6) | 0.031 |
| PTD (n,%) | 1 | 4 (26.7) | 7 (43.8) | 7 (29.2) | 0.617 |
| Row b | 2 | 3 (17.7) | 6 (28.6) | 12 (44.4) | 0.160 |
| | 3 | 3 (20) | 5 (25) | 11 (39.3) | 0.410 |
| | 4 | 1 (5.9) | 4 (19.1) | 11 (37.9) | 0.040 |
| PROMIS | 1 | 11.89 (1.6) | 18.65 (1.5) | 16.05 (1.3) | 0.002 |
| Row c | 2 | 12.52 (1.4) | 14.53 (1.2) | 16.26 (1.3) | 0.066 |
| | 3 | 12.47 (1.7) | 14.53 (1.7) | 15.87 (1.4) | 0.071 |
| | 4 | 11.41 (1.1) | 12.94 (1.2) | 14.83 (1.2) | 0.068 |
| FSS | 1 | 16.43 (3.3) | 27.73 (2.5) | 24.67 (2.9) | 0.004 |
| Row d | 2 | 17.81 (2.8) | 22.10 (2.7) | 24.35 (3.0) | 0.303 |
| | 3 | 16.99 (3.5) | 22.39 (3.9) | 23.74 (2.9) | 0.135 |
| | 4 | 14.94 (2.7) | 19.27 (3.0) | 22.44 (2.5) | 0.070 |

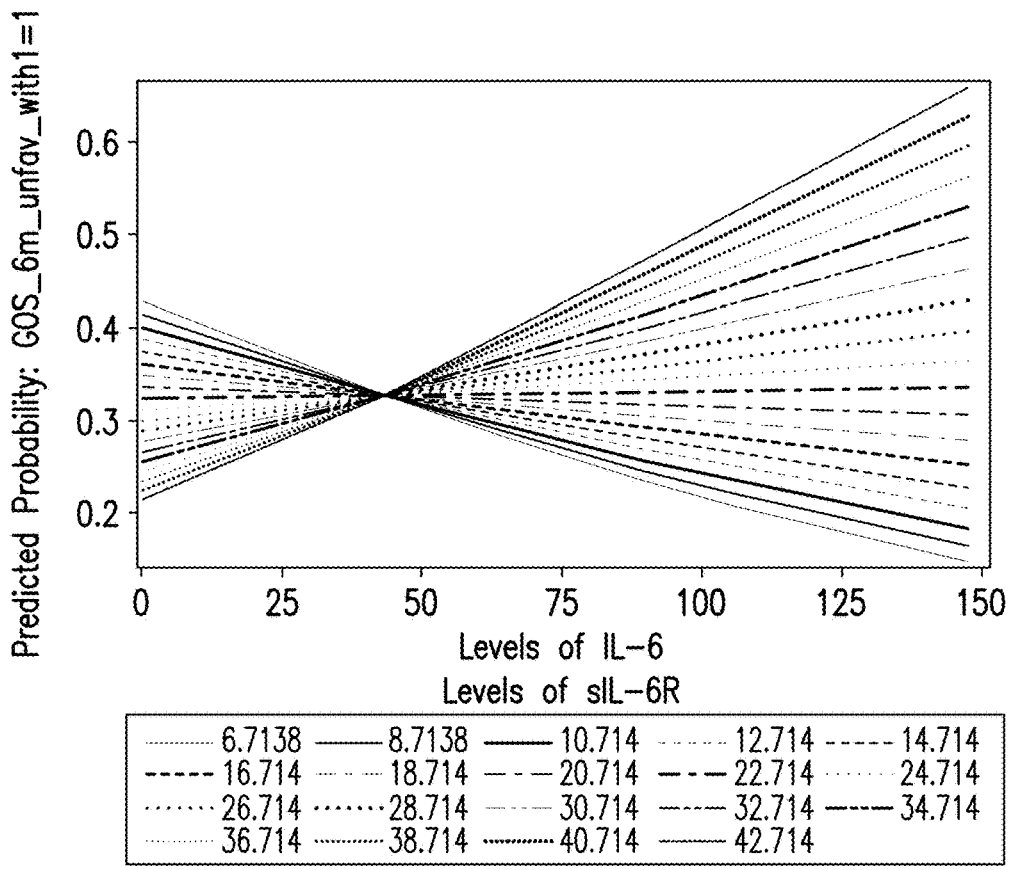

Note: Interaction graphic refers to month 0-3 mean levels of IL-6 (pg/mL) & sIL6R (ng/mL)

FIG. 70A

| Variables | OR (95% CI) | p-value |
|---|---|---|
| Age | 0.993 (0.972, 1.015) | p=0.55 |
| Gender | 0.423 (0.176, 1.018) | p=0.05 |
| sgp130 (ng/mL) | 1.0 (0.988, 1.011) | p=0.95 |
| IL-6 (pg/mL) | 0.986 (0.972, 1.00) | p=0.049 |
| IL-6R (ng/mL) | 0.972 (0.917, 1.031) | p=0.35 |
| *IL-6*IL-6R Interaction | 1.001 (1.00, 1.001) | p=0.047 |

*The interaction term and related plot show that At sIL-6R levels below 22.7K, rising IL-6 levels reduce poor outcome. At sIL-6R levels above this cut point, IL-6 levels increasingly contribute to poor outcome.

METHODS FOR TREATING AND REDUCING TRAUMATIC BRAIN INJURY-ASSOCIATED IMPAIRMENTS USING SGP130

CROSS-REFERENCE TO RELATED APPLICATIONS

This application is a continuation of International Patent Application No. PCT/US2019/039912, filed on Jun. 28, 2019, which claims priority to U.S. Provisional Application No. 62/692,405, filed on Jun. 29, 2018, the contents of each of which are hereby incorporated by reference in their entireties, and to each of which priority is claimed.

GRANT INFORMATION

This invention was made with government support under grant numbers 90DP0041 awarded by the Administration for Community Living/National Institute on Disability, Independent Living, and Rehabilitation Research; R49 CE323155 awarded by the Center for Disease Control; and W81XWH-07-1-0701 awarded by the Army/MRMC. The government has certain rights in the invention.

1. TECHNICAL FIELD

The present disclosure relates to methods, compositions, and kits for treating traumatic brain injury (TBI), and TBI-associated impairments (e.g., posttraumatic headache (PTH), posttraumatic depression (PTD), cognitive deficits, posttraumatic epilepsy (PTE), and seizure) in a subject, including administering to the subject a spg130, or an agent that promotes the binding of sgp130 and sIL-6R and/or reduces sIL-6R mediated trans-signaling. The present disclosure also relates to biomarkers for predicting and monitoring a subject's response to a treatment to TBI-associated impairments.

2. BACKGROUND

Traumatic brain injury (TBI) results in at least 2.5 million visits to hospitals and emergency departments annually in the United States, and the incidence of TBI is increasing (Centers for Disease Control and Prevention, National Center for Injury Prevention and Control, 2016a. TBI: Get the Facts; Centers for Disease Control and Prevention, National Center for Injury Prevention and Control, 2016b. Rates of TBI-related Emergency Department Visits, Hospitalizations, and Deaths by Sex—United States, 2001-2010). The long-term effects of TBI can be prevalent and debilitating; it is estimated that 1.1% of Americans live with TBI-related disabilities (Zaloshnja et al., 2008 J. Head Trauma Rehabil. 23, 394-400). Common TBI-associated impairments include posttraumatic headache (PTH), posttraumatic depression (PTD), cognitive deficits, and epilepsy. The secondary injury response early after severe TBI can be characterized by an acute innate immune response. However, chronic inflammation after TBI is not well understood, and without sufficiently effective treatment.

Post-traumatic headache (PTH) is a secondary headache disorder that can result after a traumatic brain injury (TBI) (Minen et al., Curr Neurol Neurosci Rep. 2016; 16(11):100; Theeler et al., Headache: The Journal of Head and Face Pain. 2013; 53(6):881-900). It has been reported wide incidence rates of headache after a TBI, ranging from 13% to 90% (Jaramillo et al., Headache: The Journal of Head and Face Pain. 2015; 56(3):528-539; Hong et al., J Headache Pain. 2017; 18(1); Moye et al., J Neurosci Res. 2017; 95(6):1347-1354). The disparity in incidence rates can be due to varying definitions of headache, differences in TBI severities, and data collection methods and time points. The prevalence of headaches is reported to remain above 40% throughout the first year after injury (Stacey et al., Journal of Neurotrauma. 2016; 34(8):1558-1564; Hoffman et al., J Neurotrauma. 2011; 28(9):1719-1725; Lucas et al., Cephalalgia. 2014; 34(2):93-102).

Post-traumatic headache (PTH) is a secondary headache disorder that can result after a traumatic brain injury (TBI). Incidence rates of headache after a TBI range from 13% to 90%. Detrimental long-term effects of headaches have been demonstrated in TBI (Hu et al., Canadian Journal of Neurological Sciences. 2017; 44(4):384-390; Kjeldgaard et al., Cephalalgia. 2014; 34(3):191-200; Minen et al., Curr Neurol Neurosci Rep. 2016; 16(11):100; Hong et al., J Headache Pain. 2017; 18(1); Stacey et al., Journal of Neurotrauma. 2016; 34(8):1558-1564), US Army soldiers deployed in support of Operation Iraqi Freedom (Theeler et al., Headache: The Journal of Head and Face Pain. 2008; 48(6):876-882), and in populations with chronic migraine (Bigal et al., Neurology. 2008; 71(8):559; Schwedt et al., J Headache Pain. 2017; 18(1)). Headaches after TBI do not occur in isolation, and individuals with TBI often have multiple co-occurring impairments, including anxiety and depression (Jaramillo et al., Headache: The Journal of Head and Face Pain. 2015; 56(3):528-539), seizures (Hong et al., J Headache Pain. 2017; 18(1)), cognitive issues (Minen et al., Curr Neurol Neurosci Rep. 2016; 16(11):100; Kjeldgaard et al., Cephalalgia. 2014; 34(3):191-200), other neuropsychiatric symptoms (Bomyea et al., Headache: The Journal of Head and Face Pain. 2016; 56(4):699-710), and sleep disorders such as insomnia and sleep apnea (Theeler et al., Headache: The Journal of Head and Face Pain. 2013; 53(6):881-900; Hu et al., Canadian Journal of Neurological Sciences. 2017; 44(4):384-390; Nakase-Richardson et al., Arch Phys Med Rehabil. 2013 May; 94(5):875-82 Seidl et al., Rehabilitation Psychology. 2015; 60(4):335-343; Webster et al., Arch Phys Med Rehabil. 2001; 82(3):316-321). Headaches negatively impact quality of life (Theeler et al., Headache: The Journal of Head and Face Pain. 2008; 48(6):876-882; Bigal et al., Neurology. 2008; 71(8):559), satisfaction with life (Seidl et al., Rehabilitation Psychology. 2015; 60(4):335-343), and physical and social function (Kjeldgaard et al., Cephalalgia. 2014; 34(3):191-200).

Another contributor to post-injury disability is cognitive deficits due to TBI, which can impair the affect individuals' overall neurorecovery through reduced capacities for activities of daily living, social relationships, recreation, and active participation in the community. Common cognitive impairments following TBI include attention and memory deficits, impaired visual or spatial conceptualization, disturbance of executive function. Disturbances of attention and memory are particularly problematic, as disruption of these primary cognitive functions can cause or exacerbate additional disturbances in executive function, communication, and other relatively more complex cognitive functions.

There have been certain efforts over the last several decades to identify acute neuroprotective treatments for TBI populations. However, mortality rates for severe TBI are largely unchanged over the last decade. There are also still no treatments that have received a Level I recommendation for efficacy in the recent $4^{th}$ edition TBI Guidelines, and no treatments have been approved by the Food and Drug Administration following Phase III trials.

Thus, there remain needs for effective treatments for TBI-associated impairments cognition deficits, depression, PTH, PTE, and deficits to neurorecovery.

3. SUMMARY

The present disclosure provides methods, compositions, and kits for treating traumatic brain injury (TBI) and TBI-associated impairments (e.g., posttraumatic headache (PTH), posttraumatic depression (PTD), cognitive deficits, posttraumatic epilepsy (PTE), and seizure) in a subject.

In one aspect, the present disclosure provides methods of treating a traumatic brain injury (TBI), or treating or reducing the risk of a TBI-associated impairment in a subject, including administering to the subject a spg130, or an agent that promotes the binding of sgp130 and sIL-6R and/or reduces sIL-6R mediated trans-signaling.

In certain embodiments, the method improves outcome of TBI in the subject. In certain embodiments, the method reduces long-term disability in the subject. In certain embodiments, the method promotes central nervous system repair, regeneration, and/or remodeling in the subject.

In certain embodiments, the TBI-associated impairment is selected from posttraumatic headache (PTH), posttraumatic depression (PTD), cognitive deficits, posttraumatic epilepsy (PTE), and seizure.

In certain embodiments, the sgp130 includes a sgp130/Fc dimer.

In certain embodiments, the agent that promotes the binding of sgp130 and sIL-6R and/or reduces sIL-6R mediated trans-signaling is a monoclonal antibody. In certain embodiments, the monoclonal antibody is siltuximab. In certain embodiments, the monoclonal antibody is an anti-IL-6 trans-signaling antibody (e.g., 25F10).

In another aspect, the present disclosure provides methods for monitoring a subject's responsiveness to a treatment for a TBI-associated impairment, where the treatment includes administering a spg130 to the subject. In an example, the method includes: (a) determining the level of a biomarker in a sample obtained from the subject before receiving the treatment; (b) determining the level of the biomarker in a sample obtained from the subject at during or after receiving the treatment; and (c) comparing the levels of the biomarker in the samples. A change of the level of the biomarker during or after the treatment indicates the responsiveness of the subject to the treatment. The biomarker can be selected from sIL-6R, sgp130, IL-6, sgp130:sIL-6R ratio, sIL-2Ra, IL-2, sIL-2Ra:IL-2 ratio, TNFα, TNFRI, TNFRI:TNFα ratio, Neutrophil:Lymphocyte ratio (NLR), and combinations thereof.

In certain embodiments, the spg130 or the agent that promotes the binding of sgp130 and sIL-6R and/or reduces sIL-6R mediated trans-signaling, is administered to the subject at the post-acute and/or chronic stage of the TBI. In certain embodiments, the spg130 or the agent that promotes the binding of sgp130 and sIL-6R and/or reduces sIL-6R mediated trans-signaling is administered to the subject between about 24 hours and about 3 days, between about 24 hours and about 3 weeks, between about 24 hours and about 3 months, between 24 hours and about 6 months, between 24 hours and about 8 months, or between 24 hours and 12 months after occurrence of TBI.

In certain embodiments, the method further includes continuing the treatment if the subject is responsive to the treatment. In certain embodiments, the method further includes treating the subject with a different treatment or a different dosing regimen for the TBI-associated impairment if the subject is not responsive to the treatment.

In another aspect, the present disclosure provides methods for identifying a subject who has sustained TBI as likely to respond to a treatment for a TBI-associated impairment, where the treatment includes administering a spg130 to the subject. In an example, the method includes: (a) determining the level of a biomarker in a sample obtained from the subject; (b) comparing the level of the biomarker to a reference level of the biomarker; and (c) identifying the subject as likely to respond to the treatment based on the comparison. The biomarker can be selected from white blood cells indices (e.g., Neutrophil-Lymphocyte Ratio (NLR), absolute lymphocyte counts), sIL-6R, sgp130, IL-6, sgp130:sIL-6R ratio, sIL-2Ra, IL-2, sIL-2Ra:IL-2 ratio, TNFα, TNFRI, TNFRI:TNFα ratio, and combinations thereof.

In certain embodiments, the method further includes administering the treatment to the subject that is identified as likely to respond to the treatment. In certain embodiments, the treatment is administered at the post-acute and/or chronic stage of the TBI. In certain embodiments, the sample is a blood sample. In certain embodiments, the blood sample is a plasma sample, a serum sample, or a central nervous system (CNS)-derived exosomal fraction of the blood sample. In certain embodiments, the biomarker is sIL-6R, and if the level of sIL-6R is higher than the reference level of sIL-6R, the subject is likely to respond to the treatment. In certain embodiments, the reference level of sIL-6R is about 22,000 pg/ml. In certain embodiments, the biomarker is sgp130:sIL-6R ratio, and if the level of sgp130:sIL-6R ratio is lower than the reference level of sgp130:sIL-6R ratio, the subject is likely to respond to the treatment. In certain embodiments, the reference level of sgp130:sIL-6R ratio is about 6.5. In certain embodiments, the biomarker is NLR, and if the level of NLR is higher than the reference level of the NLR, the subject is likely to respond to the treatment. In certain embodiments, the reference level of the NLR is about 10.

In certain embodiments, the biomarker is sgp130, and if the level of sgp130 is lower than the reference level of sgp130, the subject is likely to respond to the treatment. In certain embodiments, the reference level of sgp130 is about 130,000 pg/ml. In certain embodiments, the TBI-associated impairment is post-traumatic depression (PTD).

In certain embodiments, the TBI-associated impairment is PTE, and if the level of sgp130 is higher than the reference level of sgp130, the subject is likely to respond to the treatment. In certain embodiments, the reference level of sgp130 is between about 140,000 pg/ml and about 200,000 pg/ml, or between about 160,000 pg/ml and about 180,000 pg/ml. In certain embodiments, the reference level of sgp130 is about 160,000 pg/ml, or about 180,000 pg/ml.

In certain embodiments, the biomarker is a combination of sIL-6R and sgp130:sIL-6R ratio. In certain embodiments, if the level of sIL-6R is higher than the reference level of sIL-6R and the level of sgp130:sIL-6R ratio is lower than the reference level of sgp130:sIL-6R ratio, the subject has an endogenous risk profile, and is likely to respond to the treatment. In certain embodiments, if the level of sIL-6R is lower than the reference level of sIL-6R and the level of sgp130:sIL-6R ratio is higher than the reference level of sgp130:sIL-6R ratio, the subject has an endogenous non-risk or reduced risk profile. In certain embodiments, the reference level of sIL-6R is about 22,000 pg/ml, and the reference level of sgp130:sIL-6R ratio is about 6.5.

In another aspect, the present disclosure provides methods for predicting a subject who has sustained TBI as likely to develop a TBI-associated impairment. In an example, a method includes: (a) determining the level of a biomarker in a sample obtained from the subject; (b) comparing the level of the biomarker to a reference level of the biomarker; and (c) predicting the subject as likely to develop the TBI-associated impairment based on the comparison. The biomarker can be selected from white blood cells indices (e.g., Neutrophil-Lymphocyte Ratio (NLR), absolute lymphocyte counts), sIL-6R, sgp130, IL-6, sgp130:sIL-6R ratio, sIL-2Ra, IL-2, sIL-2Ra:IL-2 ratio, TNFα, TNFRI, TNFRI:TNFα ratio, and combinations thereof. In certain embodiments, the sample is a blood sample. In certain embodiments, the blood sample is a plasma sample, a serum sample, or a central nervous system (CNS)-derived exosomal fraction of the blood sample.

In certain embodiments, the biomarker is sIL-6R, and if the level of sIL-6R is higher than the reference level of sIL-6R, the subject is likely to develop a TBI-associated impairment. In certain embodiments, the reference level of sIL-6R is about 22,000 pg/ml. In certain embodiments, the biomarker is sgp130:sIL-6R ratio, and if the level of sgp130:sIL-6R ratio is lower than the reference level of sgp130:sIL-6R ratio, the subject is likely to develop a TBI-associated impairment. In certain embodiments, the reference level of sgp130:sIL-6R ratio is about 6.5.

In certain embodiments, the biomarker is sgp130, and if the level of sgp130 is lower than the reference level of sgp130, the subject is likely to develop a TBI-associated impairment. In certain embodiments, the reference level of sgp130 is about 130,000 pg/ml. In certain embodiments, the TBI-associated impairment is PTD.

In certain embodiments, the TBI-associated impairment is PTE, and if the level of sgp130 is higher than the reference level of sgp130, the subject is likely to develop PTE. In certain embodiments, the reference level of sgp130 is between about 140,000 pg/ml and about 200,000 pg/ml, or between about 160,000 pg/ml and about 180,000 pg/ml. In certain embodiments, the reference level of sgp130 is about 160,000 pg/ml, or about 180,000 pg/ml.

In certain embodiments, the biomarker is a combination of sIL-6R and sgp130:sIL-6R ratio. In certain embodiments, if the level of sIL-6R is higher than the reference level of sIL-6R and the level of sgp130:sIL-6R ratio is lower than the reference level of sgp130:sIL-6R ratio, the subject has an endogenous risk profile, and is likely to develop a TBI-associated impairment. In certain embodiments, if the level of sIL-6R is lower than the reference level of sIL-6R and the level of sgp130:sIL-6R ratio is higher than the reference level of sgp130:sIL-6R ratio, the subject has an endogenous non-risk or reduced risk profile. In certain embodiments, the reference level of sIL-6R is about 22,000 pg/ml, and the reference level of sgp130:sIL-6R ratio is about 6.5.

In certain embodiments, the TBI-associated impairment is selected from posttraumatic headache (PTH), posttraumatic depression (PTD), cognitive deficits, posttraumatic epilepsy (PTE), and seizure.

In certain embodiments, the TBI-associated impairment is PTE and the biomarker is sgp130, wherein if the level of sgp130 is higher than the reference level of sgp130, the subject is likely to develop a TBI-associated impairment.

In another aspect, the present disclosure provides kits for identifying a subject who has sustained TBI as likely to respond to a treatment for a TBI-associated impairment. In an example, a kit includes a detector for detecting a biomarker, where the biomarker is selected from white blood cells indices (e.g., Neutrophil-Lymphocyte Ratio (NLR), absolute lymphocyte counts), sIL-6R, sgp130, IL-6, sgp130:sIL-6R ratio, sIL-2Ra, IL-2, sIL-2Ra:IL-2 ratio, TNFα, TNFRI, TNFRI:TNFα ratio, and combinations thereof.

In another aspect, the present disclosure provides kits for monitoring a subject's responsiveness to a treatment for a TBI-associated impairment. In an example, a kit includes a detector for detecting a biomarker, where the biomarker is selected from the group consisting of sIL-6R, sgp130, IL-6, sgp130:sIL-6R ratio, sIL-2Ra, IL-2, sIL-2Ra:IL-2 ratio, TNFα, TNFRI, TNFRI:TNFα ratio, NLR, and combinations thereof. In certain embodiments, the treatment includes administering a spg130 or an agent that promotes the binding of sgp130 and sIL-6R and/or reduces sIL-6R mediated trans-signaling.

In one aspect, the present disclosure provides a method of treating a traumatic brain injury (TBI) in a subject that has sustained TBI including administering to the subject in need thereof a sgp130, or an agent that promotes the binding of sgp130 and sIL-6R and/or reduces sIL-6R mediated trans-signaling.

In another aspect, the present disclosure provides a method of treating a TBI-associated impairment in a subject that has sustained TBI including administering to the subject in need thereof a sgp130, or an agent that promotes the binding of sgp130 and sIL-6R and/or reduces sIL-6R mediated trans-signaling.

In another aspect, the present disclosure provides a method of improving outcome in a subject that has sustained TBI including administering to the subject in need thereof a sgp130, or an agent that promotes the binding of sgp130 and sIL-6R and/or reduces sIL-6R mediated trans-signaling.

In certain embodiments, the TBI-associated impairment is selected from the group consisting of PTH, PTD, cognitive deficits, PTE, and seizure.

In certain embodiments, the sgp130 is an Fc dimerized version of sgp130 (Fc-sgp130). In certain embodiments, the agent that promotes the binding of sgp130 and sIL-6R and/or reduces sIL-6R mediated trans-signaling is a monoclonal antibody. In certain embodiments, the monoclonal antibody is siltuximab. In certain embodiments, the monoclonal antibody is an anti-IL-6 trans-signaling antibody (e.g., 25F10) (Garbers et al., J Biol Chem. 2011; 286(50): 42959-42970, the contents of which are incorporated as reference by its entirety).

In another aspect, the present disclosure provides methods for determining the risk of developing a TBI-associated impairment, condition, or related symptom in a subject that has sustained a TBI. In an example, a method includes measuring sgp130:sIL-6R ratio in a sample obtained from the subject that has sustained TBI, and comparing the sgp130:sIL-6R ratio to a predetermined reference value, where (a) if the sgp130:sIL-6R ratio is lower than the predetermined reference value, the subject is likely to develop the TBI-associated impairment, condition, or related symptom; and (b) if the sgp130:sIL-6R ratio is higher than the predetermined reference value, the subject is less likely to develop the TBI-associated impairment, condition, or related symptom.

In another aspect, the present disclosure provides methods for determining the risk of developing a TBI-associated impairment, condition, or related symptom in a subject that has sustained a TBI. In an example, a method includes measuring sgp130:sIL-6R ratio in two or more samples obtained from the subject over a period of time, where the subject has sustained a TBI, and comparing the sgp130:sIL-6R ratios among samples (a) if the sgp130:sIL-6R ratio decreases over the period of time, the subject is likely to develop a TBI-associated impairment, condition, or related symptom; and (b) if the sgp130:sIL-6R ratio increases or generally remain the same, the subject is less likely to develop a TBI-associated impairment, condition, or related symptom.

In another aspect, the present disclosure provides methods for determining the risk of developing a TBI-associated impairment, condition, or related symptom in a subject that has sustained a TBI. In an example, a method includes in measuring a biomarker in a sample obtained from the subject, where the level of the biomarker indicates the likelihood of the subject to be at risk of developing a TBI-associated impairment, condition, or related symptom. The biomarker can be selected from sIL-6R, sgp130, IL-6, sgp130:sIL-6R ratio, sIL-2Ra, IL-2, sIL-2Ra:IL-2 ratio, TNFα, TNFRI, TNFRI:TNFα ratio, Neutrophil:Lymphocyte ratio (NLR), and combinations thereof. In certain embodiments, the sgp130 level indicates the likelihood of the subject to be at risk of developing a TBI-associated impairment, condition, or related symptom when the IL-6 or sIL-6R level is high.

In certain embodiments, the method further includes treating the subject that is likely to develop a TBI-associated impairment, condition, or related symptom with a sgp130 or an agent that promotes the binding of sgp130 and sIL-6R and/or reduces sIL-6R mediated trans-signaling, citicoline, a neurostimulator, dopamine agonists, and/or anticonvulsants. Any agents or treatment known in the art for treating TBI-associated impairment, condition, or related symptom can be used with the methods disclosed herein.

In another aspect, the present disclosure provides methods for monitoring the responsiveness of a subject to a treatment regimen for a TBI-associated impairment, condition, or related symptom, where the subject has sustained TBI. In an example, a method includes measuring sgp130:sIL-6R ratio in a sample obtained from the subject, and comparing the sgp130:sIL-6R ratio to a predetermined reference value, where (a) if the sgp130:sIL-6R ratio is lower than the predetermined reference value, the subject is not responsive to the treatment regimen; and (b) if the sgp130:sIL-6R ratio is higher than the predetermined reference value, the subject is responsive to the treatment regimen.

In another aspect, the present disclosure provides methods for monitoring the responsiveness of a subject to a treatment regimen for a TBI-associated impairment, condition, or related symptom, where the subject has sustained TBI. In an example, a method includes measuring sgp130:sIL-6R ratio in two or more samples collected from the subject before, during, and/or after receiving the treatment regimen, and comparing the sgp130:sIL-6R ratios measured in the samples, where (a) if the sgp130:sIL-6R ratio decreases during or after the treatment regimen, the subject is not responsive to the treatment regimen, and (b) if the sgp130:sIL-6R ratio increases during or after the treatment regimen, the subject is responsive to the treatment regimen.

In another aspect, the present disclosure provides methods for monitoring the responsiveness of a subject to a treatment regimen for a TBI-associated impairment, condition, or related symptom, where the subject has sustained TBI. In an example, a method includes a biomarker in a sample obtained from the subject before, during and/or after receiving the treatment regimen, where a change of the level of the biomarker indicates the responsiveness of the subject to the treatment regimen. The biomarker can be selected from sIL-6R, sgp130, IL-6, sgp130:sIL-6R ratio, sIL-2Ra, IL-2, sIL-2Ra:IL-2 ratio, TNFα, TNFRI, TNFRI:TNFα ratio, Neutrophil:Lymphocyte ratio (NLR), and combinations thereof. In certain embodiments, the sgp130 level indicates the responsiveness of the subject to the treatment regimen when the IL-6 or sIL-6R level is high.

In certain embodiments, the method further includes adjusting the treatment regimen in the subject that is determined to be not responsive to the treatment regimen.

In another aspect, the present disclosure provides methods of determining the likelihood of good outcome after TBI. In an example, a method includes determining the sgp130:sIL-6R ratio, where an increased sgp130:sIL-6R ratio is linked with greater odds of experiencing good outcome.

In another aspect, the present disclosure provides methods of treating a subject that has sustained TBI. In an example, a method includes determining the sgp130:sIL-6R ratio, and treating a subject having a decreased sgp130:sIL-6R ratio (and therefore at risk for poor outcome) with a treatment regimen, including administration of one or more of sgp130 or an agent that promotes the binding of sgp130 and sIL-6R and/or reduces sIL-6R mediated trans-signaling. Any agents or treatment known in the art for treating TBI-associated impairment, condition, or related symptom can be used with the methods disclosed herein. Non-limiting examples of such treatment regimen include citicoline, a neurostimulator, dopamine agonists, and/or anticonvulsants.

In certain embodiments poor outcome is selected from PTH, PTD, PTE cognitive deficits, and seizure.

In another aspect, the present disclosure provides kits for determining whether a subject is at risk of developing a TBI-associated impairment, condition, or related symptom, where the subject has sustained a TBI. In an example, a kit includes g a detector for detection a sgp130:sIL-6R ratio, a sgp130 level, a sIL-6R level, a IL-6 level, a sIL-2Ra, IL-2 level, a sIL-2Ra:IL-2 ratio, a TNFα level, a TNFRI level, a TNFRI:TNFα ratio, and/or a Neutrophil:Lymphocyte ratio (NLR).

In another aspect, the present disclosure provides kits for monitoring the responsiveness of a subject to a treatment regimen for a TBI-associated impairment, condition, or related symptom. In an example, a kit includes a detector for detection a sgp130:sIL-6R ratio, a sgp130 level, a sIL-6R level, a IL-6 level, a sIL-2Ra, IL-2 level, a sIL-2Ra:IL-2 ratio, a TNFα level, a TNFRI level, a TNFRI:TNFα ratio, and/or a Neutrophil:Lymphocyte ratio (NLR).

In another aspect, the present disclosure provides an assay for measuring a complexed sgp130-sIL-6R.

4. BRIEF DESCRIPTION OF THE DRAWINGS

Figure 5A:
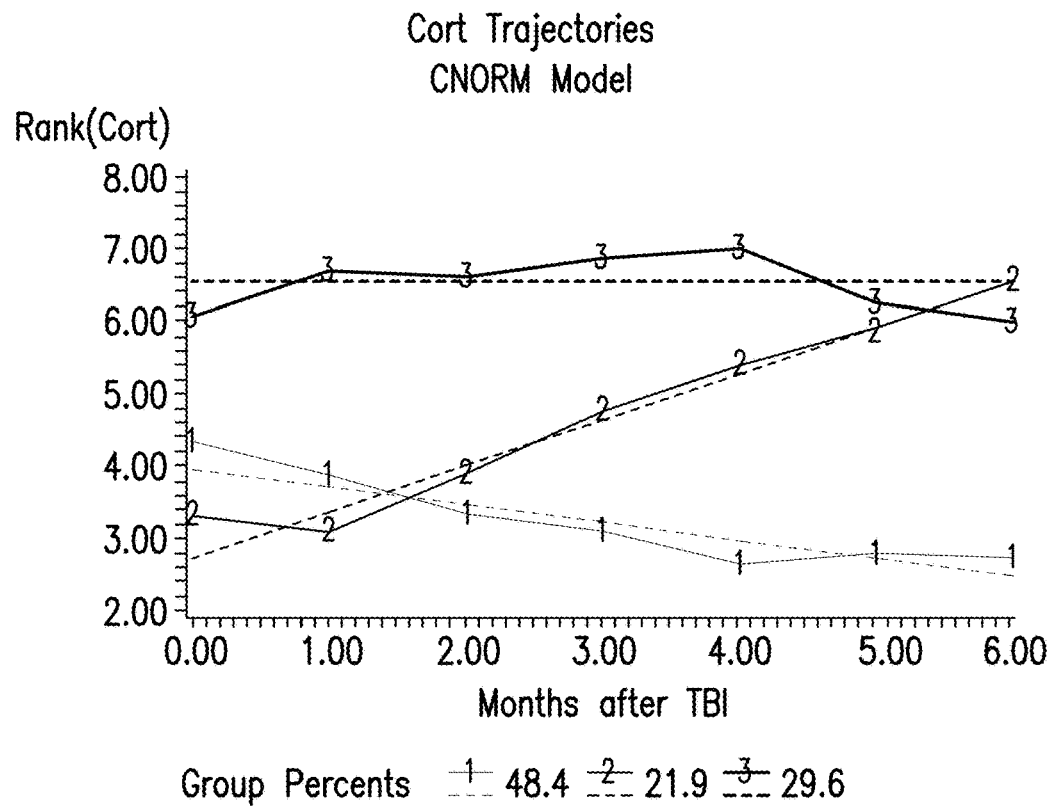
Figure 5B:
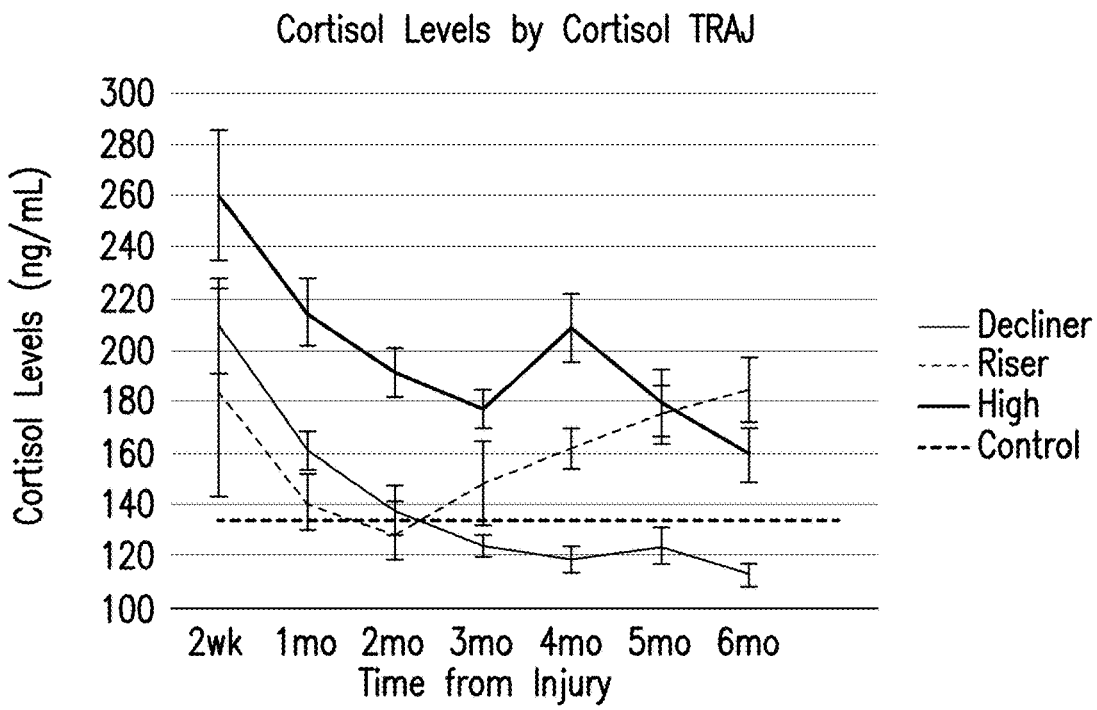

FIGS. 5A-5B provide HPA effects on chronic IL-6 trans-signaling after TBI, as measured by cort trajectories (5A) and cortisol levels by cortisol trajectory group membership (TRAJ) (5B).

Figure 6:
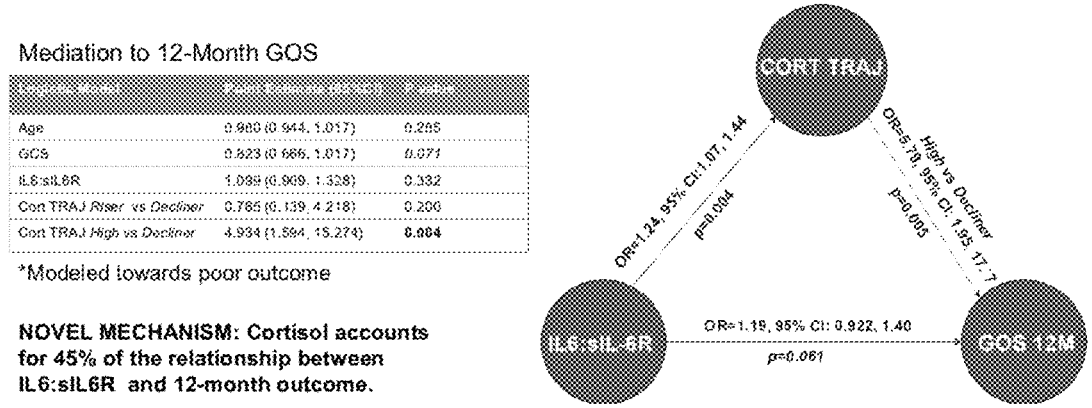

FIG. 6 provides mediation to 12-month Glasgow Outcome Scale (GOS) showing that chronic hypothalamic-pituitary-adrenal (HPA) axis regulated sIL-6R signaling impacts global outcome.

Figure 7:
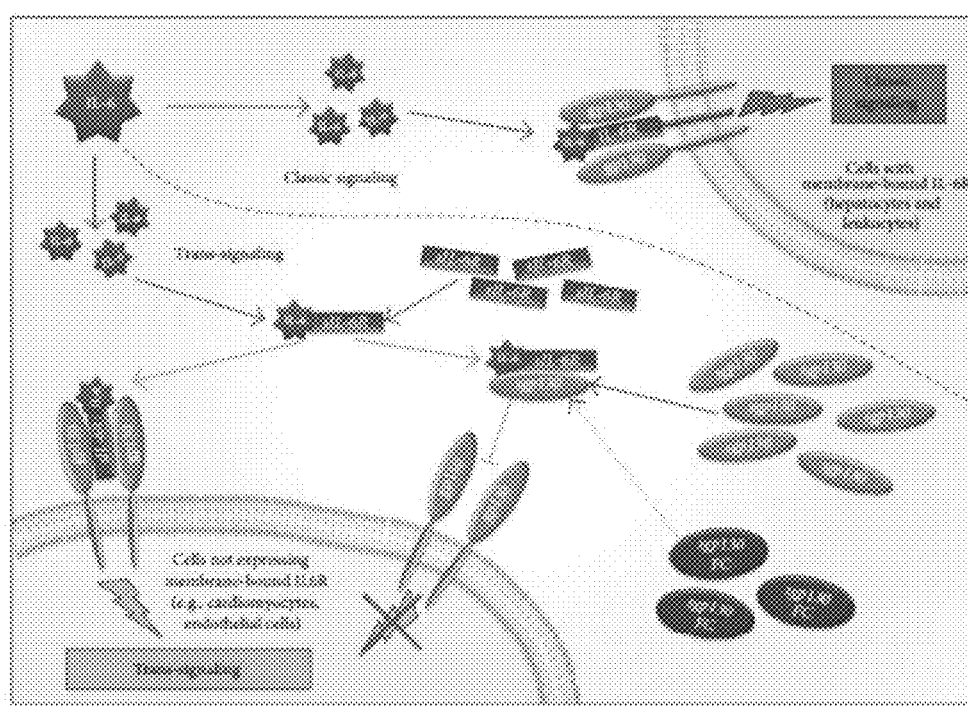

FIG. 7 depicts a scheme of IL-6/sIL-6R complex signaling.

Figure 8:
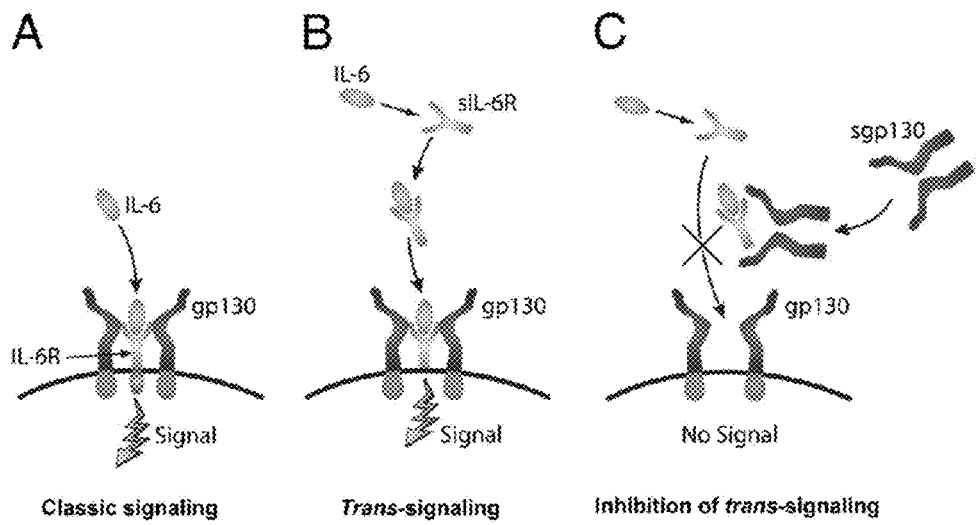

FIG. 8 depicts a scheme of IL-6 and IL-6R signaling.

Figure 9:
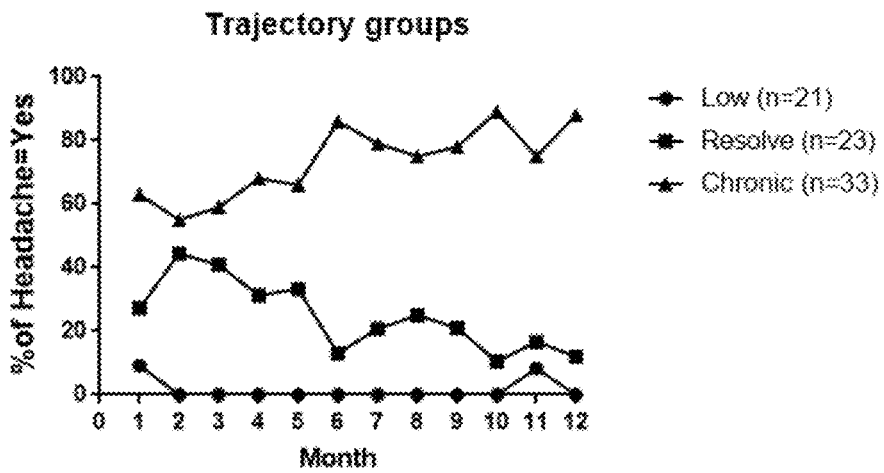

FIG. 9 provides longitudinal post-traumatic headache (PTH) profile analysis for different groups derived through group based trajectory analysis.

Figure 10:
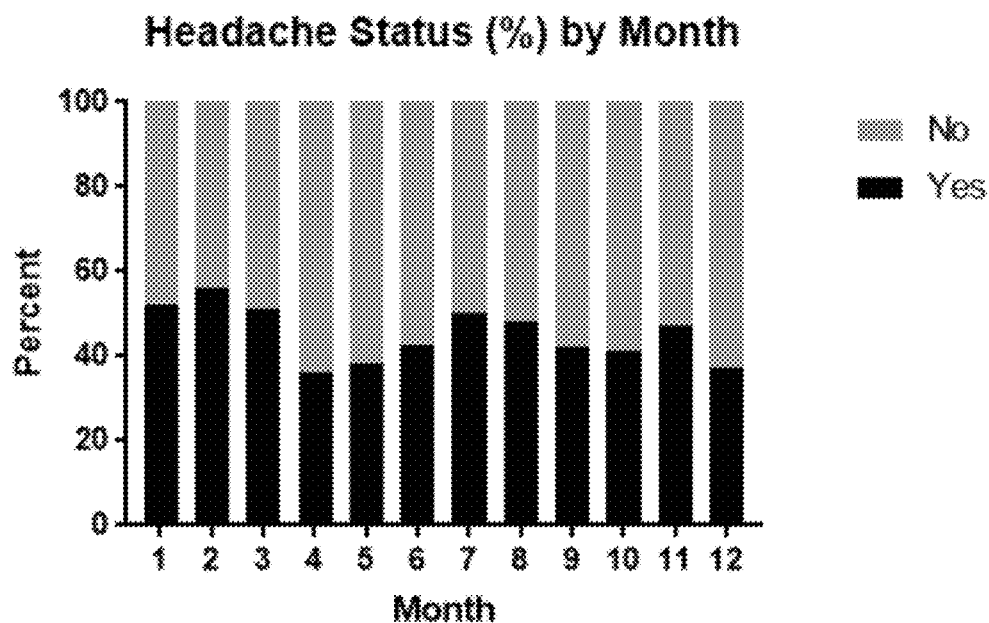

FIG. 10 provides a bar figure showing headache status (%) by month

Figure 11:
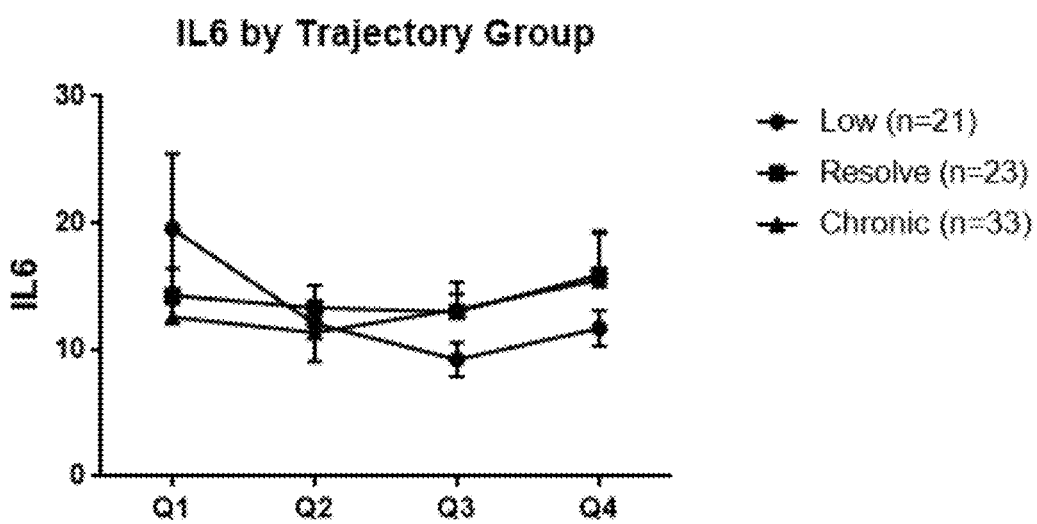

FIG. 11 provides IL-6 levels by post-traumatic headache (PTH) trajectory groups.

Figure 12:
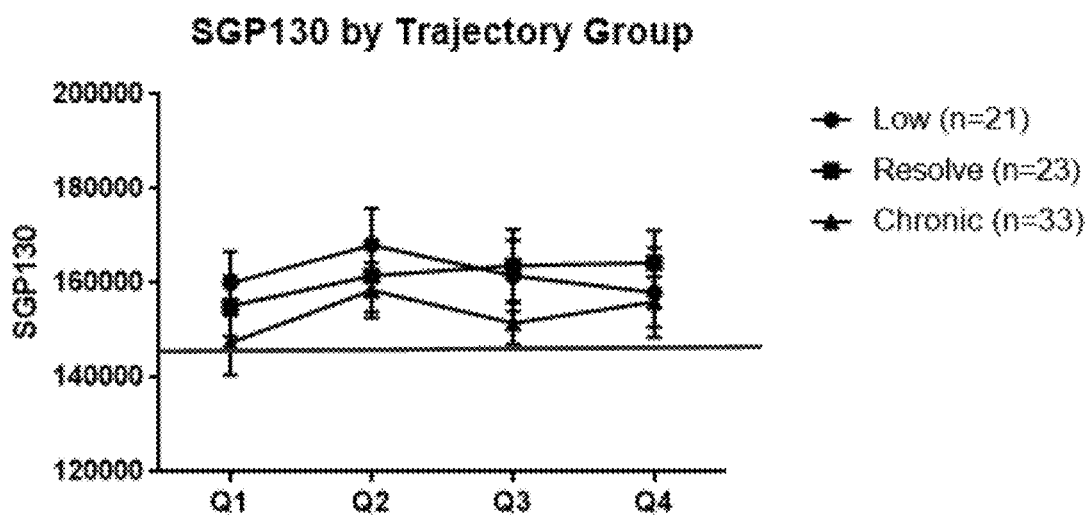

FIG. 12 provides SGP130 by post-traumatic headache (PTH) trajectory groups.

Figure 13:
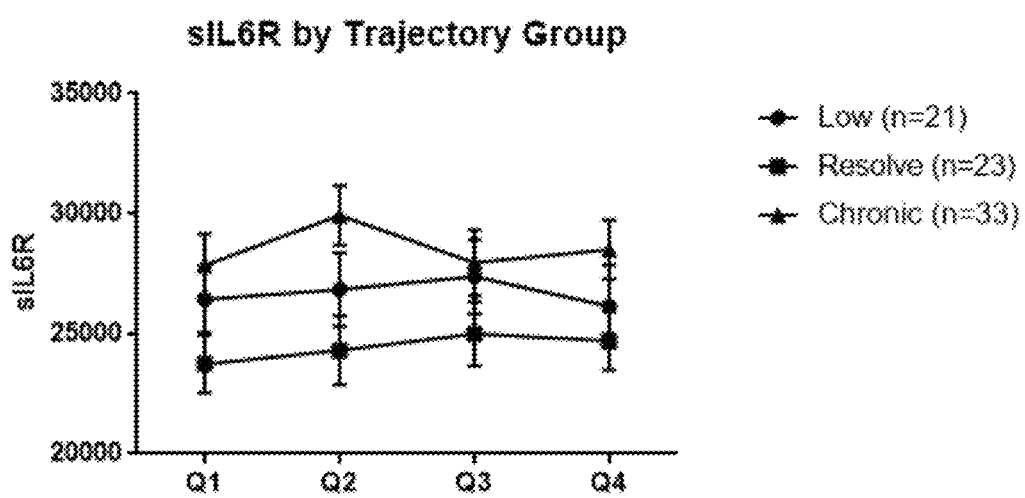

FIG. 13 provides sIL6R by post-traumatic headache (PTH) trajectory groups.

Figure 14:
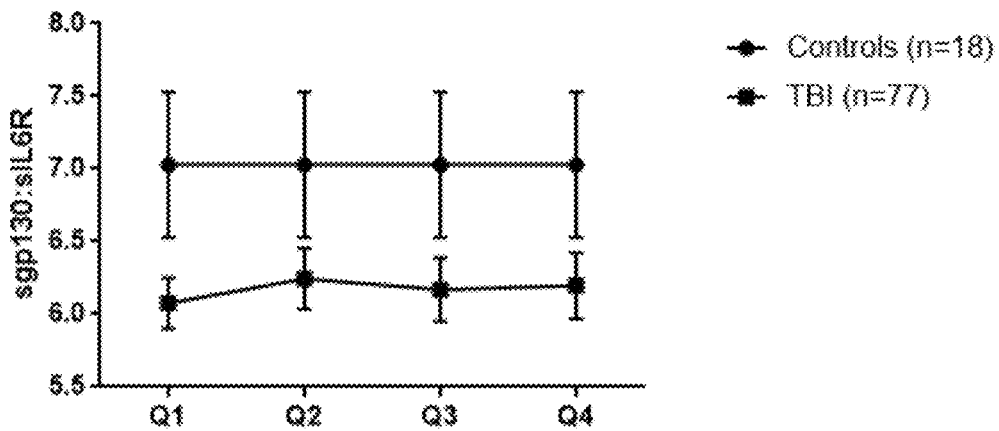

FIG. 14 provides sgp-130:sIL-6R ratios in control and TBI patients.

Figure 15:
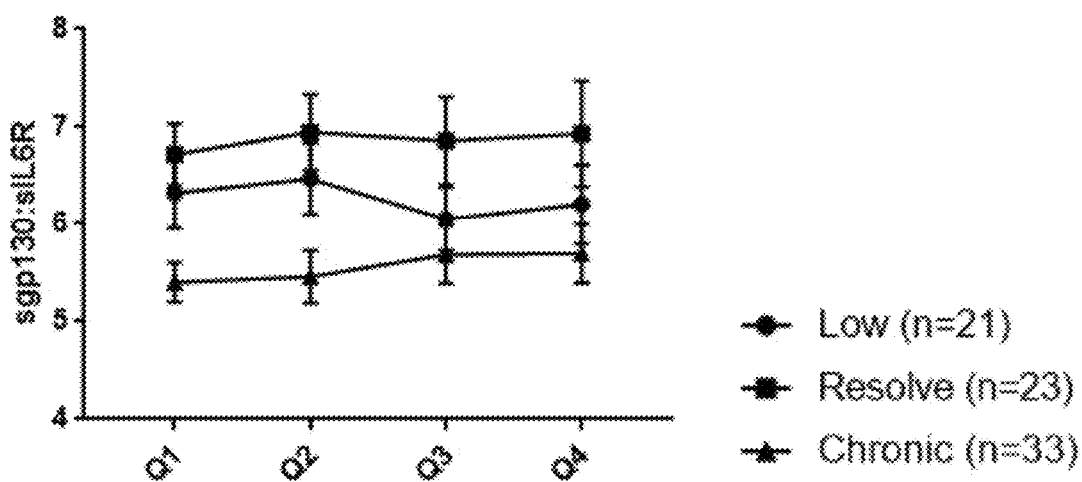

FIG. 15 provides sgp-130:sIL-6R ratios over time by post traumatic headache trajectory (TRAJ) groups.

Figure 16A:
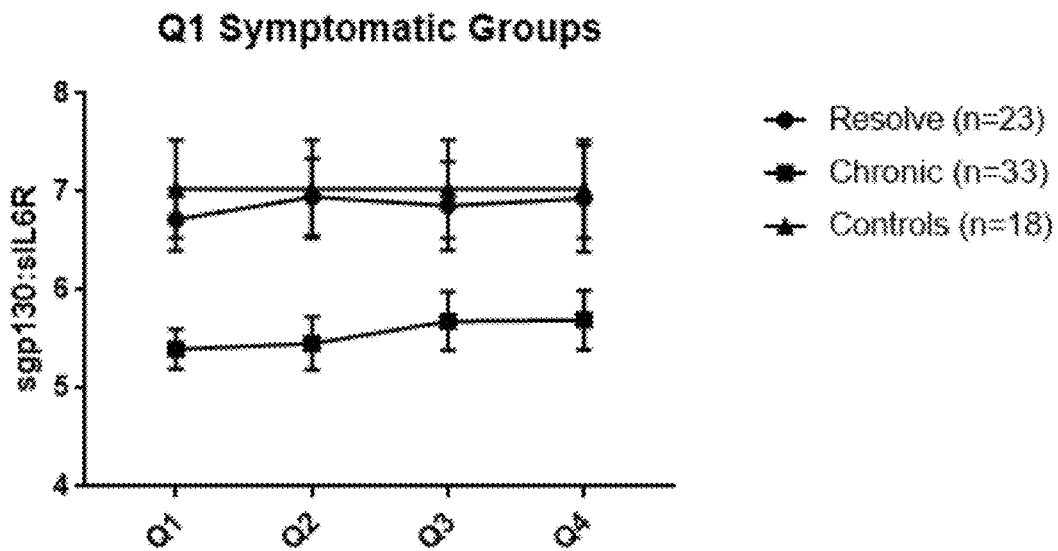

FIG. 16A shows the resolve group as SGP-130:sIL-6R ratios similar to uninjured controls.

Figure 16B:
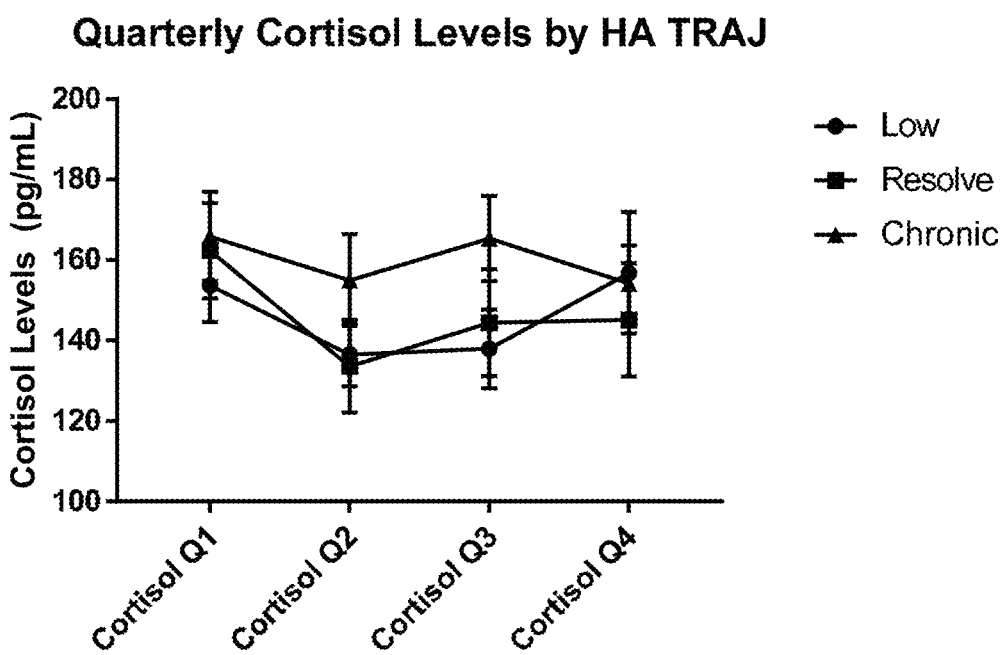

FIG. 16B provides the quarterly mean cortisol levels by HA TRAJ.

Figure 17:
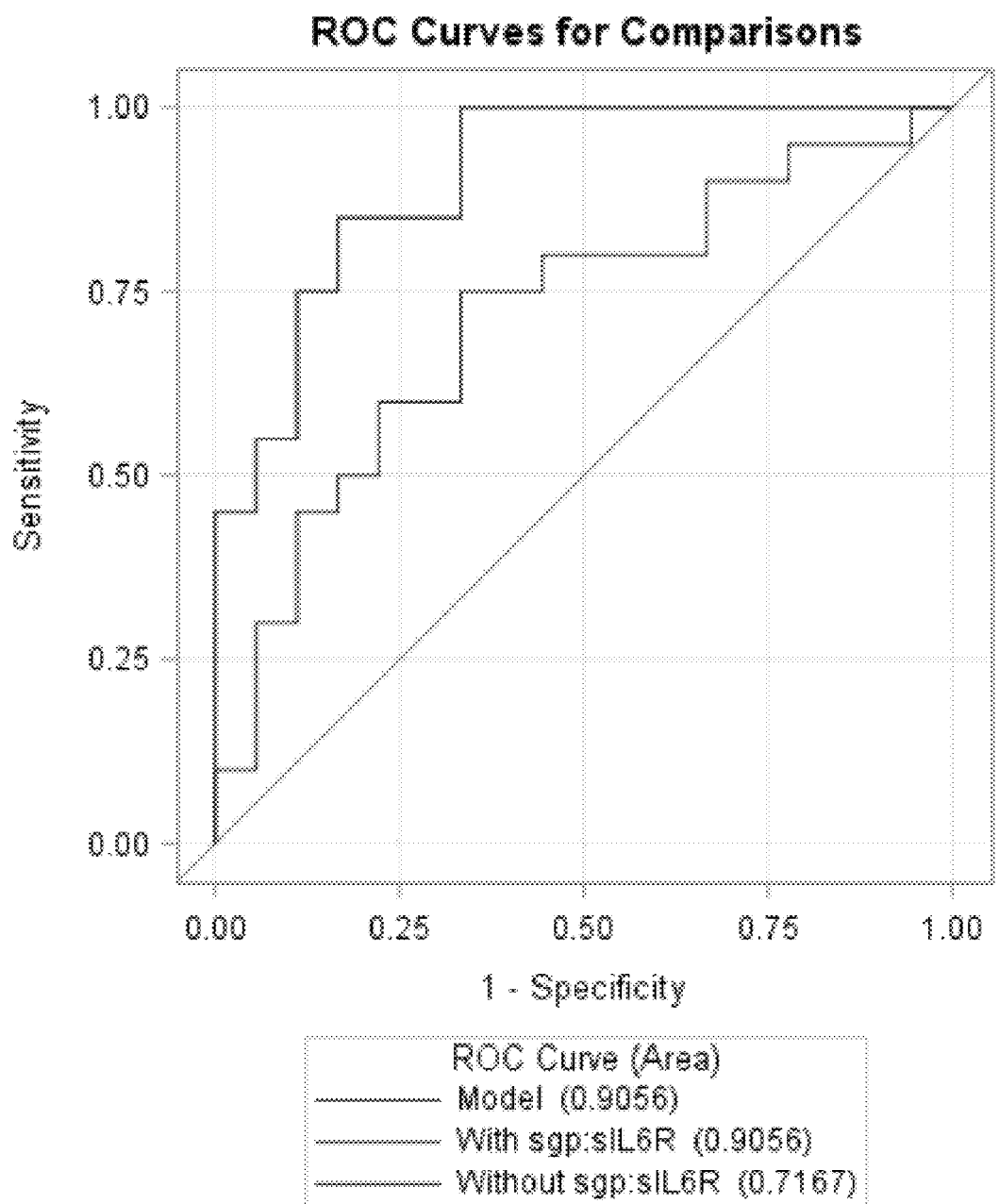

FIG. 17 provides an example headache prediction model. ROC curves for comparisons. Model with sgp130:sIL-6R with area under the curve (AUC) 0.91.

Figures 18, 19:
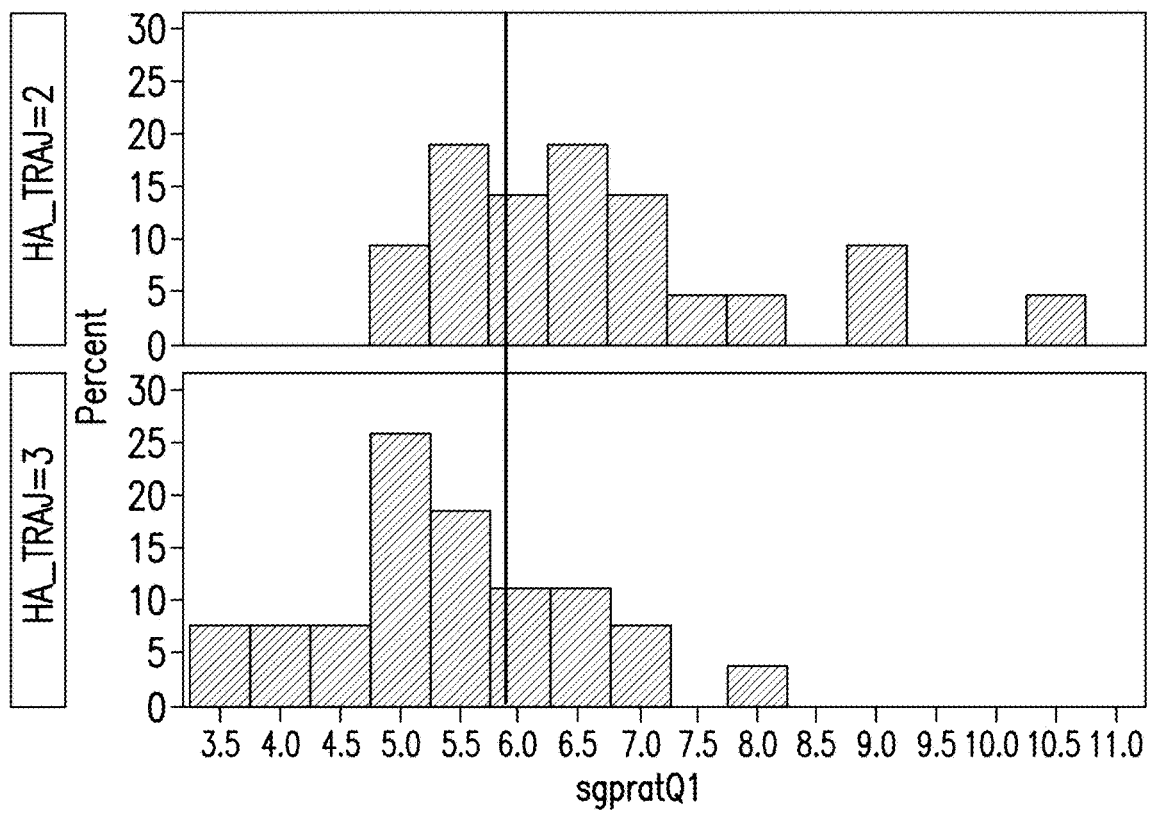

FIG. 18 provides Quarter 1 mean ratios.

FIG. 19 provides distribution of spg130:sIL6R ratio Quarter 1.

FIG. 20 provides CSF linear and log regression predicting a 6-month overall cognitive composite scores.

FIG. 21 provides linear regression for 6 and 12 months predicting overall cognitive composite scores.

FIG. 22 provides a logistic regression for 6 month overall cognitive impairment.

FIG. 23 provides a logistic regression for 12 month overall cognitive impairment.

Figure 24A:
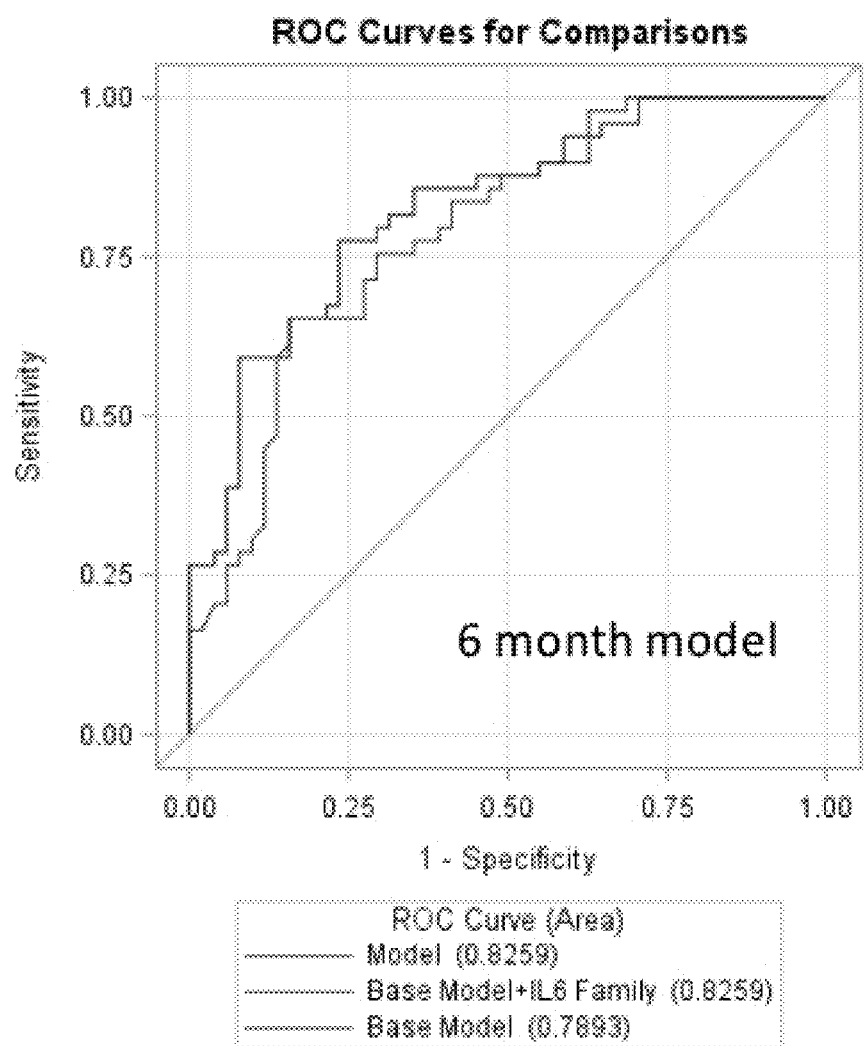
Figure 24B:
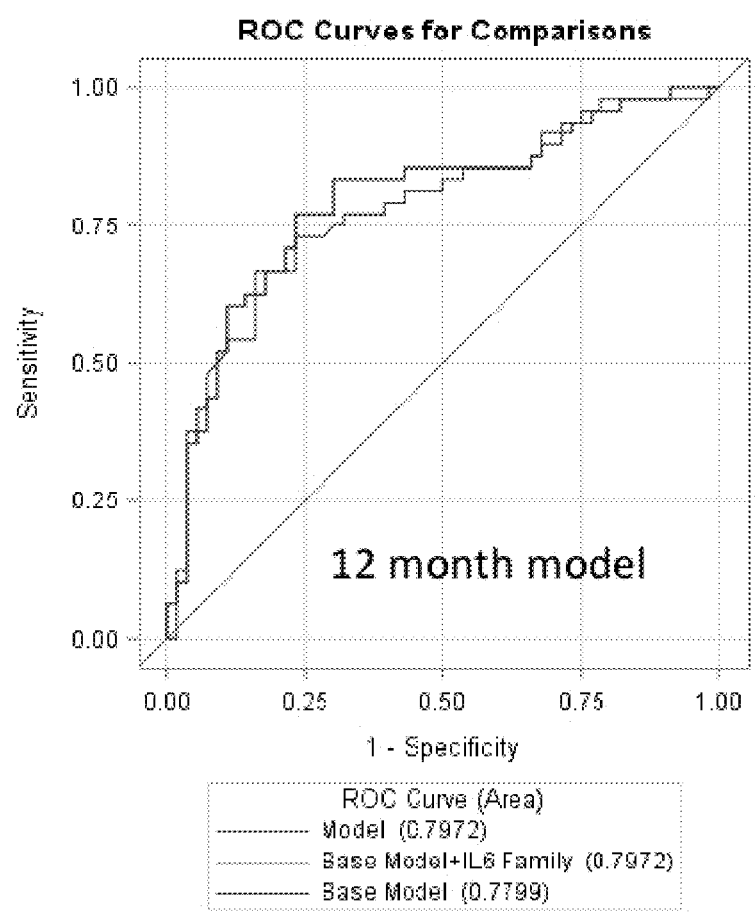

FIGS. 24A-24B provide ROC Curves for serum cognition impairment status for (24A) 6 months and (24B) 12 months.

Figure 25A:
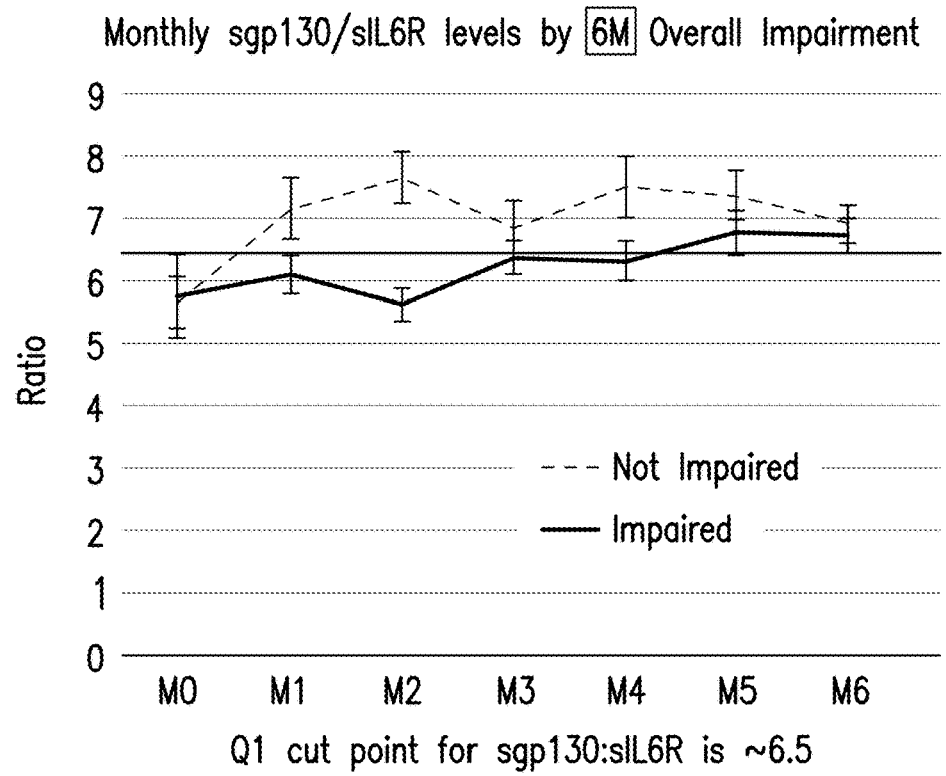
Figure 25B:
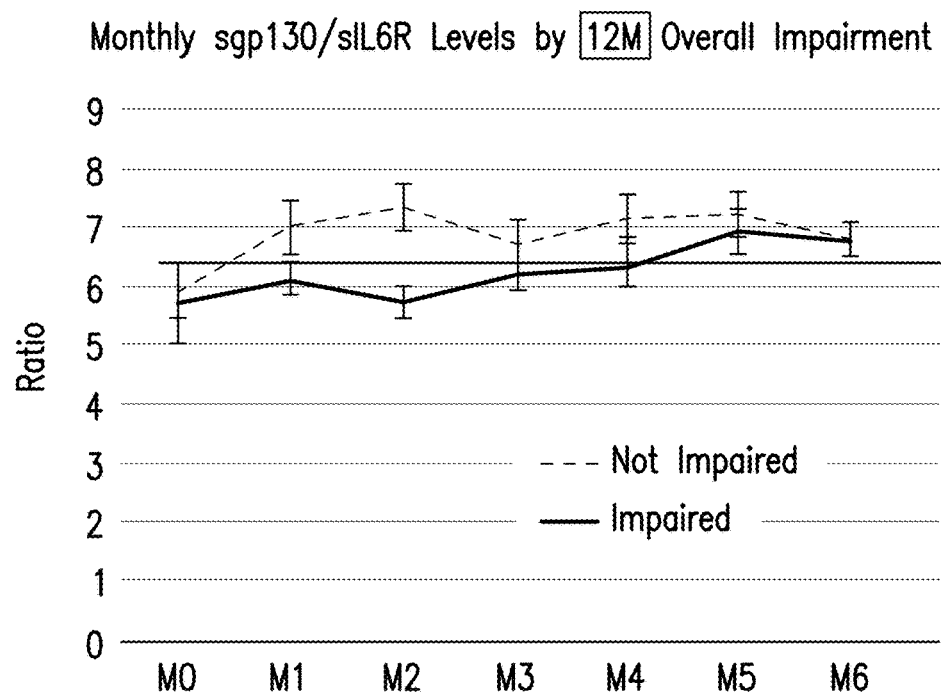
Figure 25C:
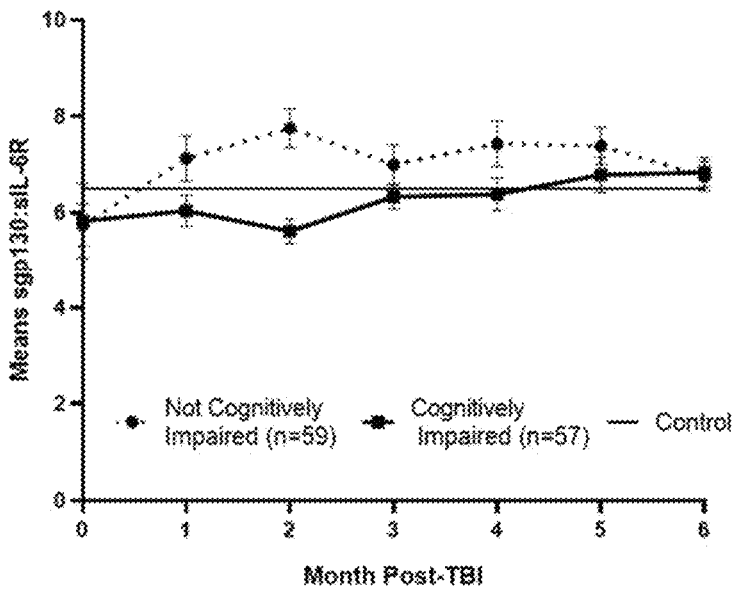

FIGS. 25A-25C provide serum sgp130:sIL6R ratio associations with cognition by 6-month (25A and 25C) and by 12-month (25B).

Figure 25D:
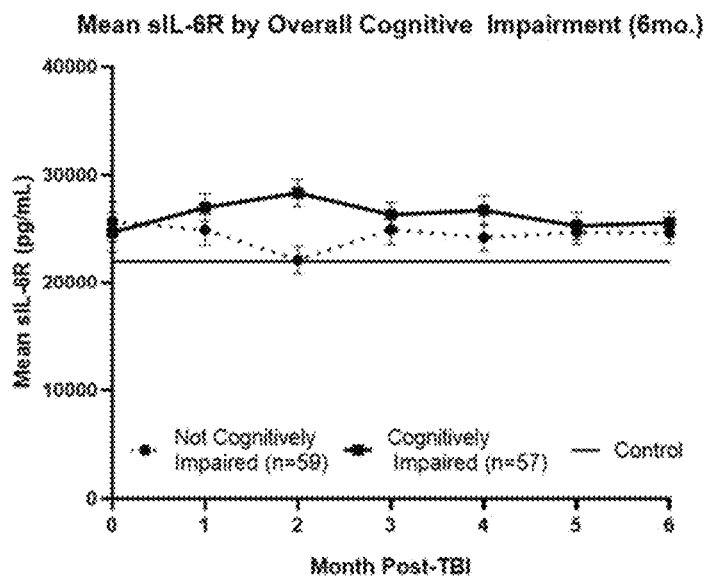

FIG. 25D provides the serum sIL-6R associations with cognitive impairment.

FIG. 26 provides IL-6 family biomarkers at months 0-3 predicting time until first seizure up to 1 year.

FIG. 27A provides cox proportional hazards regression showing how IL-6 family biomarkers at months 0-3 predicting time until first seizure to 1 year. Each row represents an independent model adjusted for Age, GCS, SDH, and Depressed Skull Fx (4 models run total). All biomarkers were standardized, so effect size is interpreted as risk per 1 std increase. Adjusted models have sample size of n=113.

FIG. 27B provides cox proportional hazards regression showing how IL-6 family biomarkers at mo0-6 predict time until first seizure to 3 yean.

Figure 28A:
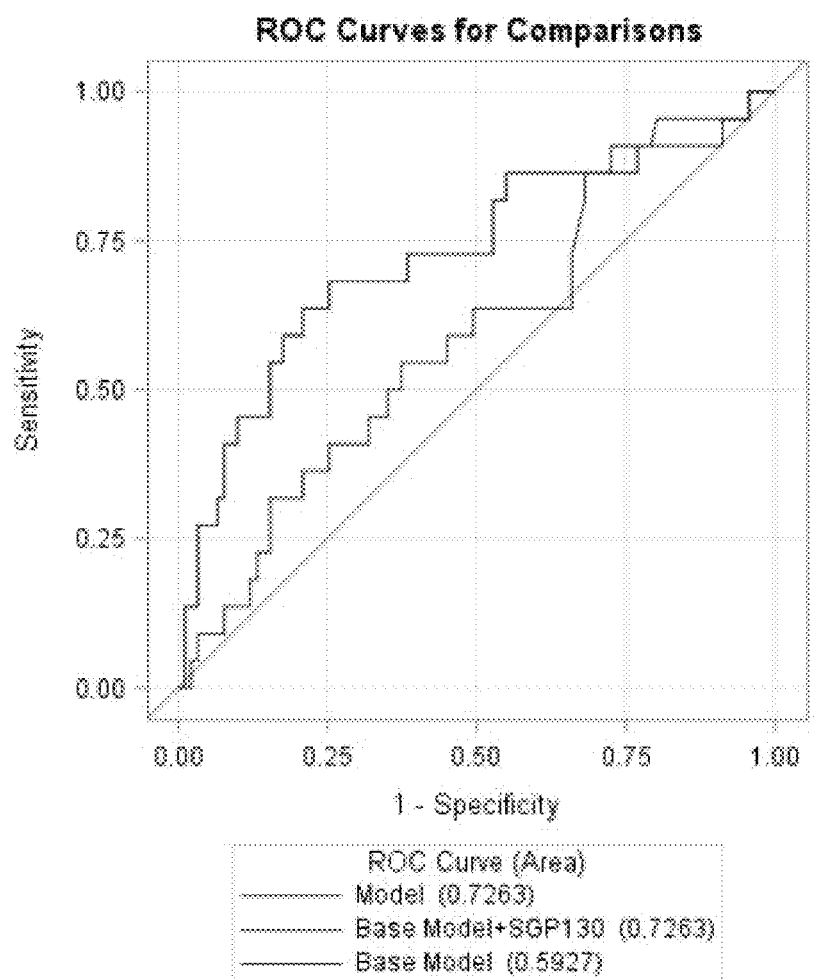

FIG. 28A provides the epilepsy prediction model. 1 year PTE (Y/N) logistic regression model, month 0-3 sgp130+ age, GCS compared to base model of age, GCS, SDH, and Depressed Skull Fx. p=0.054 for difference between curves.

Figures 28B, 28C:
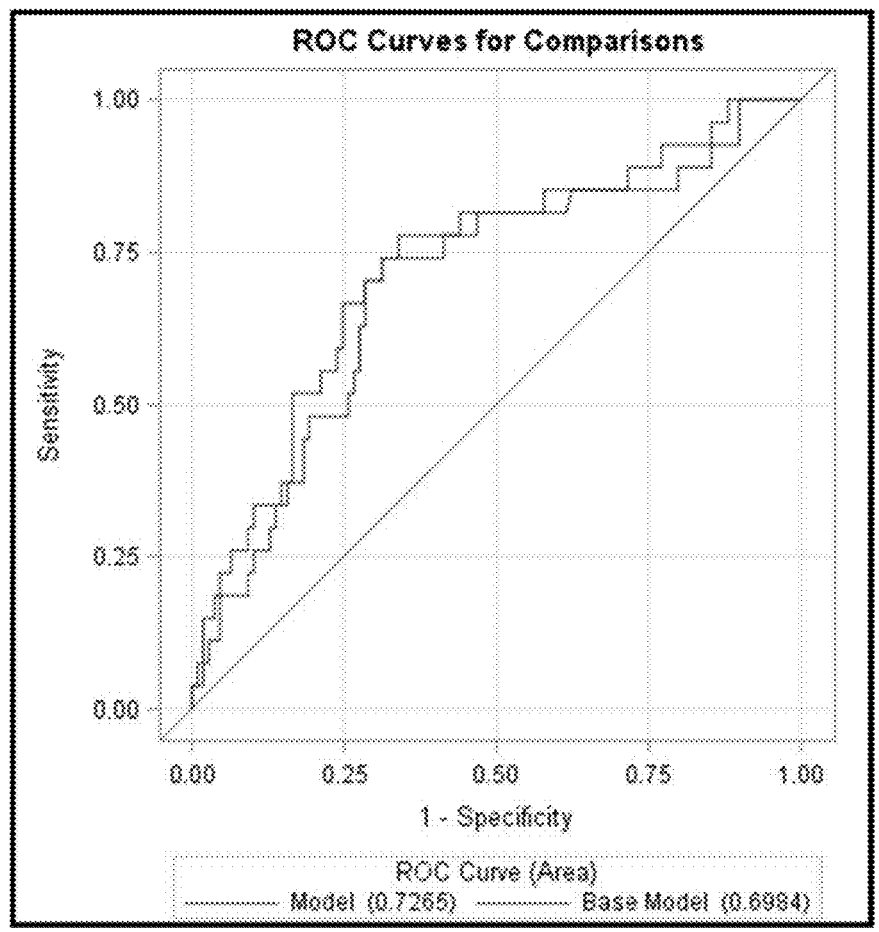

FIGS. 28B and C provide the epilepsy prediction model. P=0.0446 for difference between curves (28C).

Figure 29A:
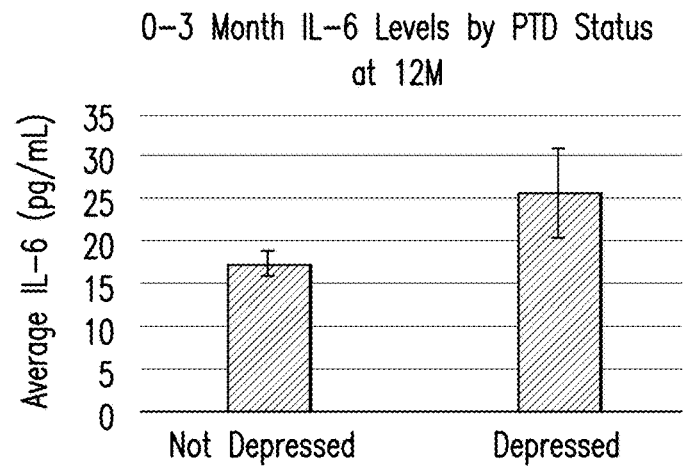
Figure 29B:
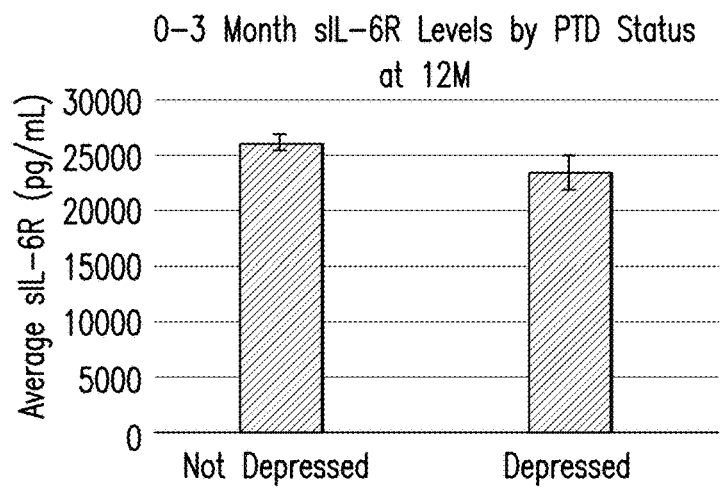
Figure 29C:
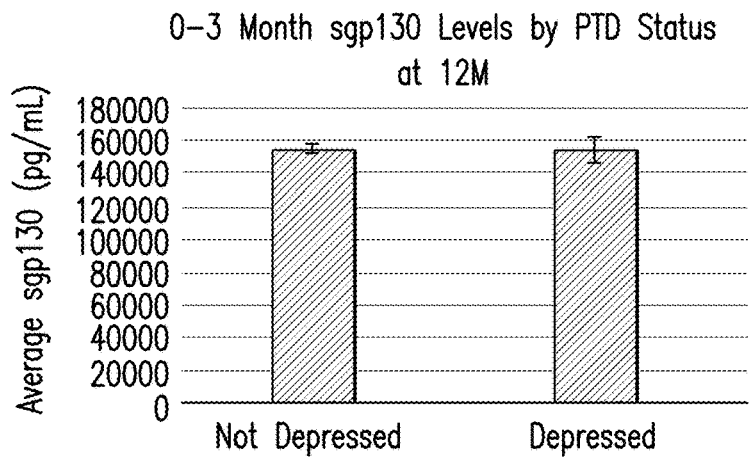

FIGS. 29A-29C provide IL-6 (29A), sIL-6R (29B), and sgp130 (29C) by 12 month PTD status.

FIG. 30 provides linear regression predicting PHQ-9 scores at 12-months.

FIG. 31 provides logistic regression predicting PHQ-9 impaired status at 12-months.

FIG. 32 provides linear regression predicting 12 month PHQ-9 total scores.

Figures 33, 34:
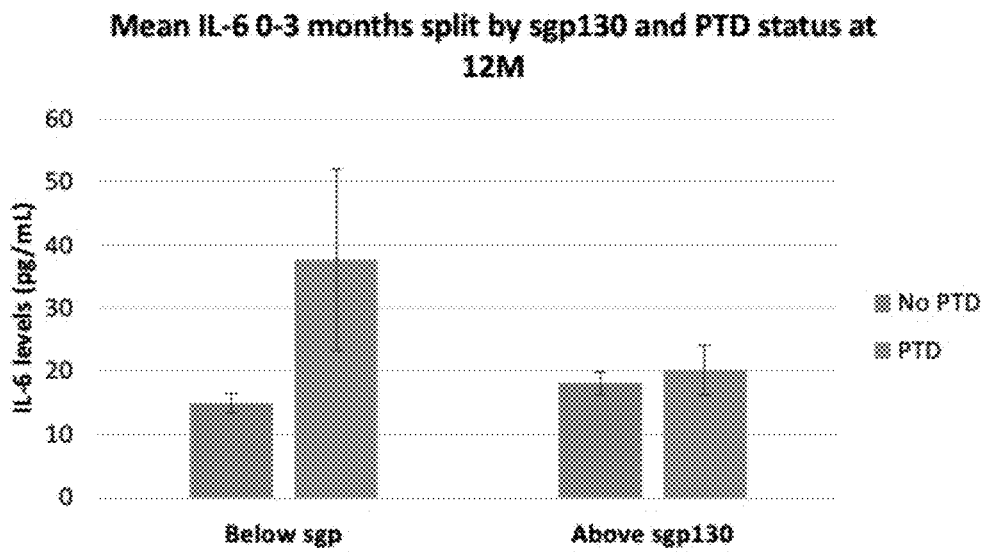

FIG. 33 provides mean IL-6 at 0-3 months stratified by sgp130 and PTD status at 12 months.

FIG. 34 provides linear regression predicting 12 month PHQ-9 total scores after removing people who had pre-morbid depression and reran the model for sensitivity analysis.

Figure 35:
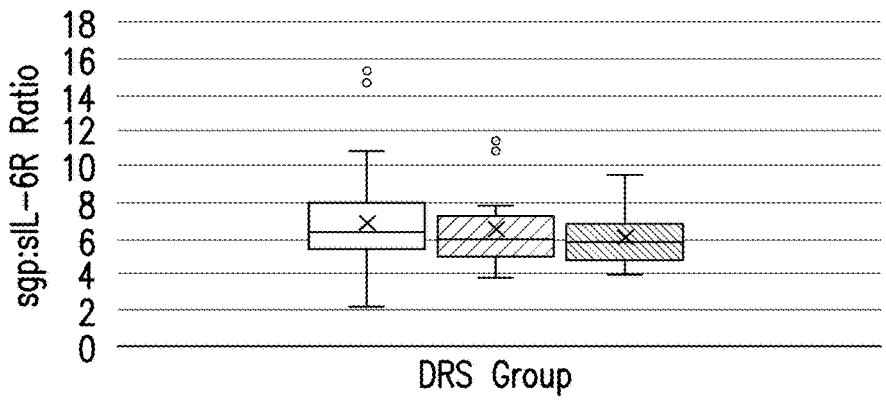

FIG. 35 provides median ratio levels graphed by 12 month DRS scores.

Figure 36A:
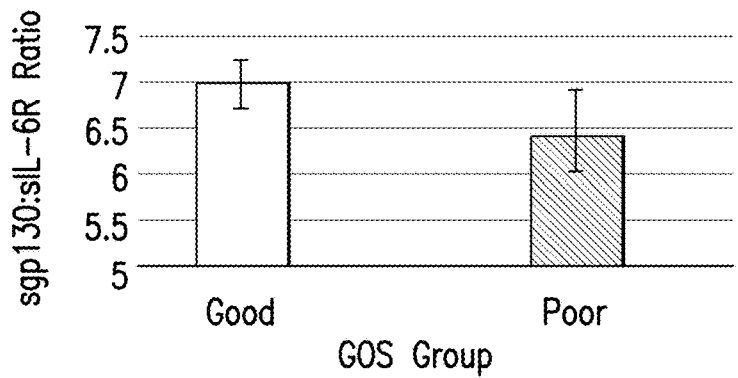
Figure 36B:
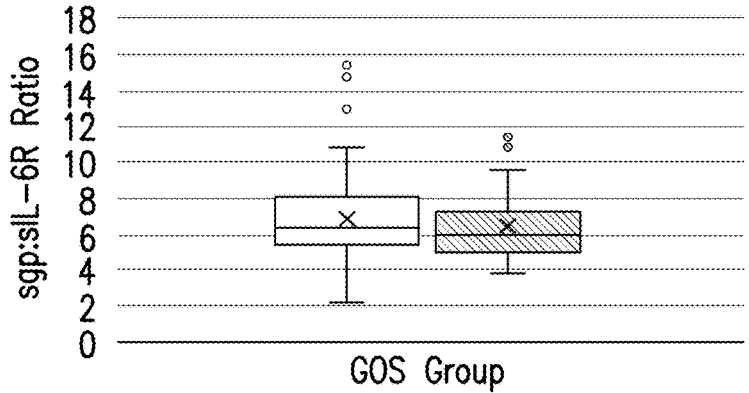

FIGS. 36A-36B provide the mean (36A) and median ratio (36B) levels graphed by 12 month GOS scores.

Figure 37:
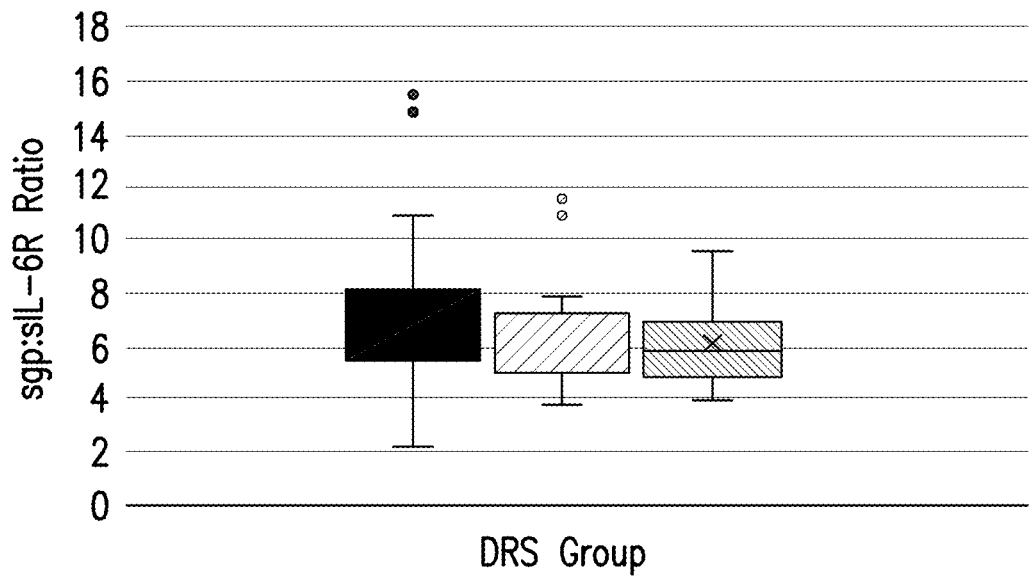

FIG. 37 provides the median ratio levels by 12 month DRS scores.

Figure 38:
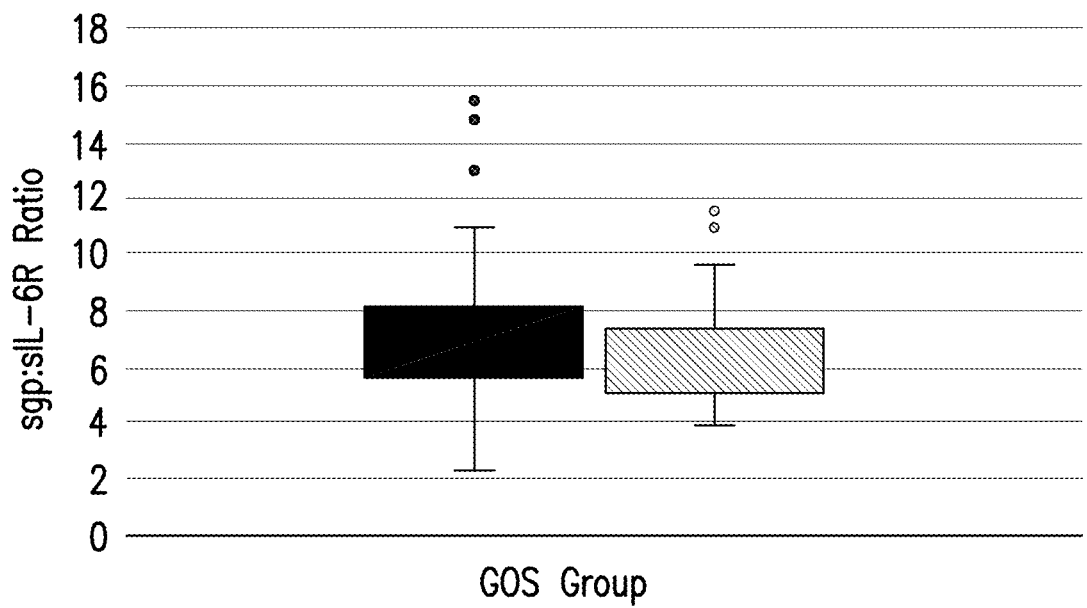

FIG. 38 provides the median ratio levels by 12 month DRS scores.

Figure 39A:
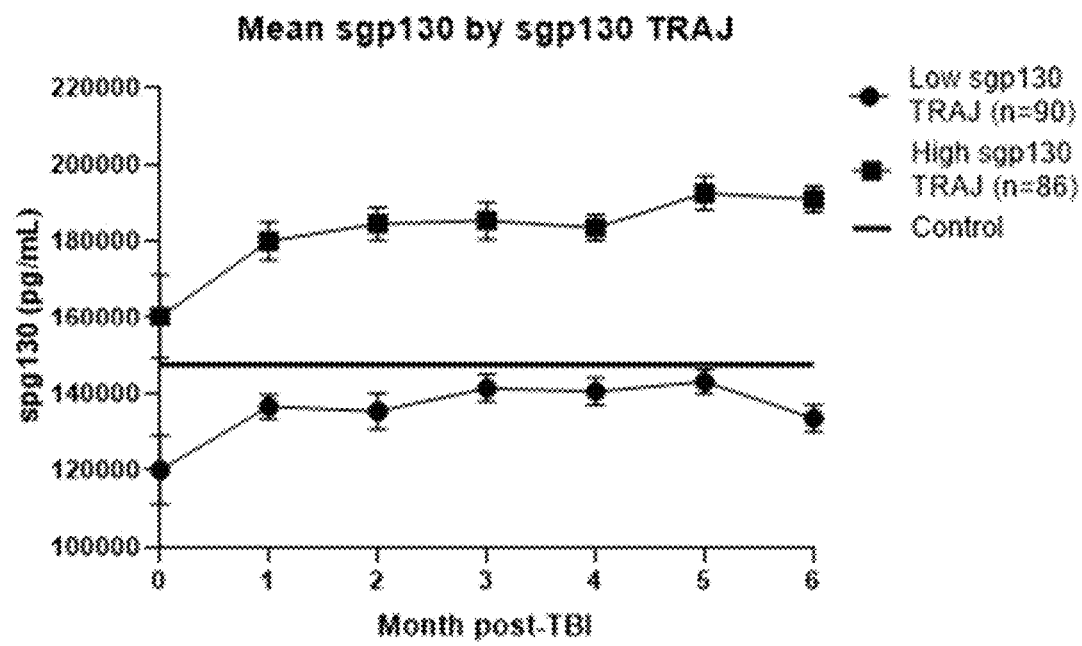
Figure 39B:
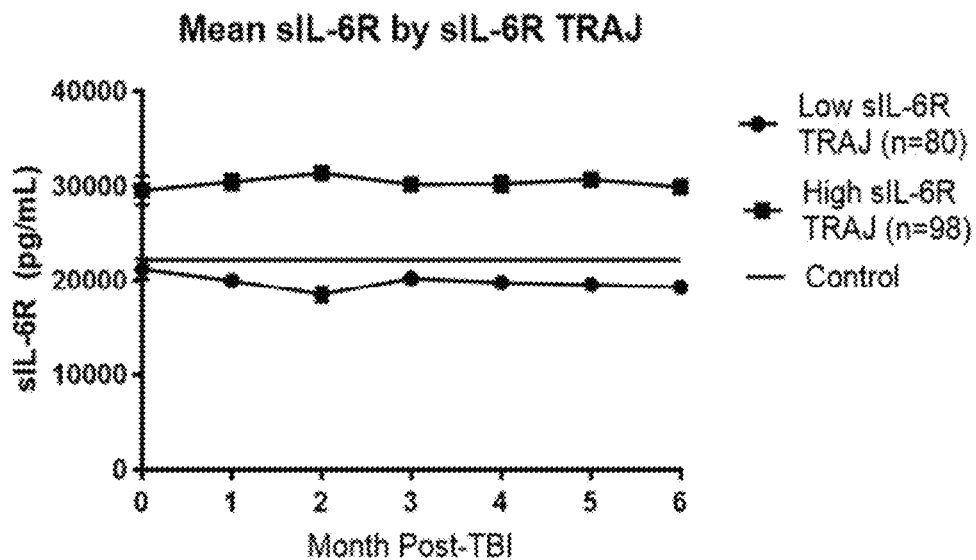

FIGS. 39A-39B provide group-based TRAJ analyses for sgp130 (39A) & sIL-6R (39B).

FIG. 40 provides a group-based TRAJ analysis for sgp130:sIL-6R ratio.

FIG. 41 provides acute and chronic impairment event rate (% of TRAJ).

Figure 42:
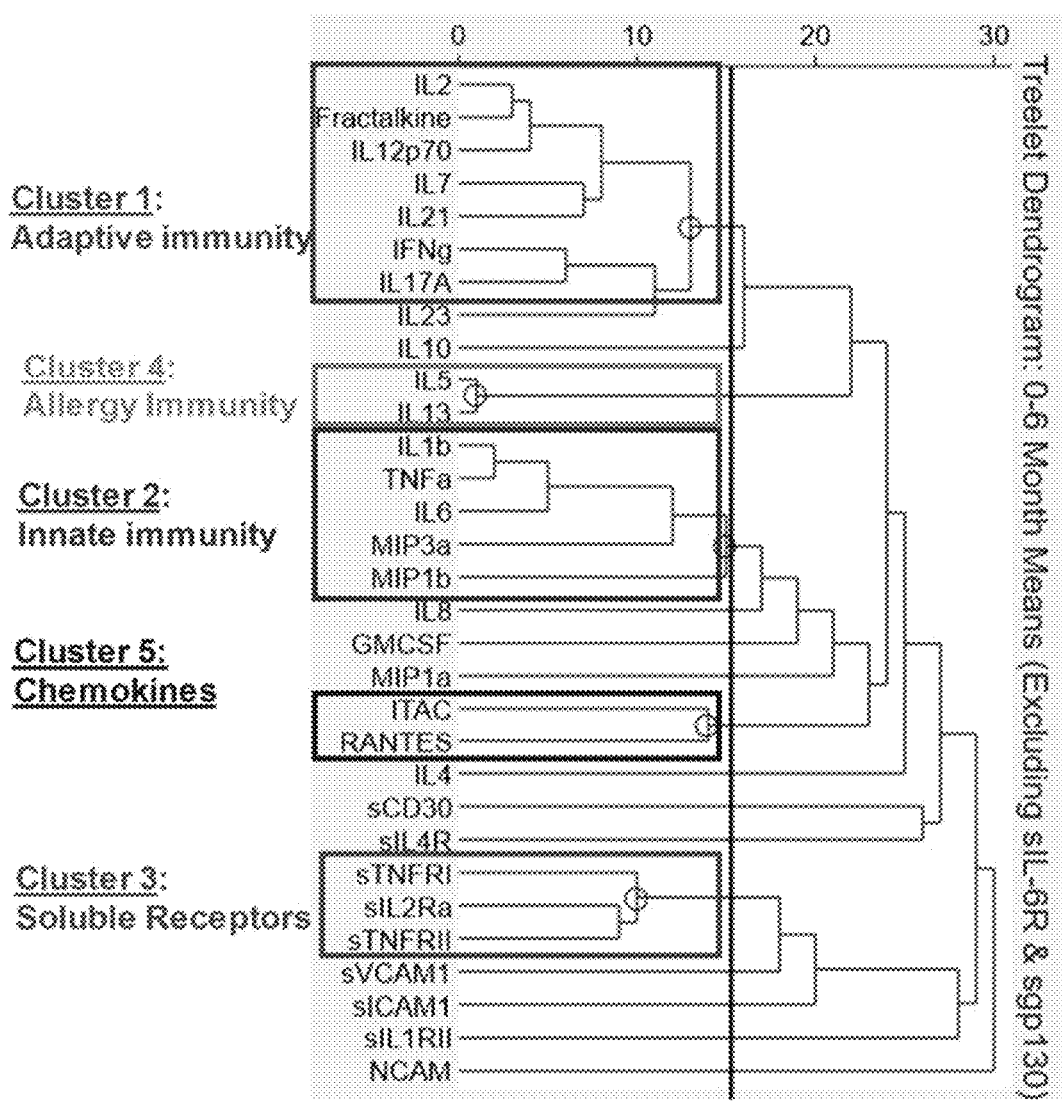

FIG. 42 provides an example chronic inflammation treelet transformation analysis.

Figure 43A:
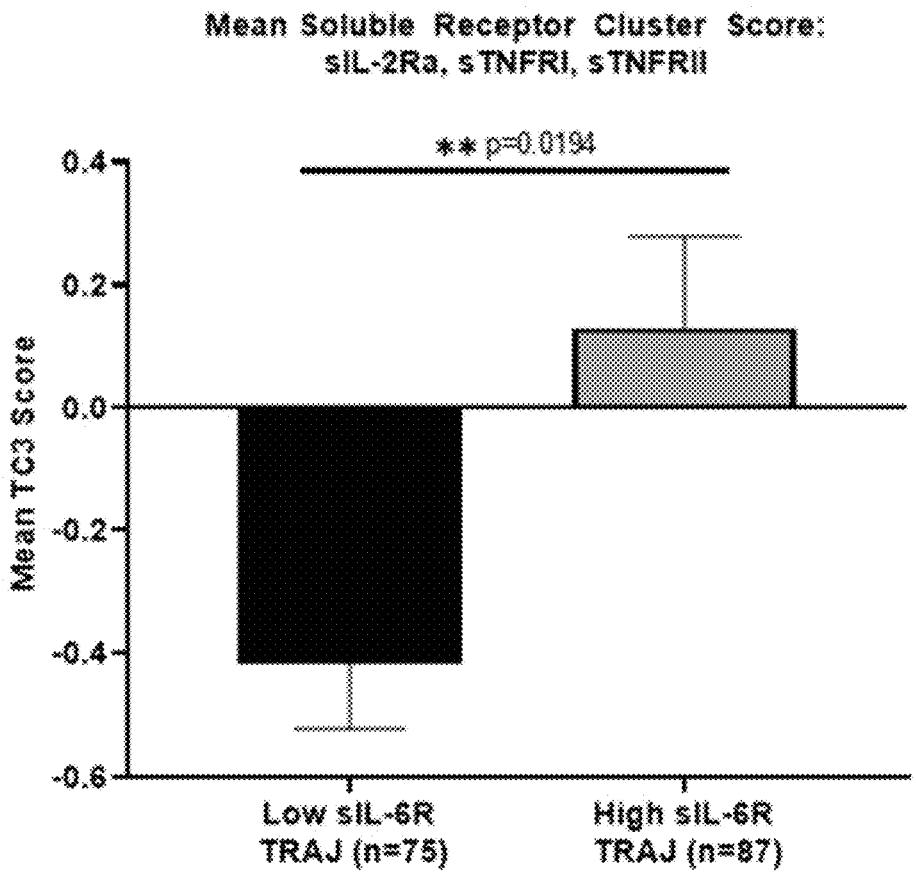
Figure 43B:
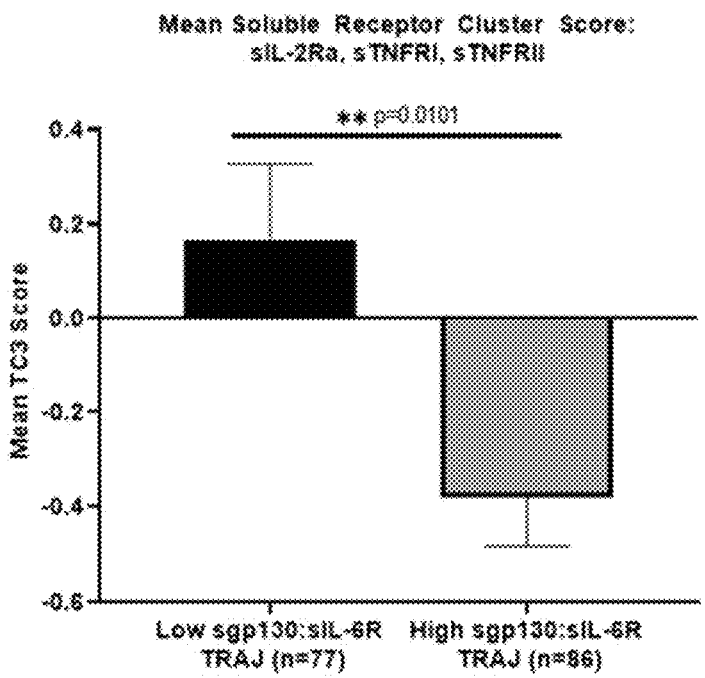

FIGS. 43A-43B provide mean TC3 scores for sIL-6R (43A) and sgp130:sIL-6R (43B) TRAJ groups.

Figure 43C:
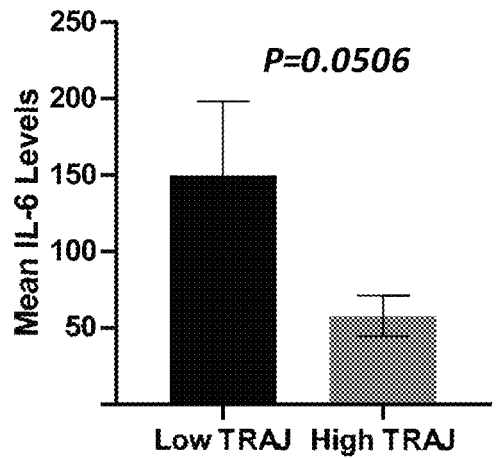
Figure 43D:
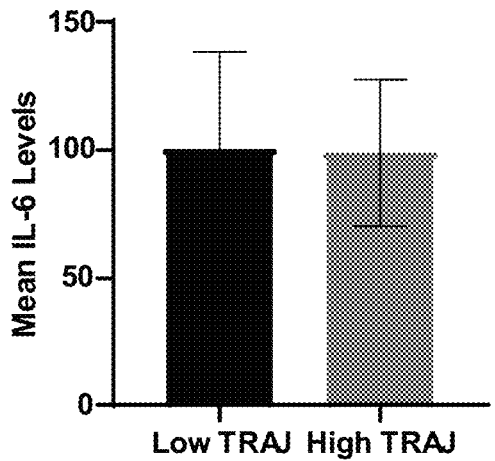

FIGS. 43C-43D provide IL-6 levels by sIL-6R TRAJ Group (43C) and IL-6 levels by sGP130:sIL-6R TRAJ Group (43D).

Figure 43E:
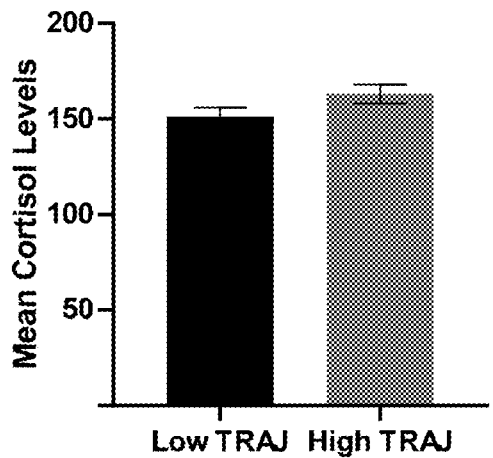
Figure 43F:
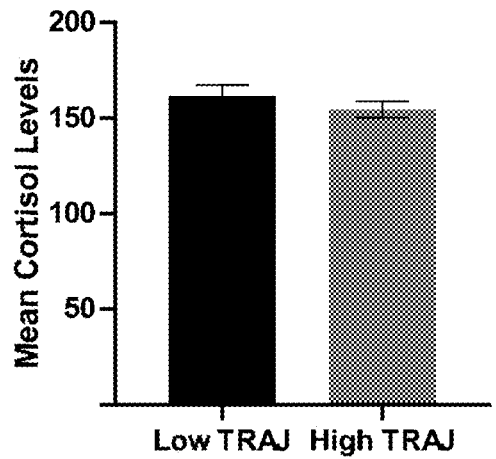

FIGS. 43E-43F provide 0-6 month CORT by sIL-6R TRAJ (43E) and/or sGP130:sIL-6R TRAJ (43F).

Figure 44:
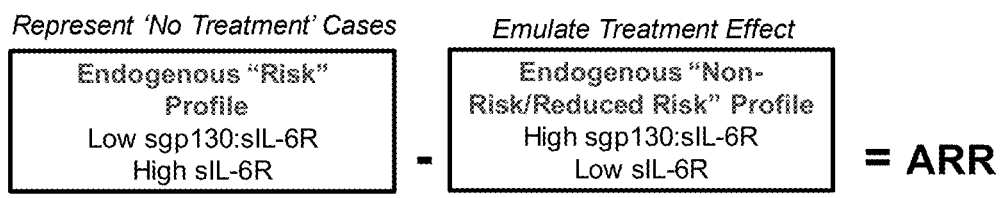

FIG. 44 depicts the calculation of ARR.

Figure 45:
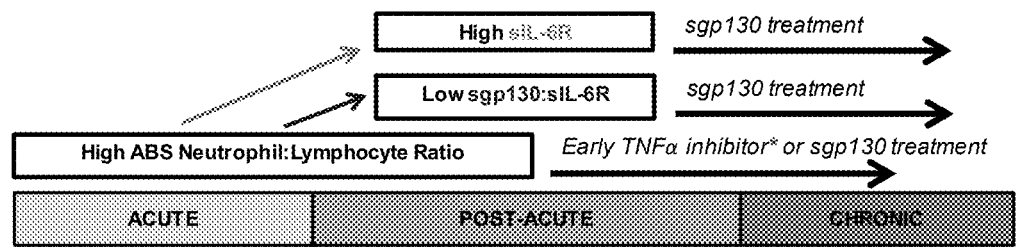

FIG. 45 depicts an example temporal screening scheme for the clinical trial planning.

FIGS. 46A-46B provide sgp130 (46A) and sIL-6R (46B) concentrations for low and high NLR TRAJ groups.

FIG. 46C provides concordance analysis showing acute immune cell TRAJ group membership maps well to sIL-6R group membership and is a good early proxy for chronic soluble IL-6 receptor states.

Figure 47A:
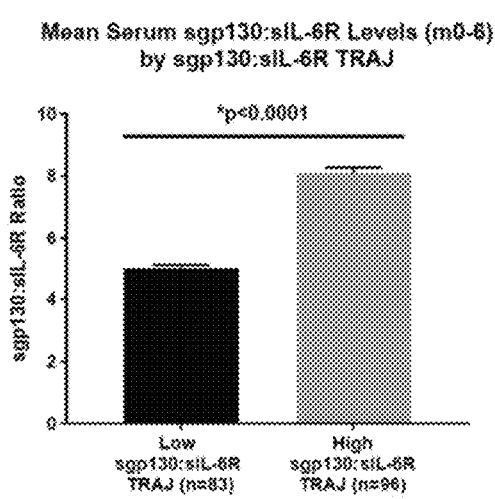
Figure 47B:
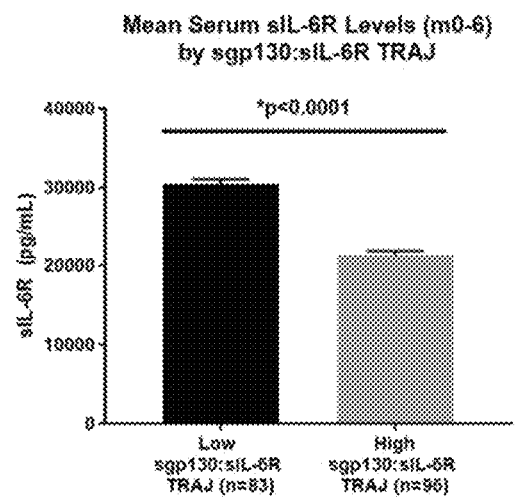
Figure 47C:
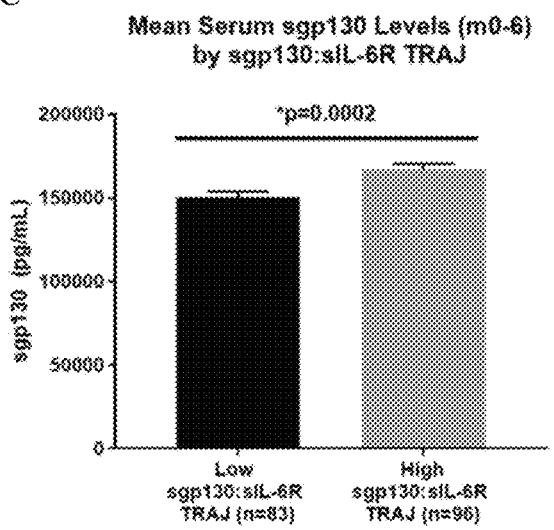
Figure 47D:
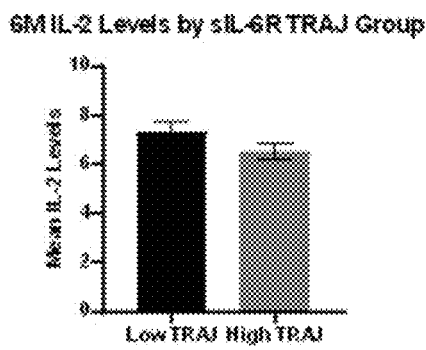
Figure 47E:
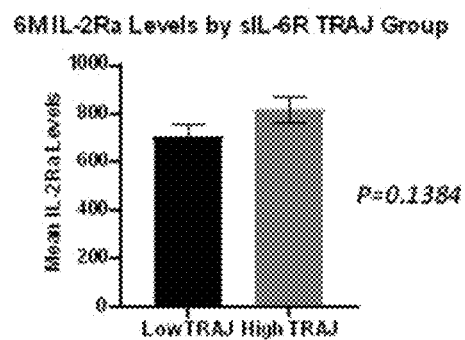
Figure 47F:
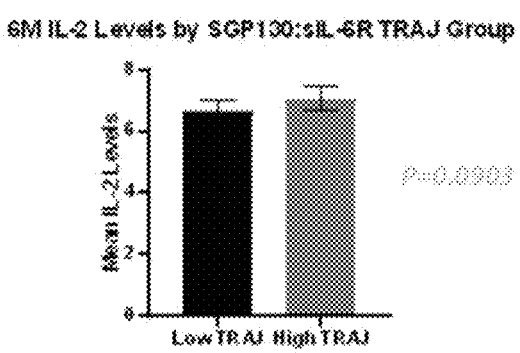
Figure 47G:
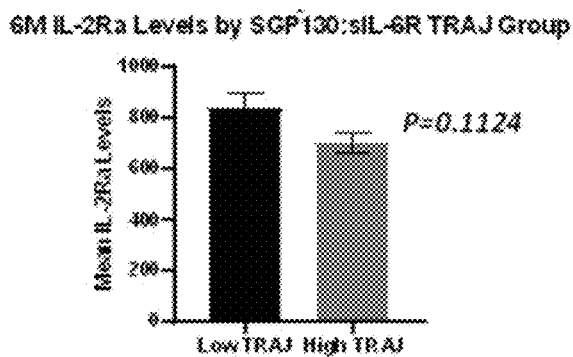

FIGS. 47A-47C provide serum sgp130:sIL-6R ratio (47A), sIL-6R (47B) and sgp130 levels (47C) for both low and high sgp130:sIL-6R TRAJ groups.

FIGS. 47D-47L provide 6-month IL-2 levels by sIL-6R TRAJ group membership (47D); 6-month IL-2Ra levels by sIL-6R TRAJ group membership (47E); 6-month IL-2 levels by sgp130:sIL-6R TRAJ group membership (47F); 6-month IL-2Ra levels by sgp130:sIL-6R TRAJ group membership (47G); months 0-6 sIL-2R/IL2 ratio by sIL-6R TRAJ group membership (47H); 6-month TNFα levels by sIL-6R TRAJ group membership (47I), 6-month TNFα levels by sgp130:sIL-6R TRAJ group membership (47J); 6-month TNFRI levels by sIL-6R TRAJ group membership (47K); 6 month TNFRI levels by sgp130:sIL-6R TRAJ group membership (47L).

Figure 48:
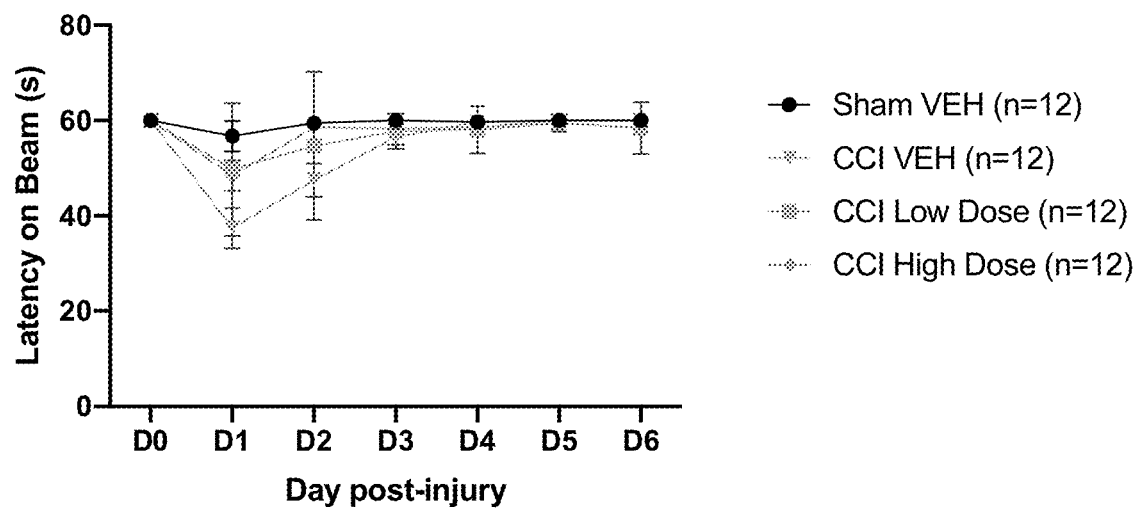

FIG. 48 provides beam balance latency analysis of CCI rats with different treatments. Two-way repeated measure ANOVA: Interaction: p<0.0001; Day: p<0.0001; Treatment Group: p=0.0009; Subject: p=0.0983. Post-hoc Tukey's multiple comparisons were performed starting day 0.

Figure 49:
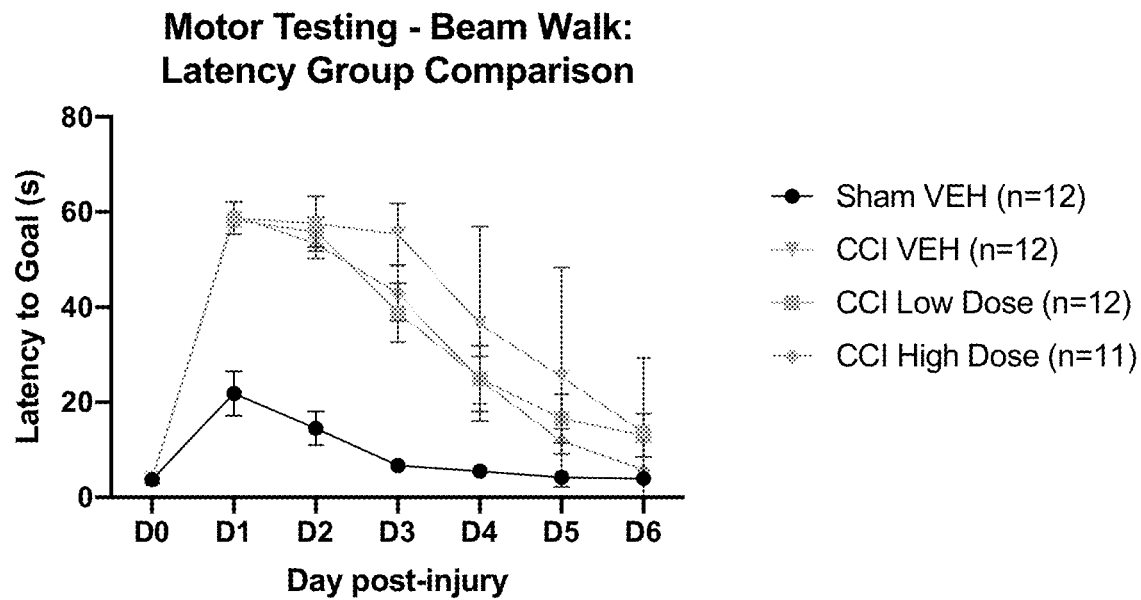

FIG. 49 provides beam walk latency analysis of CCI rats with different treatments. Two-Way Repeated Measure ANOVA: Interaction: p<0.0001; Day: p<0.0001; Treatment Group: p<0.0001; Subject: p<0.0001. Post-hoc Tukey's Multiple Comparisons were performed. These results may indicate only possible modest treatment effect on motor latency.

Figure 50:
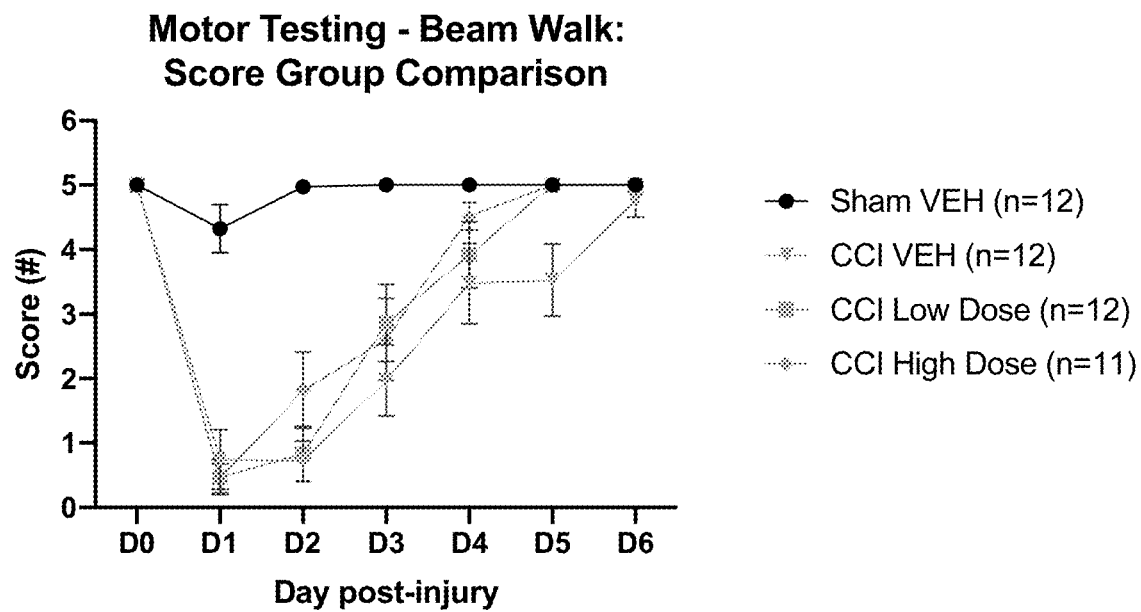

FIG. 50 provides beam walk scores of CCI rats with different treatments. Two-Way Repeated Measure ANOVA: Interaction: p<0.0001; Day: p<0.0001; Treatment Group: p<0.0001; Subject: p<0.0001. Post-hoc Tukey's Multiple Comparisons were performed. High dose CCI sgp130 group returns to baseline function 2 days sooner than CCI vehicle group.

Figure 51:
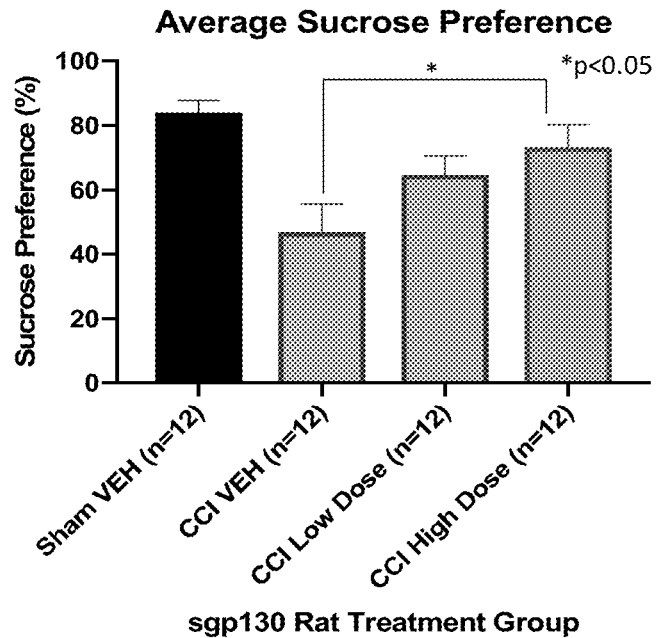

FIG. 51 provides in sucrose preference testing in CCI rats. ANOVA: p=0.0019. Pairwise comparisons were performed. CCI VEH vs. CCI Low Dose: p=0.1016; CCI VEH vs CCI High Dose: p=0.0291; CCI VEH vs. Sham: p=0.0007; CCI Low Dose vs. Sham: p=0.0105; CCI High Dose vs. Sham: p=0.1801. Particularly high dose SGP130 CCI improved preference for sucrose bottle to levels consistent with Sham.

Figure 52:
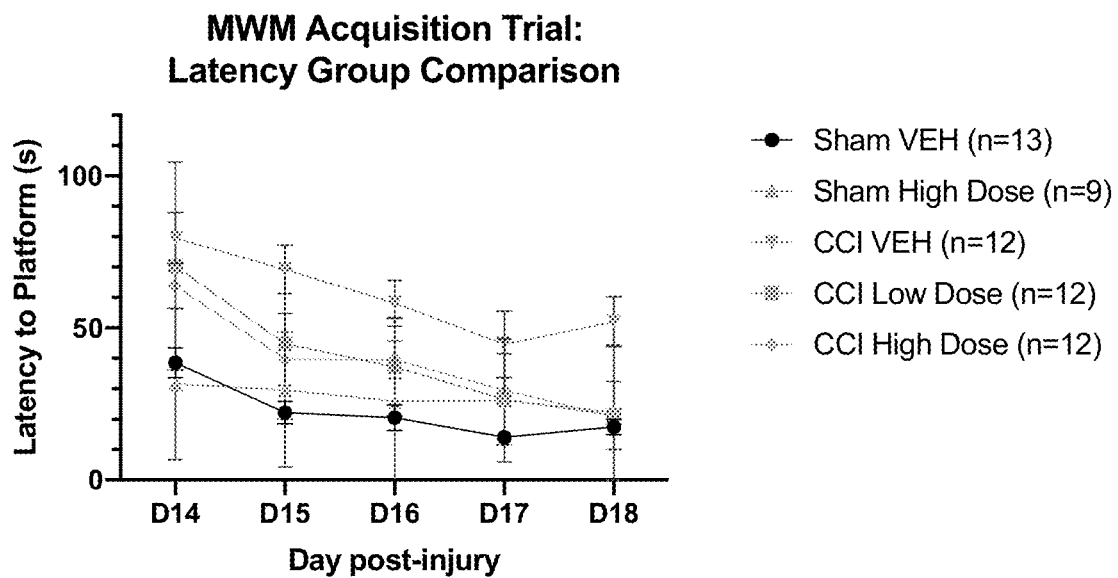

FIG. 52 provides the acquisition latency group comparison in CCI mice. Two-Way Repeated Measure ANOVA: Interaction: p=0.1676; Day: p<0.0001; Treatment Group: p<0.0001; Subject: p<0.0001). Post-hoc Tukey's Multiple Comparisons were performed. CCI VEH vs CCI Low Dose and CCI High Dose each with—significantly lower latencies than CCI vehicle.

Figure 53:
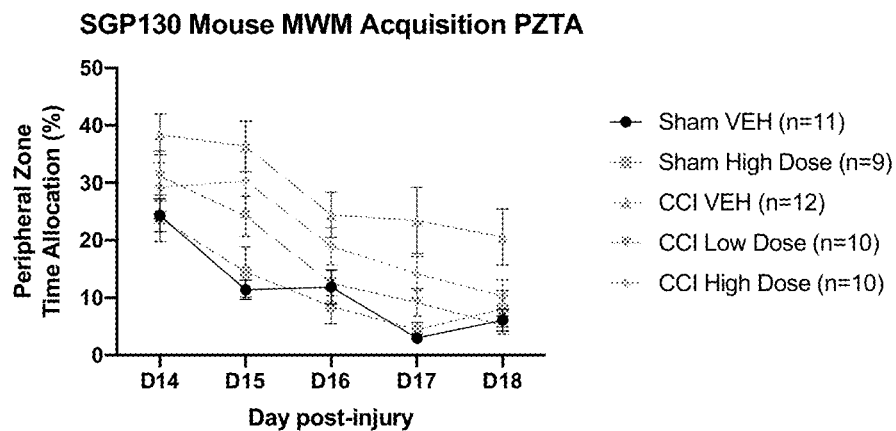

FIG. 53 provides the acquisition PZTA group comparison in CCI mice. Two-Way Repeated Measure ANOVA: Interaction: p=0.4352; Day: p<0.0001; Treatment Group: p<0.0001; Subject: p<0.0001. Post-hoc Tukey's Multiple Comparisons were performed. Decreased PZTA in sgp130 treated mice (CCI Low Dose vs CCI VEH) in connection to lowered anxiety behavior (p=0.0005).

Figure 54:
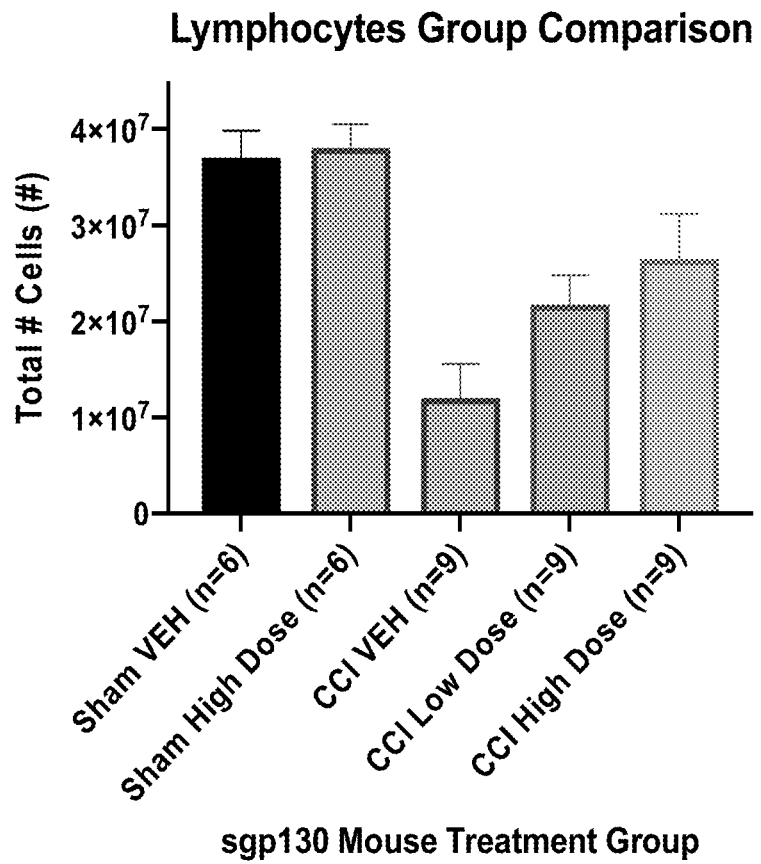

FIG. 54 provides lymphocytes group comparison of mice with different treatments. Tissues were collected at day 21 post-injury. sgp130 was injected at day 1, day 7, day 13 post-injury. High dose of sgp130 referred to 1 ug and low dose of sgp130 referred to 0.25ug. Sgp130 supports proliferation of total lymphocytes in spleen.

Figure 55:
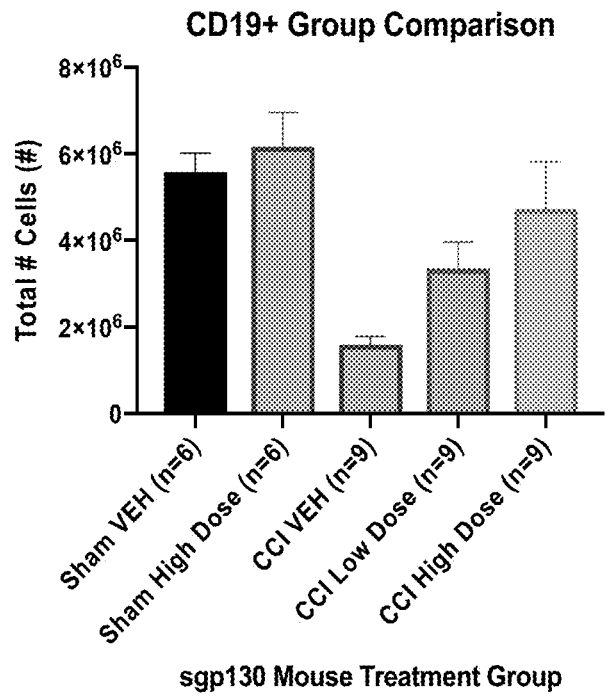

FIG. 55 provides CD19+ group comparison of mice with different treatments. Sgp130 supports proliferation of CD19+ lymphocytes in spleen.

Figure 56:
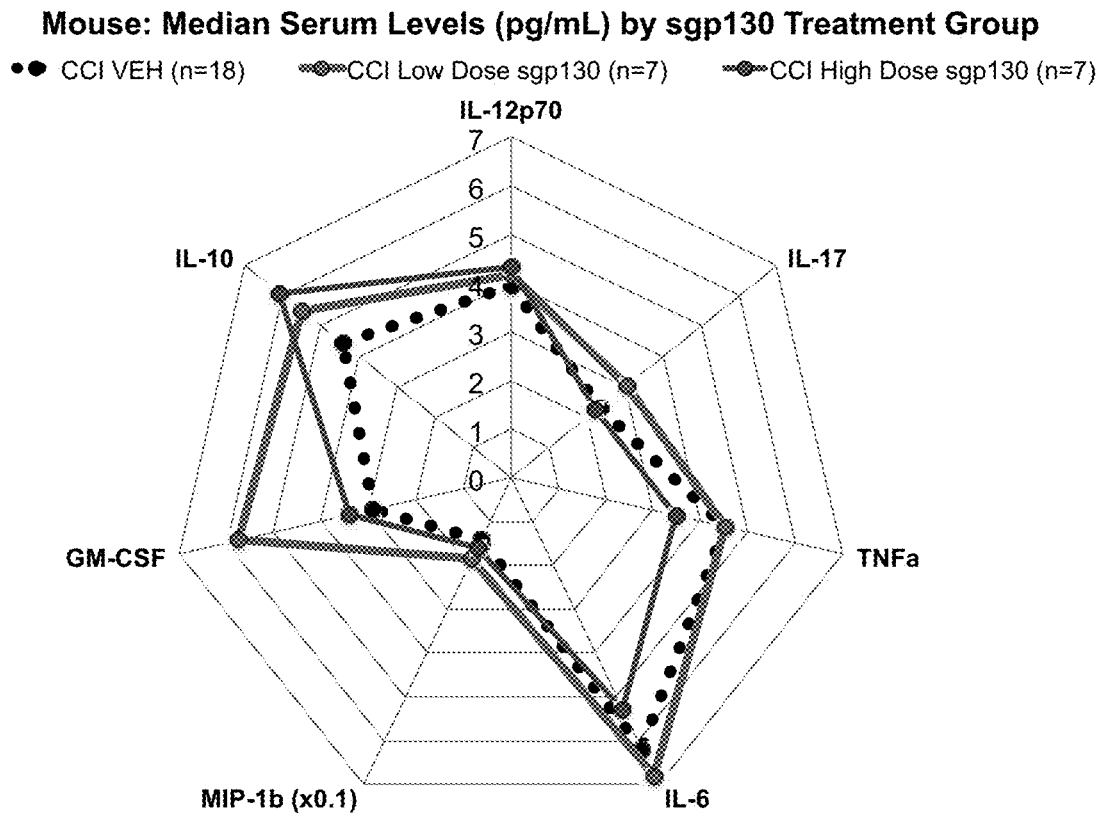

FIG. 56 provides the median serum levels of control group, low dose of sgp130 treated group and high dose of sgp130 treated group.

Figure 57:
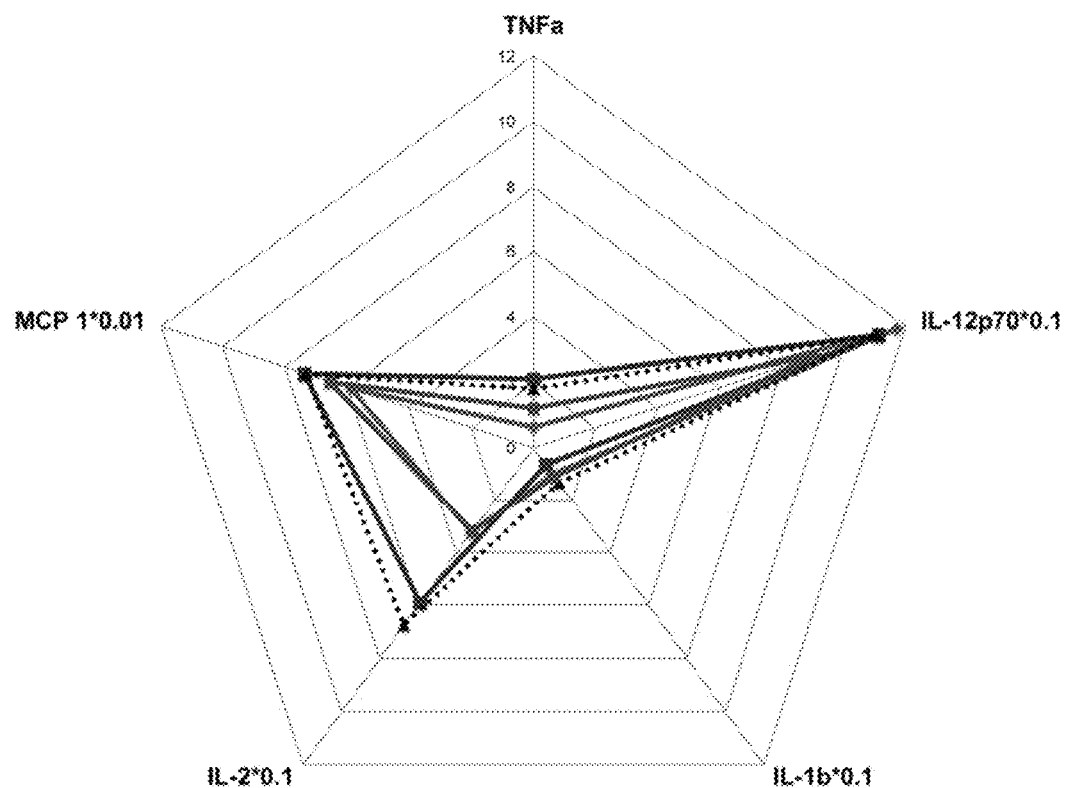

FIG. 57 provides mean serum levels (pg/ml) by sgp130 treatment in rats.

FIG. 58 provides demographic characterization of the cohort and associations of demographic and clinical variables with sgp130:sIL-6R.

Figure 59:
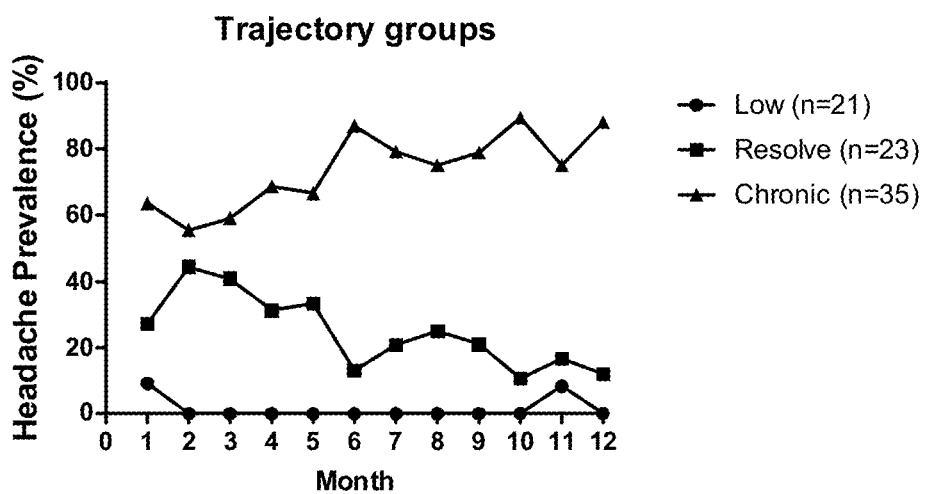

FIG. 59 provides percent of individuals who endorsed headache at a given month by TRAJ group. Individuals must have completed the headache questionnaire to be considered in the denominator.

Figure 60:
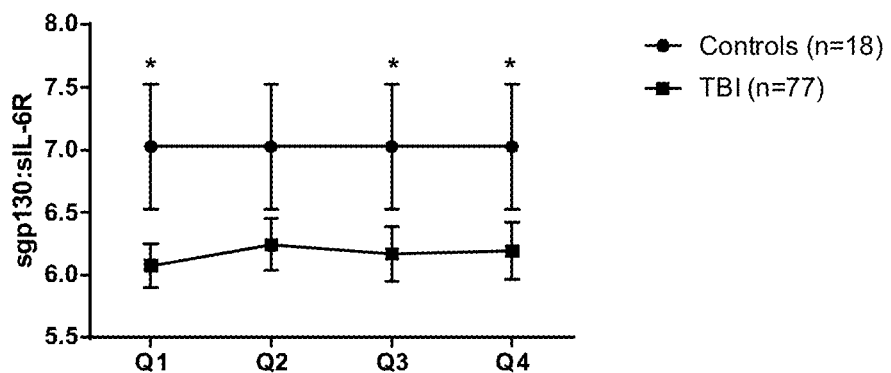

FIG. 60 provides mean quarterly sgp130:sIL6R levels for individuals after a TBI (n=77). Error bars indicate standard error of the mean. Control sgp130:sIL6R values are provided for n=18.

FIG. 61 provides a distribution of sgp130:sIL-6R in the resolve and chronic TRAJ groups. The red line indicates sgp130:sIL-6R=5.9, the determined cut-point.

FIG. 62 provides demographic characterization of the cohort by TRAJ group. Bolded p-values indicate statistically significant differences (p<0.05) between TRAJ groups. BMI: Body Mass Index. GCS: Glasgow Coma Scale.

FIG. 63 provides mean quarterly sgp130:sIL6R levels for the low (n=21), resolve (n=23), and chronic (n=33) headache TRAJ groups. Error bars indicate standard error of the mean. There was a significant difference in ratio levels between TRAJ groups in quarters 1 (p=0.005) and 2 (p=0.013).

FIG. 64 provides mean quarterly sgp130:sIL6R levels for the resolve (n=23) and chronic (n=33) headache TRAJ groups. Error bars indicate standard error of the mean. Control sgp130:sIL6R values are provided for those with no injury (n=18). There was a significant difference in ratio levels between groups in quarters 1 (p=0.001), 2 (p=0.007), and 4 (p=0.020).

FIG. 65 provides univariate and multivariate models for Q1 sgp130:sIL6R. The multivariate model was adjusted for age, sex, GCS, pre-injury history of alcoholism, and pre-injury history of headaches. Bolded p-values indicate statistical significance (p<0.05). GCS: Glasgow Coma Scale.

FIGS. 66A-66B provide headache characteristics for resolve and chronic TRAJ groups. (66A) Quarterly mean number of headache days in a month by resolve (n=23) and chronic (n=35) headache TRAJ groups. Error bars indicate standard error of the mean. The mean number of headache days in the chronic TRAJ group was above 15 in quarters 1, 3, and 4. (66B) Quarterly mean severity of monthly headaches in the resolve (n=23) and chronic (n=35) TRAJ groups. Error bars indicate standard error of the mean. A severity of 1.0 indicates mild severity, 2.0 indicates moderate severity, and 3.0 indicates severe severity.

FIG. 67 provides quality of life by TRAJ group. Quality of Life was measured by self-reported percent back to pre-injury normal functioning and stratified by TRAJ group. Mean (stderr) of total, physical, emotional, and cognitive percentages back to normal were reported at 6 and 12 months. Statistically significant differences between TRAJ groups are indicated by bolded p-values (p<0.05).

Figures 68, 69:
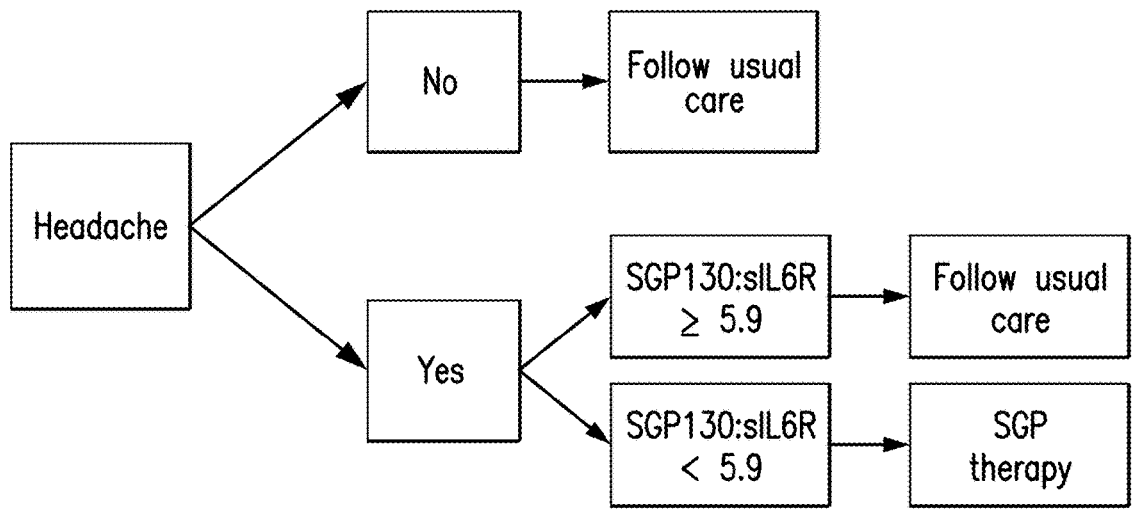

FIG. 68 provides quarterly anxiety, PTD, PROMIS, and FSS by trajectory group. Row a provides quarterly anxiety, measured as mean monthly GAD-7 scores, stratified by TRAJ group. Row b provides quarterly PTD measured via PHQ-9 questionnaires, stratified by TRAJ group. Row c provides quarterly PROMIS questionnaire scores, stratified by TRAJ group. Row d provides quarterly FSS questionnaire scores, stratified by TRAJ group. NOTE: Mean (stderr) reported, unless otherwise specified. Statistically significant differences between TRAJ groups are indicated by bolded p-values (p<0.05).

FIG. 69 provides an example clinical decision tree to model the suggested care and/or treatment for a patient given the sgp130:sIL6R cut point of 5.9.

FIG. 70A provides an interaction graphic showing relationship between mean levels of IL-6 (pg/ml) and sIL-6R (pg/ml) at month 0-3 post-TBI in relationship to neurorecovery measured by GOS scores.

FIG. 70B provides a table showing the variables and their OR and p-values of the GOS neurorecovery regression model.

Figure 71A:
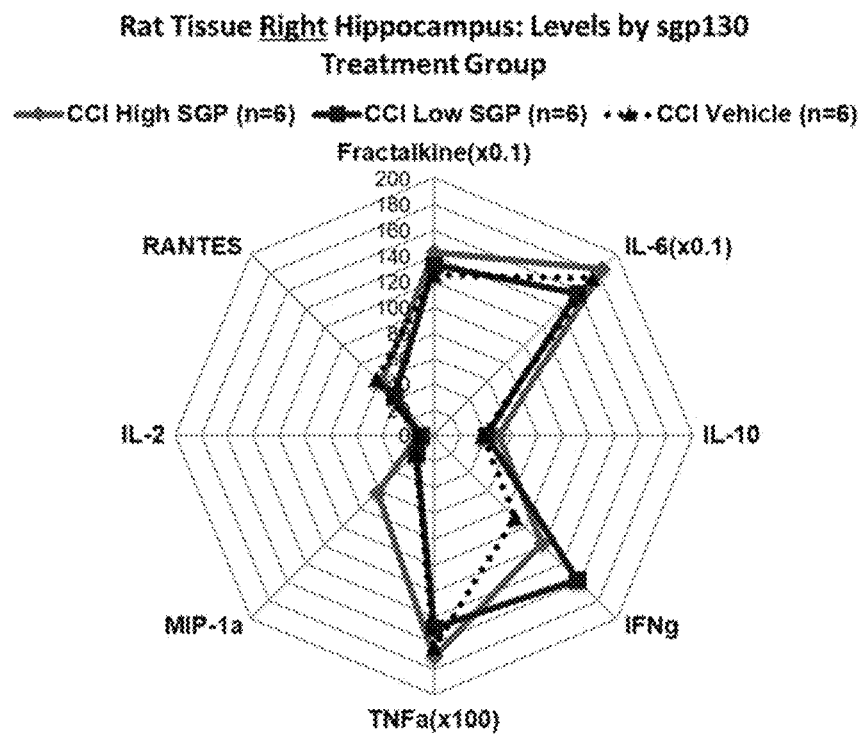

FIG. 71A provides rat right (injury side) hippocampus tissue biomarker levels by sgp130 treatment groups.

Figure 71B:
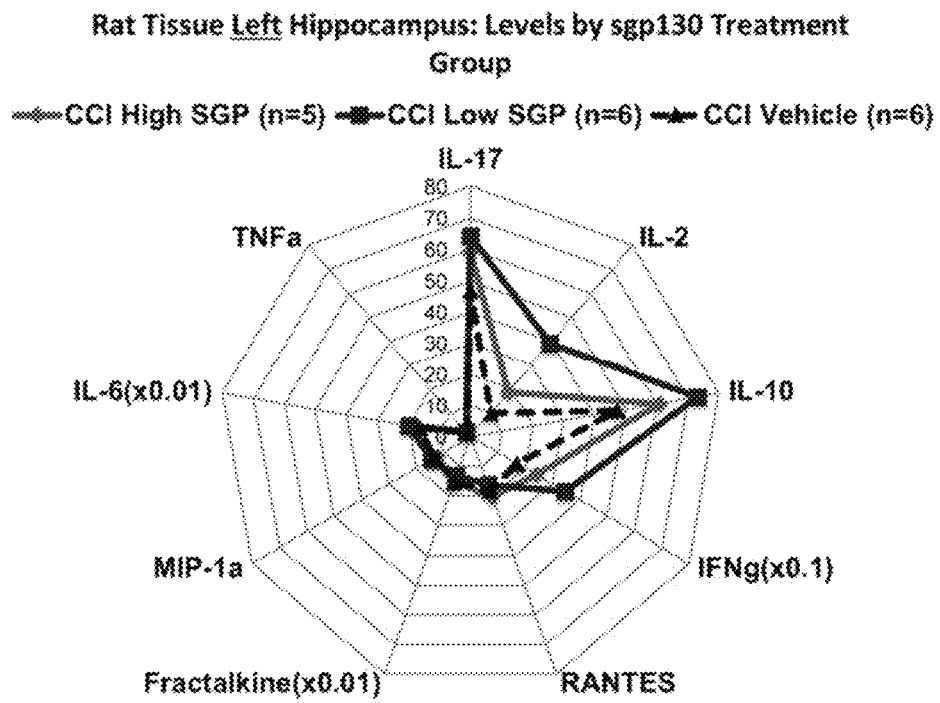

FIG. 71B provides rat left hippocampus tissue biomarker levels by sgp130 treatment groups.

Figure 72A:
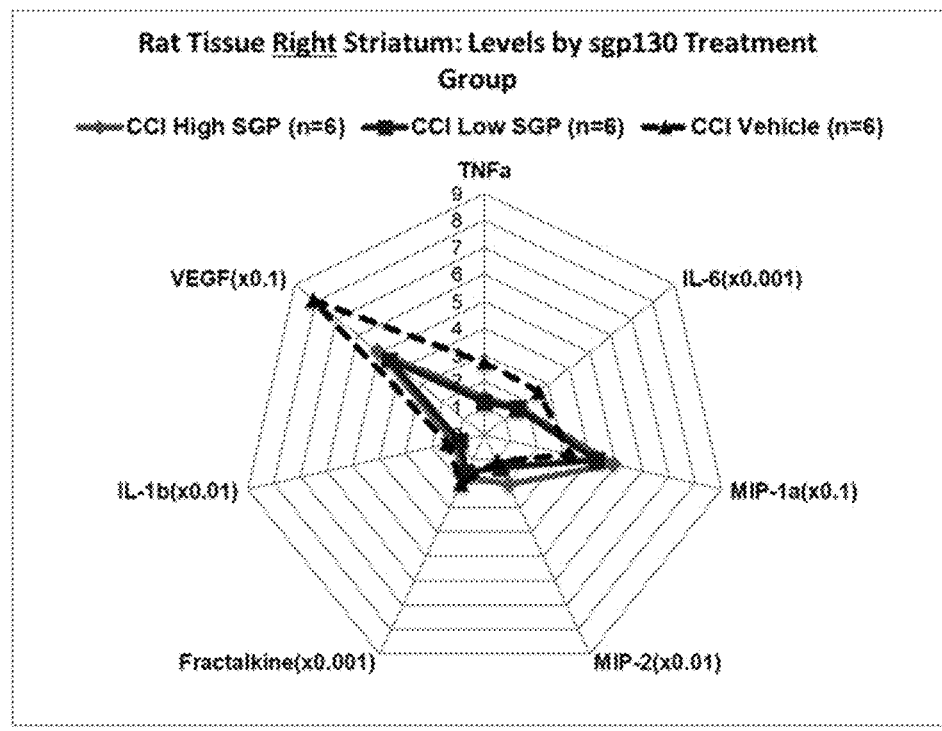

FIG. 72A provides rat right (injury side) striatum tissue biomarker levels by sgp130 treatment groups.

Figure 72B:
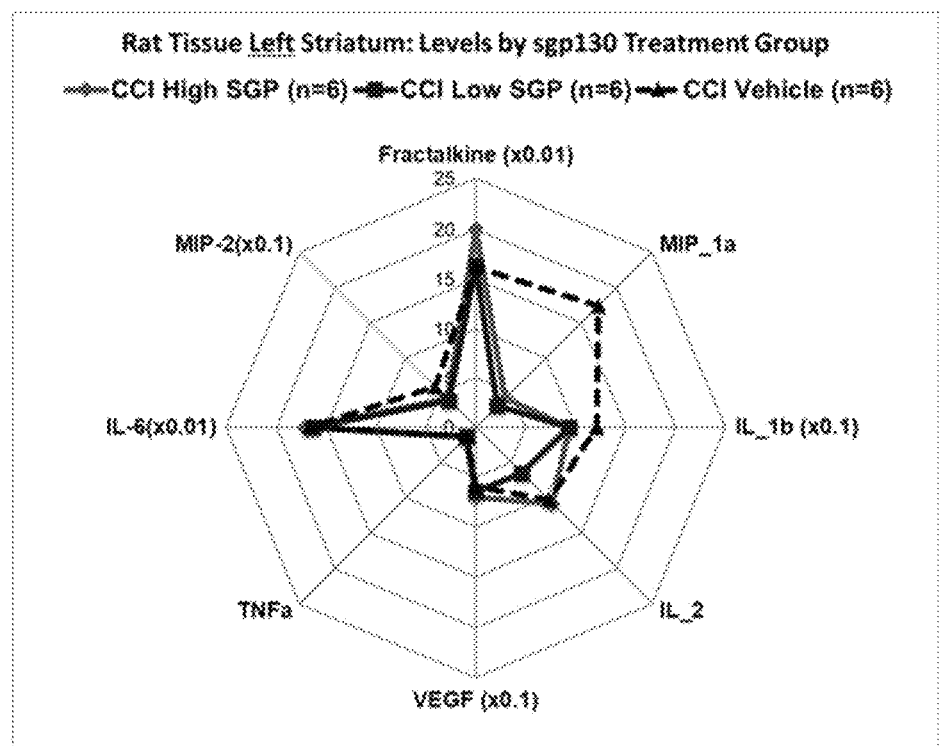

FIG. 72B provides rat left striatum tissue biomarker levels by sgp130 treatment groups.

Figure 73:
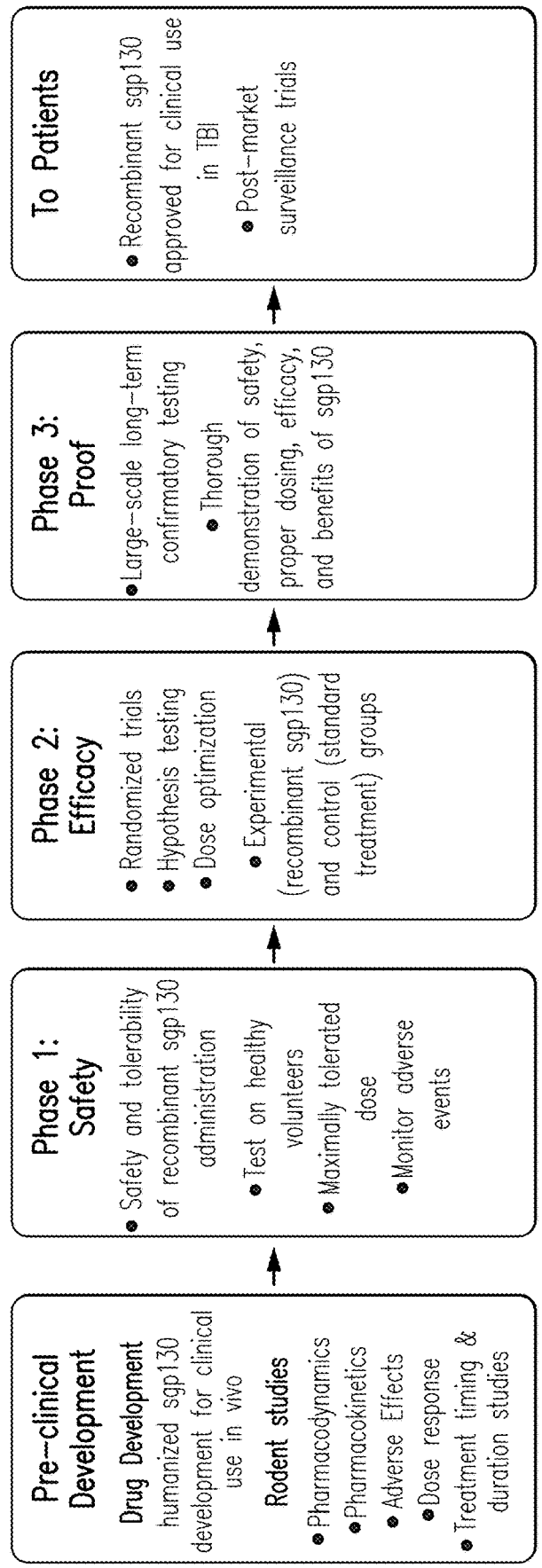

FIG. 73 provides a drug development pipeline schematic for sgp130.

5. DETAILED DESCRIPTION

The present disclosure provides methods, compositions, and kits for treating traumatic brain injury (TBI) and TBI-associated impairments (e.g., posttraumatic headache (PTH), posttraumatic depression (PTD), cognitive deficits, posttraumatic epilepsy (PTE), and seizure) in a subject. It is based, at least in part, on discoveries relating to the roles of IL-6 trans-signaling during recovery from TBI. In certain embodiments, treatment methods disclosed herein include administering to the subject a soluble gp130 (sgp130) or an agent that promotes the binding of sgp130 and sIL-6R and/or reduces sIL-6R mediated trans-signaling.

The present disclosure also provides biomarkers for use in identifying a subject as likely to develop a TBI-associated impairment. The biomarkers disclosed herein can also be used for identifying a subject as likely to respond to a treatment for TBI-associated impairments. The biomarkers disclosed herein include white blood cells indices (e.g., Neutrophil-Lymphocyte Ratio (NLR), absolute lymphocyte counts), sIL-6R, sgp130, IL-6, sgp130:sIL-6R ratio, sIL-2Ra, IL-2, sIL-2Ra:IL-2 ratio, TNFα, TNFRI, and TNFRI:TNFα ratio. Non-limiting embodiments of the present disclosure are described by the present specification and Examples.

For purposes of clarity of disclosure and not by way of limitation, the detailed description is divided into the following subsections:
  5.1 Definitions;
  5.2 Methods of Treatment;
  5.3 Methods of Predicting and Monitoring Responsiveness to a Treatment; and
  5.4 Kits.

5.1 Definitions

The terms used in this specification generally have their ordinary meanings in the art, within the context of the present disclosure and in the specific context where each term is used. Certain terms are discussed below, or elsewhere in the specification, to provide additional guidance to the practitioner in describing the compositions and methods of the present disclosure and how to make and use them.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

An "individual" or "subject" herein is a vertebrate, such as a human or non-human animal, for example, a mammal. Mammals include, but are not limited to, humans, non-human primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

As used herein, the term "disease" refers to any condition or disorder that damages or interferes with the normal function of a cell, tissue, or organ.

An "effective amount" of a substance as that term is used herein is that amount sufficient to effect beneficial or desired results, including clinical results, and, as such, an "effective amount" depends upon the context in which it is being applied. An effective amount can be administered in one or more administrations.

As used herein, and as well-understood in the art, "treatment" is an approach for obtaining beneficial or desired results, including clinical results. For purposes of this subject matter, beneficial or desired clinical results include, but are not limited to, alleviation or amelioration of one or more sign or symptoms, diminishment of extent of disease, stabilized (i.e., not worsening) state of disease, prevention of disease, delay or slowing of disease progression, and/or amelioration or palliation of the disease state. The decrease can be a 10-99% (e.g., 10%, 20%, 30%, 40%, 50%, 60%, 70%, 80%, 90%, 95%, 98% or 99%) decrease in severity of complications, impairments, or symptoms. "Treatment" can also mean prolonging survival as compared to expected survival if not receiving treatment.

As used herein, the term "in vitro" refers to an artificial environment and to processes or reactions that occur within an artificial environment. In vitro environments exemplified, but are not limited to, test tubes and cell cultures.

As used herein, the term "in vivo" refers to the natural environment (e.g., an animal or a cell) and to processes or reactions that occur within a natural environment, such as embryonic development, cell differentiation, neural tube formation, etc.

As used herein, the term "TBI-associated impairment" refers to conditions, symptoms, impairments, or any resulting disabilities that are associated with or caused by traumatic brain injuries, including traumas to the head, such as, for example, traumas caused by accidents and/or sports injuries. In certain embodiments, the TBI-associated impairment is posttraumatic headache (PTH), posttraumatic depression (PTD), cognitive deficits, posttraumatic epilepsy (PTE), or seizure.

As used herein, the term "cognitive impairment" or "cognitive deficit" refers to an acquired deficit in one or more of memory function, problem solving, orientation, attention, visual conceptualization, spatial conceptualization, executive and/or abstraction that impinges on an individual's ability to function independently.

As used herein, the term "biological sample" refers to a sample of biological material obtained from a subject, e.g., a human subject, including a biological fluid, e.g., blood, plasma, serum, urine, sputum, spinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid, bronchoalveolar fluid, biliary fluid and combinations thereof.

As used herein, the term "high dose" of an agent refers to, in an experimental setting, a dose of the agent administered to the subjects that is higher than another dose of the agent administered to the subjects in the same experiment.

As used herein, the term "low dose" of an agent refers to, in an experimental setting, a dose of the agent administered to the subjects that is lower than another dose of the agent administered to the subjects in the same experiment.

As used herein, the term "likely to respond" refers to the probability that a subject will respond favorably to a treatment. The probability can be between about 51% and 100% (e.g., about 51%, about 55%, about 60%, about 70%, about 80%, about 90%, or about 100%).

5.2 Methods of Treatment

The present disclosure provides methods for treating TBI and TBI-associated impairments in a subject. In certain embodiments, the methods disclosed herein include administering to the subject a sgp130 or an agent that promotes the binding of sgp130 and sIL-6R and/or reduces sIL-6R mediated trans-signaling. In certain embodiments, the subject is a human subject. In certain embodiments, the subject is a non-human subject, such as, but not limited to, a dog, a cat, a horse, a rodent, or a non-human primate.

In certain embodiments, the sgp130 or agents that promotes the binding of sgp130 and sIL-6R and/or reduces sIL-6R mediated trans-signaling disclosed herein are administered to the subject in effective amounts that are sufficient to effect beneficial or desired results, including clinical results. In certain embodiments, the effective amounts have the beneficial or desired results of improving outcome (e.g., reducing long-term disability) of TBI, reducing the risk of developing a TBI-associated impairment, alleviating at least one symptom of a TBI-associated impairment, and/or improving at least one clinical results of a TBI-associated impairment.

Effective amounts of sgp130 or agents that promotes the binding of sgp130 and sIL-6R and/or reduces sIL-6R mediated trans-signaling disclosed herein can vary depending upon the characteristics of the subject (e.g., age, sex, race, weight, height, BMI, body fat percentage, and/or medical history), frequency of administration, manner of administration, clearance of sgp130 or agents that promotes the binding of sgp130 and sIL-6R and/or reduces sIL-6R mediated trans-signaling disclosed herein.

In certain embodiments, the methods disclosed herein improve outcome (e.g., reducing long-term disability) of TBI in the subject. In certain embodiments, a good outcome following TBI is associated with one or more of the following: a Glasgow Outcome Scale score of greater than or equal to 4; a Disability Rating Scale (DRS) score of less than 7, or less than 6, or less than 5, or less than 4, or less than or equal to 3; mild or moderate or essentially no post-traumatic epilepsy; mild or moderate or no hypogonadotropic hypogonadism; a Ranchos Los Amigos Scale score of Level VI, Level VII or Level VIII; or mild or moderate presence of one or more of fatigue, headaches, visual disturbances, memory loss, poor attention/concentration, sleep disturbances, dizziness/loss of balance, irritability-emotional disturbances, and/or feelings of depression. A good outcome may be measured at least 2 months, at least 4 months, at least 6 months, at least 8 months, or at least 12 months following TBI. In certain embodiments, the methods disclosed herein reduce the extent of disability following TBI. In certain embodiments, the methods disclosed herein increase the likelihood of a good outcome following TBI.

The present disclosure further provides methods for treating or reducing the risk of developing a TBI-associated impairment (e.g., conditions, symptoms, impairments, and resulting disabilities) in a subject, including administering to the subject a sgp130 or an agent that promotes the binding of sgp130 and sIL-6R and/or reduces sIL-6R mediated trans-signaling.

In certain embodiments, methods disclosed herein treat or reduce the risk of developing a TBI-associated impairment selected from the group consisting of cognitive deficits (e.g., attention deficit, memory deficit, and impaired visual or spatial conceptualization), psychological deficits (e.g. personality changes, mood disturbance, substance abuse), somatic symptoms (e.g., headaches, visual disturbances), emotional symptoms (e.g., irritability), behavioral dysfunctions (e.g., aggression, impulsivity), physical dysfunctions (e.g., cranial or peripheral nerve damage, impairment in motor functioning, strength and coordination, or impairment in sensation). In certain embodiments, the TBI-associated impairment is selected from the group consisting of post-traumatic headache (PTH), posttraumatic depression (PTD), cognitive deficits, posttraumatic epilepsy (PTE), seizure, and combinations thereof.

In certain embodiments, the TBI-associated impairment is a TBI-associated cognitive deficit. In certain embodiments, the cognitive deficit is selected from the group consisting of memory deficit, attention deficit, impaired visual conceptualization, and impaired spatial conceptualization. In certain embodiments, the methods disclosed herein improve cognitive deficits as measured by a cognitive assessment tool. Any cognitive assessment tool known in the art can be used with the subject matter disclosed herein. Non-limiting examples of cognitive assessment tools include Controlled Oral Word Association Test, the Trail Making Test, the Stroop Color-Word Matching Test, the California Verbal Learning Test, the Digit Span Test (from the Wechsler Adult Intelligence Scale-III), the Processing Speed Index.

In certain embodiments, the methods disclosed herein include administering the sgp130 or the agent that promotes the binding of sgp130 and sIL-6R and/or reduces sIL-6R mediated trans-signaling to the subject at acute, post-acute, and/or chronic stage of the TBI. In certain embodiments, acute stage of TBI refers to the period within about 24 hours or about one week after occurrence of TBI. In certain embodiments, post-acute stage of TBI refers to the period from about 1 week to up to about 4 weeks after occurrence of TBI. In certain embodiments, early chronic stage of TBI refers to the period from about 4 weeks to about 6 months after occurrence of TBI. In certain embodiments, chronic stage of TBI refers to the period at least about 4 weeks, at least about 6 months, or at least 12 months after occurrence of TBI.

In certain embodiments, the sgp130 or the agent that promotes the binding of sgp130 and sIL-6R and/or reduces sIL-6R mediated trans-signaling is administered to the subject within about 24 hours, within about 3 days, within about one week, within about 2 weeks, within about 3 weeks, within about one month, or within about 3 months, within about 4 months, within about 5 months, within about 6 months, within about 7 months, within about 8 months, within about 9 months, within about 10 months, within about 11 months, within one year, within about 1.5 year, or within about 2 years of TBI from the occurrence of TBI. In certain embodiments, the sgp130 or the agent that promotes the binding of sgp130 and sIL-6R and/or reduces sIL-6R mediated trans-signaling is administered to the subject between about one month and about six months after the occurrence of TBI.

Signal transduction in response to interleukin-6 (IL-6) requires binding of the cytokine to its receptor (IL-6R) and subsequent homodimerization of the signal transducer gp130. The complex of IL-6 and soluble IL-6R (sIL-6R) triggers dimerization of gp130 and induces responses on cells that do not express membrane bound IL-6R. Soluble gp130 (sgp130) is a potent IL-6 inhibitory protein, and high level of sgp130 inhibits formation of the IL-6/sIL-6R complex (Jostock et al., 2001, Eur J Biochem. January; 268(1): 160-7).

In certain embodiments, the sgp130 to be used with the presently disclosed methods is of the same species or a different species from the subject to be treated. In certain embodiments, the sgp130 is a human sgp130 or a recombinant human sgp130. In certain embodiments, the human sgp130 or the recombinant human sgp130 is used for treating a human subject. In certain embodiments, the spg130 is a sgp130/Fc dimer as disclosed in, for example, U.S. Pat. No. 9,034,817, the content of which is incorporated by reference herein in its entirety. In certain embodiments, the sgp130/Fc dimer includes two soluble gp130 molecules wherein each of said molecules is fused to an Fc domain of an IgG1 protein. In certain embodiments, the hinge region of the Fc domain is modified resulting in advantageous properties of the dimer.

In certain embodiments, the agent that promotes the binding of sgp130 and sIL-6R and/or reduces sIL-6R mediated trans-signaling is a monoclonal antibody. In certain embodiments, the monoclonal antibody is siltuximab. Siltuximab (trade name Sylvant; also known as CNTO 328, anti-IL-6 chimeric monoclonal antibody or cCLB8) can prevent IL-6 from binding to membrane-bound and soluble IL-6R.

In certain embodiments, the monoclonal antibody is an anti-IL-6 trans-signaling antibody. An non-limiting exemplary anti-IL-6 trans-signaling antibody, 25F10, is disclosed in Garbers et al., J Biol Chem. 2011, 286(50): 42959-42970, the contents of which are incorporated by reference herein in its entirety.

In certain embodiments, the sgp130 is administered to the subject in an amount of between about 3 µg and about 100 µg. In certain embodiments, the sgp130 is administered to the subject in an amount of about 3 µg, about 6 µg, about 10 µg, about 12 µg, about 20 µg, about 25 µg, about 30 µg, about 35 µg, about 40 µg, about 50 µg, about 60 µg, about 70 µg, about 80 µg, about 90 µg, or about 100 µg. In certain embodiments, the sgp130 is administered to the subject in an amount of about 3 µg, about 6 µg, about 12 µg, or about 36 µg.

In certain embodiments, the sgp130 is administered to the subject in an amount of between about 0.5 µg/kg and about 50 µg/kg. In certain embodiments, the sgp130 is administered to the subject in an amount of about 0.5 µg/kg, about 1 µg/kg, about 5 µg/kg, about 10 µg/kg, about 15 µg/kg, about 20 µg/kg, about 25 µg/kg, about 30 µg/kg, about 35 µg/kg, about 40 µg/kg, about 45 µg/kg, or about 50 µg/kg. In certain embodiments, the sgp130 is administered to the subject in an amount of about 0.25 µg/kg, about 0.5 µg/kg, about 1 µg/kg, about 2 µg/kg, or about 3 µg/kg.

In certain embodiments, a sgp130 or an agent that promotes the binding of sgp130 and sIL-6R and/or reduces sIL-6R mediated trans-signaling is administered to the subject daily. In certain embodiments, a sgp130 or an agent that promotes the binding of sgp130 and sIL-6R and/or reduces sIL-6R mediated trans-signaling is administered to the subject once per day, twice per day, or three times per day. In certain embodiments, a sgp130 or an agent that promotes the binding of sgp130 and sIL-6R and/or reduces sIL-6R mediated trans-signaling is administered to the subject once per week, every two weeks, every three week, every four weeks, every five weeks, every six weeks, every seven weeks, or every eight weeks. In certain embodiments, a sgp130 or an agent that promotes the binding of sgp130 and sIL-6R and/or reduces sIL-6R mediated trans-signaling is administered one, two, three, four, five, or six days per week.

The amount of the sgp130 or the agent that promotes the binding of sgp130 and sIL-6R and/or reduces sIL-6R mediated trans-signaling administered to the subject disclosed herein can vary depending upon the characteristics of the subject (e.g., age, sex, race, weight, height, BMI, body fat percentage, and/or medical history), frequency of administration, manner of administration, clearance of the sgp130 or an agent that promotes the binding of sgp130 and sIL-6R and/or reduces sIL-6R mediated trans-signaling.

Sgp130, or agents that promotes binding between sgp130 and sIL-6R, may be administered by any suitable route known in the art, including, but not limited to, parenteral, topical, intravenous, subcutaneous, intraperitoneal, intrapulmonary, intranasal, and/or intralesional, intra-arterial, intrathecal, or by local instillation into the central nervous system. Parenteral infusions include intramuscular, intravenous, intraarterial, intraperitoneal, or subcutaneous administration. Intrathecal administration is also contemplated (see, e.g., U.S. Patent Publication No. 2002/0009444 by Grillo-Lopez, which is incorporated herein by reference in its entirety).

5.3 Methods of Predicting and Monitoring Responsiveness to a Treatment

The present disclosure provides methods for predicting a subject who has sustained TBI as likely to develop a TBI-associated impairment, the methods including: determining the level of a biomarker in a sample obtained from the subject, comparing the level of the biomarker to a reference level, identifying the subject as likely to develop the TBI-associated impairment.

The present disclosure also provides methods for identifying a subject who has sustained TBI as likely to respond to a treatment for a TBI-associated impairment, the methods including determining the level of a biomarker in a sample obtained from the subject, comparing the level of the biomarker to a reference level, identifying the subject as likely to respond to the treatment based on the comparison. In certain embodiments, the methods further include treating the subject that is identified as likely to respond to the treatment.

In certain embodiments, the reference level is a predetermined level of a biomarker that a level higher than the reference level indicates that the subject is likely to be responsive to a treatment of a TBI-associated impairments. In certain embodiments, the reference level is a predetermined level of a biomarker that a level lower than the reference level indicates the subject that is likely to be responsive to a treatment of a TBI-associated impairments. In certain embodiments, the reference level is the level of a biomarker from a healthy individual or a population of healthy individuals free of the TBI-associated impairment. In certain embodiments, the reference level is the level of a biomarker from the same subject collected at an earlier time point.

The present disclosure also provides methods for monitoring a subject's responsiveness to a treatment for a TBI-associated impairment, including determining the level of a biomarker in a sample obtained from the subject before receiving the treatment, determining the level of the biomarker in a sample obtained from the subject at during or after receiving the treatment, comparing the levels of the biomarker in the samples, where a change of the level of the biomarker during or after the treatment indicates the responsiveness of the subject to the treatment. In certain embodiments, the methods further include continuing the treatment if the subject is responsive to the treatment, and treating the subject with a different treatment or a different dosing regimen for the TBI-associated impairment if the subject is not responsive to the treatment.

In certain embodiments, the level of the biomarker is determined in a blood sample obtained from a subject. In certain embodiments, the blood sample is a plasma sample, a serum sample, or a central nervous system (CNS)-derived exosomal fraction of the blood sample.

In certain embodiments, the sample is obtained from the subject at the post-acute and/or chronic stage of the TBI. In certain embodiments, the sample is obtained from the subject from about 1 week to about 4 weeks after the occurrence of the TBI. In certain embodiments, the sample is obtained from the subject at least about 4 weeks, at least about 6 months, or at least 12 months after occurrence of TBI.

In certain embodiments, the biomarker is sgp130, sIL-6R, IL-6, sgp130:sIL-6R ratio, Neutrophil-Lymphocyte Ratio (NLR), or combinations thereof. In certain embodiments, the biomarker is a combination of sgp130:sIL-6R ratio and sIL-6R.

Any agents or treatments known in the art for treating TBI-associated impairments, can be used with the methods disclosed herein. In certain embodiments, the treatment for the TBI-associated impairment includes citicoline, a neurostimulator, dopamine agonists, and/or anticonvulsants. In certain embodiments, the treatment for the TBI-associated impairment includes a sgp130 or an agent that promotes the binding of sgp130 and sIL-6R and/or reduces sIL-6R mediated trans-signaling as disclosed herein.

In certain embodiments, the methods further include identifying the subject as likely to respond to a treatment of a TBI-associated impairment or as likely to develop a TBI-associated impairment, if the level of the biomarker is higher than the reference level. In certain embodiments, the biomarker is selected from white blood cells indices (e.g., Neutrophil-Lymphocyte Ratio (NLR), absolute lymphocyte counts), sIL-6R, sgp130, IL-6, sgp130:sIL-6R ratio, sIL-2Ra, IL-2, sIL-2Ra:IL-2 ratio, TNFα, TNFRI, and TNFRI:TNFα ratio, and combinations thereof. In certain embodiments, the treatment includes administering a sgp130 or an agent that promotes the binding of sgp130 and sIL-6R and/or reduces sIL-6R mediated trans-signaling. In certain embodiments, the treatment is administered at the post-acute and/or chronic stage of the TBI.

In certain embodiments, the biomarker is NLR. In certain embodiments, the reference level of NLR is a predetermined level of NLR. In certain embodiments, the predetermined level of NLR is between about 5 and about 50. In certain embodiments, the predetermined level of NLR is about 5, about 10, about 15, about 20, about 30, about 40, or about 50. In certain embodiments, the predetermined level of NLR is about 10. In certain embodiments, the level of NLR is determined in a blood sample obtained from the subject. In certain embodiments, the methods disclosed herein include identifying the subject as likely to respond to a treatment of a TBI-associated impairment or as likely to develop a TBI-associated impairment, if the level of NLR is higher than about 10. In certain embodiments, the NLR is measured at the acute and/or post-acute stage of the TBI. In certain embodiments, the NLR is measured within about 3 weeks after the occurrence of the TBI.

In certain embodiments, the biomarker is sIL-6R. In certain embodiments, the reference level of sIL-6R is a predetermined level of sIL-6R. In certain embodiments, the predetermined level of sIL-6R is between about 15,000 pg/ml and about 35,000 pg/ml. In certain embodiments, the predetermined level of sIL-6R is about 15,000 pg/ml, about 16,000 pg/ml, about 18,000 pg/ml, about 20,000 pg/ml, about 21,000 pg/ml, about 22,000 pg/ml, about 23,000 pg/ml, about 24,000 pg/ml, about 26,000 pg/ml, about 28,000 pg/ml, about 30,000 pg/ml, about 31,000 pg/ml, about 32,000 pg/ml, about 33,000 pg/ml, about 34,000 pg/ml, or about 35,000 pg/ml. In certain embodiments, the predetermined level of sIL-6R is about 22,000 pg/ml. In certain embodiments, the predetermined level of sIL-6R is about 20,000 pg/ml. In certain embodiments, the level of sIL-6R is determined in a blood sample obtained from the subject. In certain embodiments, the methods disclosed herein include identifying the subject as likely to respond to a treatment of a TBI-associated impairment or as likely to develop a TBI-associated impairment, if the level of sIL-6R is higher than about 22,000 pg/ml, or about 20,000 pg/ml.

In certain embodiments, the methods disclosed herein further include identifying the subject as likely to respond to a treatment of a TBI-associated impairment or as likely to develop a TBI-associated impairment, if the level of the biomarker is lower than the reference level. In certain embodiments, the biomarker is selected from the group consisting of sgp130:sIL-6R ratio, sgp130, or a combination thereof. In certain embodiments, the treatment includes administering a sgp130 or an agent that promotes the binding of sgp130 and sIL-6R and/or reduces sIL-6R mediated trans-signaling. In certain embodiments, the treatment is administered at the post-acute and/or chronic stage of the TBI.

In certain embodiments, the biomarker is sgp130:sIL-6R ratio. In certain embodiments, the reference level of sgp130:sIL-6R ratio is a predetermined level of sgp130:sIL-6R ratio. In certain embodiments, the predetermined level of sgp130:sIL-6R ratio is between about 2 and about 15. In certain embodiments, the predetermined level of sgp130:sIL-6R ratio is about 2, about 3, about 4, about 4.5, about 5, about 5.5, about 6, about 6.5, about 7, about 8, about 9, about 10, about 11, about 12, about 13, about 14, or about 15. In certain embodiments, the predetermined level of sgp130:sIL-6R ratio is about 6.5. In certain embodiments, the level of sgp130:sIL-6R ratio is determined in a blood sample obtained from the subject. In certain embodiments, the methods disclosed herein include identifying the subject as likely to respond to a treatment of a TBI-associated impairment or as likely to develop a TBI-associated impairment, if the level of sgp130:sIL-6R ratio is lower than about 6.5.

In certain embodiments, the biomarker is sgp130. In certain embodiments, the reference level of sgp130 is a predetermined level of sgp130. In certain embodiments, the predetermined level of sgp130 is between about 80,000 pg/ml and about 200,000 pg/ml. In certain embodiments, the predetermined level of sgp130 is about 80,000 pg/ml, about 100,000 pg/ml, about 110,000 pg/ml, about 120,000 pg/ml, about 130,000 pg/ml, about 140,000 pg/ml, about 150,000 pg/ml, about 160,000 pg/ml, about 170,000 pg/ml, about 180,000 pg/ml, about 190,000 pg/ml, or about 30,000 pg/ml. In certain embodiments, the predetermined level of sgp130 is about 130,000 pg/ml. In certain embodiments, the level of sgp130 is determined in a blood sample obtained from the subject. In certain embodiments, the methods disclosed herein include identifying the subject as likely to respond to a treatment of a TBI-associated impairment or as likely to develop a TBI-associated impairment, if the level of sgp130 is lower than about 130,000 pg/ml. In certain embodiments, the TBI-associated impairment is PTD.

In certain embodiments, the TBI-associated impairment is PTE, and if the level of sgp130 is higher than the reference level of sgp130, the subject is likely to develop PTE or is likely to response to a treatment of PTE. In certain embodiments, the reference level of sgp130 is between about 140,000 pg/ml and about 200,000 pg/ml, or between about 160,000 pg/ml and about 180,000 pg/ml. In certain embodiments, the reference level of sgp130 is about 160,000 pg/ml, or about 180,000 pg/ml. In certain embodiments, the biomarker is a combination of sIL-6R and sgp130:sIL-6R ratio. In certain embodiments, the reference levels of sIL-6R and sgp130:sIL-6R ratio are predetermined levels. In certain embodiments, the methods disclosed herein include identifying the subject as likely to respond to a treatment of a TBI-associated impairment or as likely to develop a TBI-associated impairment, if the level of sIL-6R is higher than about 22,000 pg/ml and the level of sgp130:sIL-6R ratio is lower than about 6.5.

In certain embodiments, the TBI-associated impairment is selected from the group consisting of posttraumatic headache (PTH), posttraumatic depression (PTD), cognitive deficits, posttraumatic epilepsy (PTE), seizure, and combinations thereof.

5.4 Kits

The present disclosure further provides a kit for identifying a subject who has sustained TBI as likely to respond to a treatment for a TBI-associated impairment. The present disclosure further provides a kit for identifying a subject who has sustained TBI as likely to develop a TBI-associated impairment. The present disclosure further provides a kit for monitoring a subject's responsiveness to a treatment for a TBI-associated impairment.

In certain embodiments, the kit is configured for detecting a biomarker, e.g., using a detector. In certain embodiments, the biomarker is sgp130:sIL-6R ratio, sgp130, sIL-6R, IL-6, Neutrophil-Lymphocyte Ratio (NLR), or any combinations thereof.

Types of kits include, but are not limited to, packaged biomarker-specific probe and primer sets (e.g., TaqMan probe/primer sets), arrays/microarrays, biomarker-specific antibodies, biomarker-specific beads, which further contain one or more probes, primers, or other reagents for detecting one or more biomarkers of the present disclosure.

Non-limiting example of detectors that can be used with the presently disclosed kits include antibodies for immunodetection of the biomarker(s) to be identified, oligonucleotide primers suitable for polymerase chain reaction (PCR) or nucleic acid sequencing; nucleic acid probes suitable for in situ hybridization or fluorescent in situ hybridization.

In certain non-limiting embodiments, the detector includes at least one antibody for immunodetection of the biomarker(s) to be identified. Antibodies, both polyclonal and monoclonal, specific for a biomarker, can be prepared using conventional immunization techniques, as will be generally known to those of skill in the art. The immunodetection reagents of the kit can include detectable labels that are associated with, or linked to, the given antibody or antigen itself. Such detectable labels include, for example, chemiluminescent or fluorescent molecules (rhodamine, fluorescein, green fluorescent protein, luciferase, Cy3, Cy5, or ROX), radiolabels ($^3H$, $^{35}S$, $^{32}P$, $^{14}C$, $^{131}I$) or enzymes (alkaline phosphatase, horseradish peroxidase).

In certain non-limiting embodiments, the biomarker-specific antibody can be provided bound to a solid support, such as a column matrix, an array, or well of a microtiter plate. Alternatively, the support can be provided as a separate element of the kit.

In certain non-limiting embodiments, the detector includes a pair of oligonucleotide primers suitable for polymerase chain reaction (PCR) or nucleic acid sequencing, for detecting one or more biomarker(s) to be identified. A pair of primers can include nucleotide sequences complementary to a biomarker and be of sufficient length to selectively hybridize with said biomarker. Alternatively, the complementary nucleotides can selectively hybridize to a specific region in close enough proximity 5' and/or 3' to the biomarker position to perform PCR and/or sequencing. Multiple biomarker-specific primers can be included in the kit to simultaneously assay large number of biomarkers. The kit can also include one or more polymerases, reverse transcriptase and nucleotide bases, wherein the nucleotide bases can be further detectably labeled.

In certain non-limiting embodiments, a primer can be at least about 10 nucleotides or at least about 15 nucleotides or at least about 20 nucleotides in length and/or up to about 200 nucleotides or up to about 150 nucleotides or up to about 100 nucleotides or up to about 75 nucleotides or up to about 50 nucleotides in length.

In certain non-limiting embodiments, the oligonucleotide primers can be immobilized on a solid surface or support, for example, on a nucleic acid microarray, wherein the position of each oligonucleotide primer bound to the solid surface or support is known and identifiable.

In certain non-limiting embodiments, the detector includes at least one nucleic acid probe, suitable for in situ hybridization or fluorescent in situ hybridization, for detecting the biomarker(s) to be identified. Such kits will generally include one or more oligonucleotide probes that have specificity for various biomarkers.

In certain non-limiting embodiments, a kit can include one or more primers, probes, microarrays, or antibodies suitable for detecting one or more biomarkers.

In certain non-limiting embodiments, where the measurement techniques in the kit employs an array, the set of biomarkers set forth above can constitute at least 10 percent or at least 20 percent or at least 30 percent or at least 40 percent or at least 50 percent or at least 60 percent or at least 70 percent or at least 80 percent of the species of markers represented on the microarray. In certain non-limiting embodiments, a biomarker detection kit can include one or more detection reagents and other components (e.g., a buffer, enzymes such as DNA polymerases or ligases, chain extension nucleotides such as deoxynucleotide triphosphates, and in the case of Sanger-type DNA sequencing reactions, chain terminating nucleotides, positive control sequences, negative control sequences, and the like) necessary to carry out an assay or reaction to detect a biomarker. A kit can also include additional components or reagents necessary for the detection of a biomarker, such as secondary antibodies for use in immunohistochemistry.

In certain embodiments, the kit further includes instructions or supporting material that describe the use of the kit to identify a subject as likely to respond to a treatment for a TBI-associated impairment and/or reference to a website or publication describing same. In certain embodiments, the kit further includes instructions or supporting material that describe the use of the kit to identify a subject that is as likely to develop a TBI-associated impairment and/or reference to a website or publication describing same. In certain embodiments, the kit further includes instructions or supporting material that describe the use of the kit to monitor the responsiveness of a subject to a treatment for a TBI-associated impairment and/or reference to a website or publication describing same.

In certain embodiments, the treatment includes a sgp130 or an agent that promotes the binding of sgp130 and sIL-6R and/or reduces sIL-6R mediated trans-signaling as disclosed in Section 5.2.

6. EXAMPLE

The presently disclosed subject matter will be better understood by reference to the following Example, which is provided as exemplary of the presently disclosed subject matter, and not by way of limitation.

Example 1: IL-6 Soluble Receptor Signaling and TBI Recovery

The present study was performed to identify at risk individuals for complication post-TBI; to generate actionable information that can influence clinical decision making; to generate clinical data that helps guide pre-clinical studies in post-acute TBI treatment; to generate clinical assessments that aid in early risk stratification and prevention based treatments; to facilitate neuro-repair in the post-acute phase of TBI recovery; to identify improved or optimal treatment doses and effects among a varied population with TBI.

Figure 1:
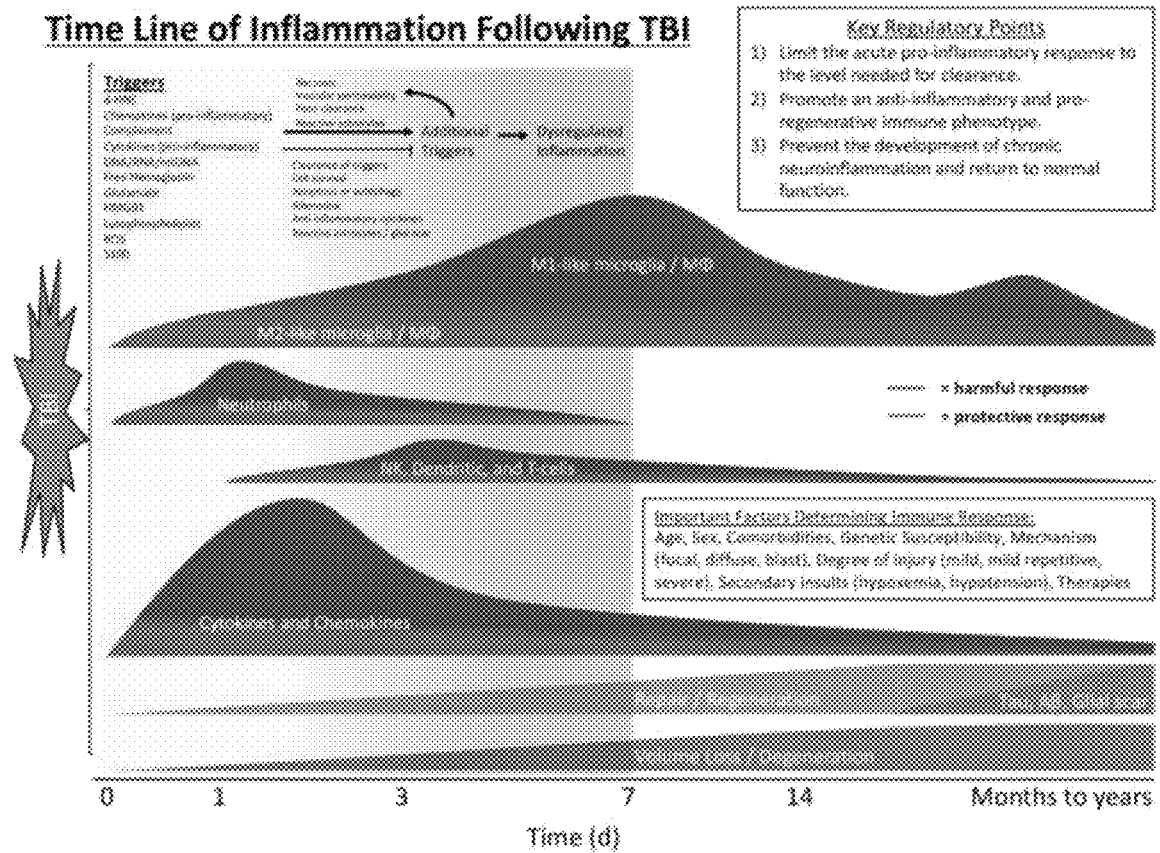
FIG. 1 depicts a scheme of the microglial (MG) activation timeline after CNS injury, including inflammatory events and neurotoxic profiles in the acute and chronic phases. Also indicated are the proposed W and M2 microglial ratios over time.

TBI pathophysiology involves inflammation, which is produced in conjunction with extravasation of blood components through a compromised blood brain barrier (FIG. 1). Cytokines play a major role in the inflammatory cascade after TBI by initiating the molecular events required for immune-activation of multiple brain cell types-microglia and astrocytes, and multiple peripheral cell types-neutrophils, macrophages, lymphocytes. Cytokines can promote neurotoxicity by facilitating excitotoxicity & oxidative stress and propagating the immune response. Cytokines can attenuate CNS damage by promoting potentially neuro-reparative effects through angiogenesis and neurotrophic mechanisms.

The secondary injury response after severe TBI is characterized by an acute innate immune response. Certain research has focused on acute neuroinflammatory markers. IL-6 release is a central part of the acute inflammatory response and a leading indicator of neuroinflammation (Kumar et al., Brain Behav Immun. 2016 March; 53:183-193). However, chronic inflammation after TBI is poorly understood. It was hypothesized that prolonged inflammation in the first few months after TBI is a large contributor to the persistent complications that occur post-injury. There are numerous considerations for clinicians prescribing anti-inflammatory therapies using a precision therapy approach. For instance, the ideal target for therapeutic inflammatory intervention may be the transition from acute chronic inflammation (Lucas et al, Br J Pharmacol. 2006 January; 147(Suppl 1): S232-S240). Certain work suggests sub-acute and chronic peripheral inflammatory markers influence long-term outcome. Pro-inflammatory mediators, such as IL-6, in the sub-acute phase were associated with worse global outcomes at 6 and 12 months after injury (Kumar et al., Brain Behav Immun. 2016 March; 53:183-193).

Cytokine sources in the brain are hypothesized to be derived from neurons, microglia, and astrocytes. Following secondary injury, centrally derived cytokines, including IL10, IL-6 and TNFα can contribute to increased blood-brain barrier (BBB) permeability. Post-TBI, in the context of sustained acute neuroinflammation, higher CSF IL-6 levels are associated with worse global outcomes at 6 months.

IL-6 receptor signaling may be a therapeutic target. IL-6 signaling has pleiotropic inflammatory functions. Classical IL-6 protects against septic shock and directs resolution of acute inflammation. However, IL-6 family cytokines elicit a detrimental response in the context of trans-signaling and chronic inflammation. Additionally, pathogenic IL-6 signaling in the CNS is done almost exclusively via trans-signaling. As such, chronic serum IL-6 trans-signaling may be a dominant mechanism for pathogenic roles on BBB disruption after injury and can be an indicator of brain trans-signaling.

Figure 2:
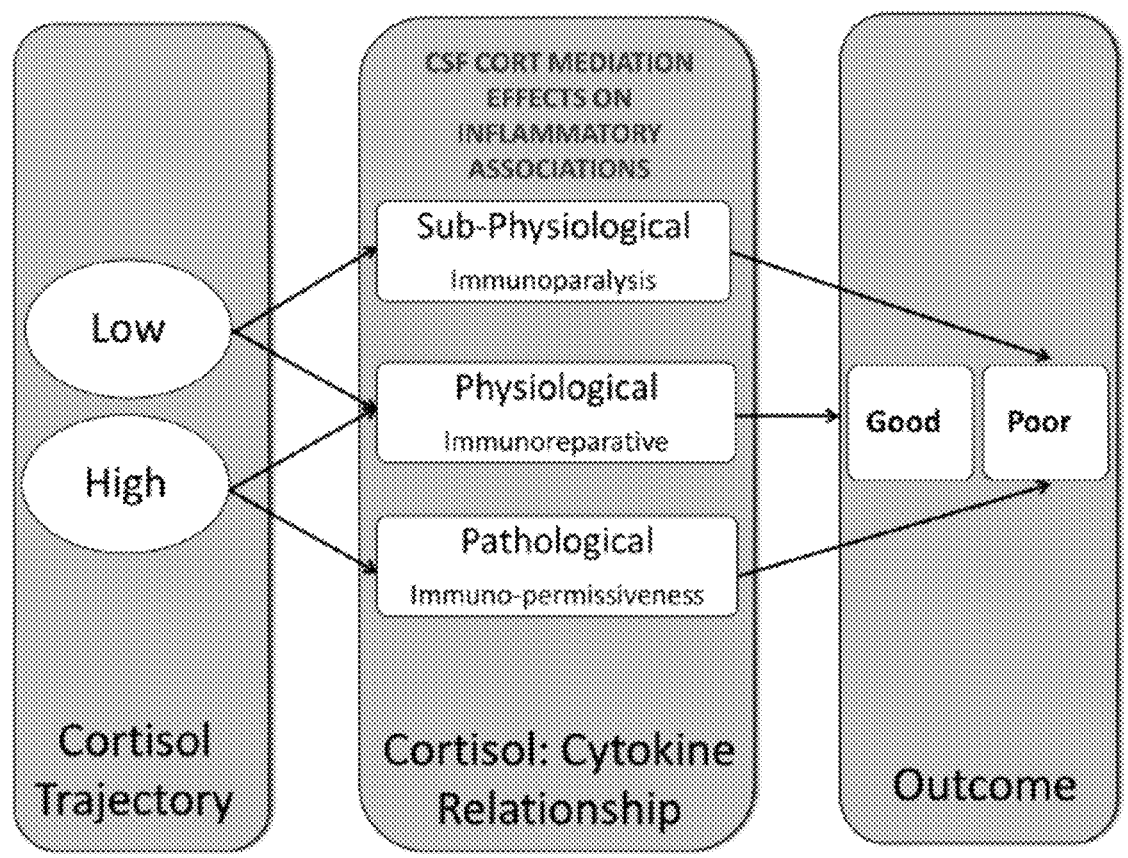
FIG. 2 depicts a scheme of the relationship between acute CSF inflammatory markers, cortisol trajectories, and 6-month outcome.
Figure 4:
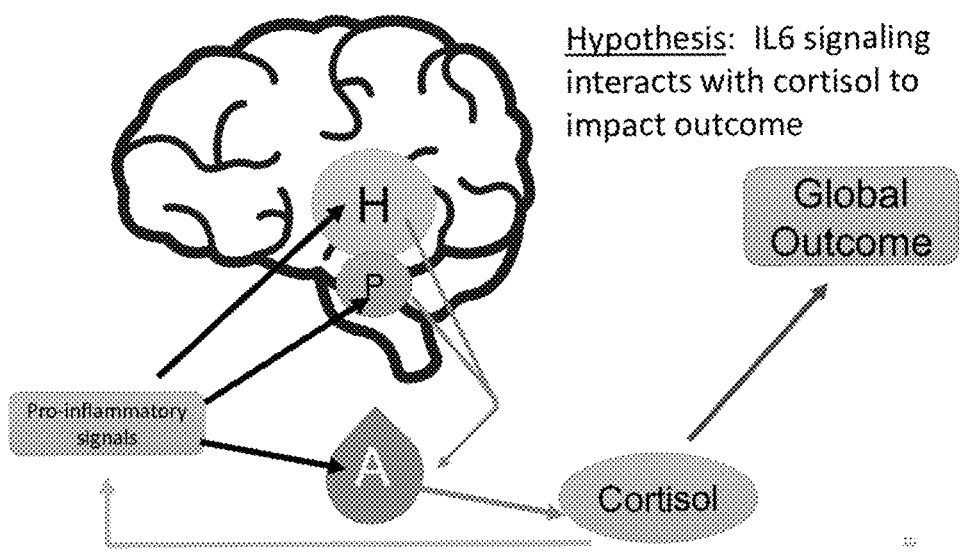
FIG. 4 depicts a scheme showing IL-6 signaling interacts with cortisol to impact outcome.

There is a bi-directional relationship between cortisol and inflammatory markers. A relationship was found between acute CSF inflammatory markers, cortisol trajectories, and 6-month outcome (FIG. 2). Serum and CSF cortisol levels are elevated early post TBI. Elevated chronic cortisol can exacerbate CNS inflammation. It was hypothesized that IL-6 signaling interacts with cortisol to impact outcome (FIG. 4).

Figure 3:
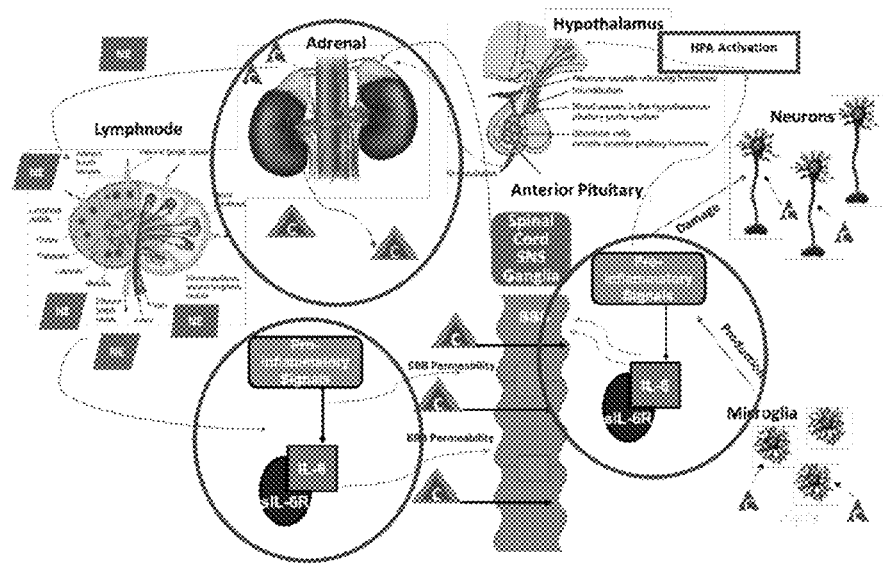
FIG. 3 depicts a scheme of proposed mechanism for IL-6 signaling and HPA Axis.

It was shown that HPA affected chronic IL-6 trans-signaling after TBI. The average posterior probability in each group ranged from 0.71 to 0.81 (FIG. 5A). Cortisol levels from 2-week-6-months post-injury are shown by cortisol TRAJ groups (FIG. 5B). Mediation to 12-month GOS showed that cortisol accounts for 45% of the relationship between IL6:sIL6R and 12-month outcome, suggesting chronic HPA axis regulated sIL-6R signaling impacted global outcome (FIGS. 3 and 6). The data suggests that stress reduction interventions like exercise/yoga might impact sIL-6R signaling and outcome.

The difference between classical signaling and trans-signaling is that classic signaling uses membrane bound receptors and trans-signaling uses soluble receptors (FIG. 7). IL-6 and its soluble receptor, sIL-6R, facilitate a signaling cascade predisposing individuals to a chronic inflammatory state. Soluble gp130 (sgp130) is a potent IL-6 inhibitory protein. Excess sgp130 restricts the expression of the IL-6/sIL-6R complex.

It has been hypothesized that peripheral and CNS sIL-6R signaling contributes to BBB permeability and failure to resolve the acute innate neuroinflammatory response that occurs after TBI. Thus, it is hypothesized sIL-6R signaling contributes to complication risk after TBI including for the development and persistence of post-traumatic headache, cognitive deficits, epilepsy, depression. Adverse effects of sIL-6R (trans-signaling) can be moderated by sgp130. SGP130 values (alone) or in combination with sIL-6R can be an effective biomarker discriminating complication (poor outcome) risk. SGP130 may be an effective immunotherapy for TBI repair and recovery.

Certain studies indicate that 18-58% of those suffering a TBI will have significant headache at 1 year following the trauma. Post-traumatic headache (PTH) is a predictor of overall outcome after concussion. PTH has features of migraine, and patients are commonly categorized by the presence or absence of these features. Family and premorbid history of migraine may increase risk for PTH. Significant positive correlation was detected between serum levels of ICAM1 and IL6 in migraine patients during attacks.

The study design was a prospective cohort study for individuals with moderate to severe TBI. Seventy-seven adults with moderate to severe TBI were recruited. Trajectory analysis was performed to track monthly headache symptoms over the first-year post-injury. Biomarker values for sgp130, IL-6, sIL-6R over first year post-injury were also measured. Descriptive statistics and multivariate ROC were performed. Longitudinal headache profile analysis showed two distinct groups with HA, and they looked similar at 3 months. But one group resolved and the other did not (FIG. 9). Headache status (%0 by month data is in line with other published data (FIG. 10). IL-6 levels are generally similar over time (FIG. 11). Higher sgp130 levels associated with resolve headache. Higher sgp130 levels over time were detected compared to resolve group (FIG. 12). Higher sIL-6R levels were associated with chronic headache, and significantly higher sIL6R levels were observed over time compared to low group (FIG. 13). TBI results in significantly Lower sgp130:sIl-6R ratios compared to controls (FIG. 14). sgp130:sIl-6R ratios over time by headache TRAJ groups showed clear differences in sgp130:sIl-6R ratios between those with chronic headache and those who resolve (FIG. 15). Sgp130:sIL-6R ratios were lower in the chronic headache group. There were no differences in Il-6 levels for these three groups. This indicated that the soluble receptor availability is the rate limiting determinant of headache outcome after TBI. sgp130:sIl-6R ratios were similar between resolve groups and uninjured controls, suggesting a compensatory SGP130 response to injury that reduces headache risk and symptoms over time (FIG. 16A). Cort may be a biomarker to supplement sgp130 prediction models for impairment and patient stratification purposes. Individuals with chronic headaches had higher CORT levels at quarters (Q) 1, 2, and 3. Individuals with headaches that later resolve had elevated CORT levels early (Q1) before having low CORT at Q2, 3, and 4.

A headache prediction model as shown in FIG. 17 was created. The prediction model took into account of age, sex (men=reference), GCS, pre-injury history of alcoholism (no=reference), and pre-injury history of headaches (no=reference) (OR=0.241; 95% CI: [0.087,0.669]p=0.006) (FIG. 17). The model yielded a 19% improvement in headache prediction with the biomarker sgp130:sIl-6R ratio (model with sgp130:sIL-6R with AUC 0.91) (FIG. 18). Predictive capacity for chronic PTH with ratio of 5.9 had sensitivity of 74.07 and specificity of 61.90 (FIG. 19). The data demonstrate that treatment can be considered for those having ratios lower than 5.9.

Cognitive impairment is a large contributor to chronic complications that persist years after traumatic brain injury (TBI). 65% of moderate to severe TBI patients report long-term problems with cognitive functioning. Cognitive deficits can have a profound long-term effect on survivor outcomes such as ability to return to work or school and live independently, ability to participate in relationships and leisure activities. Domains of executive function and memory are particularly vulnerable to injury.

CSF IL-6 family proteins were used in linear & log regression to assess 6-month overall composite scored as a preliminary study (FIG. 20). Also, a cognitive serum study was designed as a prospective cohort study for individuals with moderate to severe TBI. About 164 adults were recruited. Cognitive assessments were done at 6 months and 12 months after TBI. Biomarker values for sgp130, IL-6, sIL-6R were measured over first year post-injury. Statistical approach included descriptive statistics and multivariate ROC. Linear regression models of CSF sgp130:sIL-6R 6 and 12-month cognitive impairment predicted overall composite scores, particularly at 12 months post injury (FIG. 21). Logistic regression models of serum sgp130:sIL-6R predicted overall impairment scores at 6-months (FIG. 22). Logistic regression models of serum sgp130:sIL-6R ratios also predicted 12-month cognitive impairment scores (FIG. 23). An ROC curve demonstrating serum relationships cognition impairment status for 6 months and 12 months (FIGS. 24A-24B). A model adjusted for IL-6, sgp130-sIL-6R ratio, age, GCS, education and sex), and serum sgp130:sIL6R ratio associations in relationship to cognition scores (FIGS. 25A-25C) in the enrolled subjects. Higher sgp130/sIL-6R ratios largely were associated with less cognitive impairment.

Epilepsy and TBI. Seizures are the major cause of death in the TBI patient population. Individuals with TBI have a 50-times increased risk for dying from a seizure compared to heathy age, sex, and race-matched controls. Prognostic models have been generated to predict PTE risk for ~2000 individuals with moderate to severe TBI at both one and two years after injury. SDH, intra-parenchymal fragment, craniotomy, craniectomy, seizure during acute hospitalization, preinjury incarceration. IL-1β levels during acute care and IL-1β genetics were associated with time to first seizure after TBI. Acute seizures can increase IL-6 levels in serum. Consistently raising sgp130 levels for PTE patient may be a treatment or a preventative. Epilepsy study design was prospective cohort study for individuals with moderate to severe TBI. 124 adults were enrolled. Time to first seizure over the first 12 months post-injury was measured. Biomarker values for sgp130, IL-6, sIL-6R over first year post-injury were measured. Statistical approach included descriptive statistics, time to event analysis (Cox Regression), and ROC with logistic regression. IL-6 family biomarkers at month 0-3 by time until first seizure up to 1 year (FIG. 26), Cox proportional hazards regression on IL-6 family biomarkers at mo0-3 by time until first seizure to 1 year (FIG. 27A) were measured. measure over 0-6 month were compared by time until first seizure to 3 year (FIG. 27B) post injury. Cox proportional hazards regressions on mean IL-6 family biomarkers were measured. All biomarkers in this figure were standardized. As a result, effect sizes were interpreted as increased risk per 1 standard deviation increase. An epilepsy prediction ROC model was created (FIGS. 28A-28C, 1 year PTE (Y/N) Logistic Regression Model, months 0-3 sgp130+age, GCS compared to base model of age, GCS, SDH, and Depressed Skull Fx). The base model included covariates only. Model included covariates and month 0-6 sgp130 levels, demonstrating 2.8% improvement in area under ROC Curve, a measurement of the model's ability to accurately discriminate seizure status. An increase in one standard deviation of sgp130 (30,679 pg/mL) was associated with a 1.7× increase likelihood of seizure event.

Bio-susceptibility—depression after TBI. PTD is the most common psychological problem following TBI (Prevalence: 6-77%). PTD has been associated with poorer cognition, aggression, greater functional disability, poorer recovery and higher rates of suicide. Reduced effectiveness of SSRIs in PTD has been suggested in the context of increased inflammatory burden (Lanctot 2010). Interleukin-6 (IL-6) has emerged as a potent biomarker for depression as it is elevated plasma for patients with clinical depression: findings confirmed by meta-analyses. The presently disclosed PTD biomarker studies showed acute CSF sICAM, sVCAM, sFas were associated with PTD at 6-months. Acute CSF IL-7, IL-8 were associated with PTD at 12 months. Serum BDNF levels at 6-month and 12-month were associated with PTD at 6 and 12-months.

Post-traumatic depression and soluble IL-6R signaling study was conducted. The study was designed as a prospective cohort study for individuals with moderate to severe TBI. About 155 adults were enrolled. Trajectory analysis was conducted to track monthly depressive symptoms over the first-year post-injury. PTD Status at 6 and 12 months post-injury was measured. Premorbid depression covariate was measured. Biomarker values for sgp130, IL-6, sIL-6R over first year post-injury were measured. Statistical approach included descriptive statistics, and multivariate Regression and ROC. IL-6, sIL-6R, and sgp130 by 12 month PTD status (FIGS. 29A-29C), linear regression PHQ-9 scores 12-months (FIG. 30), logistic regression PHQ-9 impaired status 12-months (FIG. 31), linear regression to 12-months PHQ-9 total scores (FIG. 32), mean IL-6 at 0-3 months stratified by sgp130 and PTD status at 12-months (FIG. 33) were measured. The data showed that depression is associated with higher IL-6 levels in the setting of low SGP130 levels, suggesting treating people with sgp130 below threshold of 130K pg/mL and increased IL-6 levels. Similar results were obtained when removing people who had pre-morbid depression and the model rerun for sensitivity analysis (FIG. 34).

The present disclosure showed that chronic sgp130 levels (when in a ratio with sIL-6R or when sgp130 is considered in the context of IL-6 levels and/or sIL-6R levels) is a promising marker for predicting risk for multiple chronic conditions, including PTH, PTD, cognitive impairments, and epilepsy. Sgp130 can be used as a treatment intervention. Certain studies report a molar excess of sgp130 restricts the expression of the IL-6/sIL-6R complex (Chalaris et al., Eur. J. Cell Biol. 90, 484-494 (2011); Atreya, et al., Nat. Med. 6, 583-588 (2000); Campbell et al., J. Neurosci. Off. J. Soc. Neurosci. 34, 2503-2513 (2014)). Spg130 treatment is tested in the presently disclosed mouse and rat CCI models.

In silico modeling work using biomathematical approach for temporal dynamics and intervention simulation. These results implicate IL-6 signaling cascades as key determinants of the course of inflammation and recovery.

In silico models are being created to delineate the inhibitory effects of sgp130 on the IL-6/sIL-6R complex and inflammatory interactions that lead to IL-6 classical vs. trans-signaling cascades. Differential equation modeling and other mathematical and machine learning techniques will integrate biological mechanisms involving these inflammatory mediators and provide insight on their temporal dynamics in the context of the cytokine microenvironment. The role of IL-6 trans-signaling and BBB break down is also being explored using an in silico approach.

As a therapeutic agent, sgp130 can mitigate the adverse effects of IL-6/sIL-6R. In Crohn's Disease, high plasma sgp130 can specifically block sIL-6R dependent IL-6 actions. Responses via the membrane bound IL-6R remain unaffected. Both in vitro and in vivo inflammatory models show trans-signaling inhibition with administration of an fc dimerized version of sgp130 (sgp130fc). sgp130fc caused suppression of colitis activity and apoptosis in patients with Crohn's Disease. STAT3 phosphorylation, a major signal transducer downstream of the initial IL-6/sIL-6R complex formation, decreased after administration of recombinant sgp130 in mice with hepatocellular carcinoma.

The presently disclosed studies have also tested spg130 as treatment in mice and rat. CCI mice N=36 (severe) and sham with vehicle or sgp130 Rx 3 week study was performed. Novel object behavior, Morris water maze, and flow cytometry were performed. Blood was collection at sac, IL-6, sIL-6R, and sgp130 were measured. Brain was harvested, and ELISA on IL-6, sIL-6R, sgp130 was performed. N=24 rat CCI (severe) and sham with vehicle or sgp130 Rx 1 week study was performed. Motor testing, AST, and Y-maze were measured. Blood was collected and ELISA on IL-6, sIL-6R, sgp130 were measured. Brain was harvested, and ELISA on IL-6, sIL6R, sgp130 were measured.

Example 2: IL-6 Signaling in TBI

The secondary injury response after traumatic brain injury (TBI) is characterized by an acute innate immune response. Certain work has begun to identify potential sub-acute (2 weeks-3 months post-injury) peripheral inflammatory markers that influence long-term global outcome. Specifically, it has been shown that pro-inflammatory mediators, including interleukin (IL) 6 in the sub-acute phase, are associated with worse global outcomes at 6 and 12 months moderate to severe TBI (Kumar et al., J Head Trauma Rehabil. 2015 November-December; 30(6):369-81). Cytokine receptors, specifically for IL-6, exist both in membrane-bound form to a variety of target tissues and in soluble form. The soluble receptors of the IL-6 family include soluble IL-6R (sIL-6R) and soluble IL-11R. IL-6 binding to its membrane bound receptor is termed classical signaling (Rose-John et al., J Leukoc Biol. 2006 August; 80(2):227-36; Morieri et al., Mediators Inflamm. 2017, U.S. Pat. No. 1,396,398 (2017)). Cells expressing the membrane bound receptor, once bound by IL-6, form a signaling complex with membrane-bound glycoprotein (gp130) (Morieri et al., Mediators Inflamm. 2017, U.S. Pat. No. 1,396,398 (2017)), which can have anti-inflammatory effects. Interestingly, certain work suggests IL-6 bound to sIL-6R potentially perpetuates individuals into a chronic inflammatory state (Rose-John et al., J Leukoc Biol. 2006 August; 80(2):227-36) through an alternative pro-inflammatory trans-signaling pathway. Importantly soluble gp130 (sgp130) has inhibitory effects on the IL-6/sIL-6R complex, such that when bound to sgp130, can attenuate these trans-signaling induced IL-6 cascades. Blockade of this trans-signaling pathway may be an important mechanism (therapeutic target) by which to resolve persistent inflammation and reduce poor global outcome among individuals with moderate to severe TBI. Certain studies report a molar excess of sgp130 restricts the expression of the IL-6/sIL-6R complex (Rose-John et al., J Leukoc Biol. 2006 August; 80(2):227-36; Jostock et al., Eur. J. Biochem. 268, 160-167 (2001); Rose-John et al., Immunity 20, 2-4 (2004)), identifying the need to elucidate the regulatory mechanisms of sgp130 to the IL-6 cytokine family and its influence on outcome.

Certain in vitro and in vivo studies using various inflammatory models report specific inhibition of trans-signaling with an fc-dimerized version of sgp130 (sgp130fc) (Matsumoto et al., J. Immunol. Baltim. Md 1950 184, 1543-1551 (2010); Hong et al., Sci. Rep. 6, 24397 (2016); Chalaris et al., Eur. J. Cell Biol. 90, 484-494 (2011); Allocca et al., Curr. Drug Targets 14, 1508-1521 (2013); Calabrese et al., Nat. Rev. Rheumatol. 10, 720-727 (2014); Atreya et al., Nat. Med. 6, 583-588 (2000); Campbell et al., J. Neurosci. Off. J. Soc. Neurosci. 34, 2503-2513 (2014)). sgp130fc caused suppression of colitis activity and induction of apoptosis in patients with Crohn's Disease (Atreya et al., Nat. Med. 6, 583-588 (2000). Additionally, one study conducted in mice with hepatocellular carcinoma (HCC) examined how IL-6 trans-signaling affects STAT3 phosphorylation, a major signal transducer downstream of the initial IL-6/sIL-6R complex formation, after recombinant sgp130 administration (Hong et al., Sci. Rep. 6, 24397 (2016)). In this study, recombinant sgp130 significantly decreased IL-6 induced STAT3 phosphorylation. Further, the results from this study also indicate that recombinant sgp130 is capable of inhibiting tumor growth. Against this background, the disclosed subject matter considered that sgp130 may be a promising new biological target for resumption of chronic inflammation through inhibition of IL-6 trans-signaling in the context of severe TBI.

Methods

Serial serum samples were collected from N=86 individuals with severe TBI from 2 weeks-3 months post-injury and assessed sgp130, IL-6, and sIL-6R levels. Monthly ratios were produced for IL-6:sIL-6R and sgp130:sIL-6R. Median and mean levels were calculated for values obtained from samples collected 2 weeks-3 months for each of the biomarkers and for the ratios. Clinical outcomes, including the Disability Rating Scale (DRS) and the Glasgow Outcome Scale (GOS), were collected at both 6 and 12 months post-injury. Biomarker data were deciled for multivariate analyses. GOS was dichotomized to reflect a poor (GOS=2/3) vs. good (GOS=4/5) outcome for GOS scores obtained at 6 and 12-month. DRS was categorized into three groups, 1) good (DRS=0-3), 2) moderate (DRS=4-14), and 3) poor (DRS=15-29) for both 6 and 12-month scores (Kumar et al., Brain Behav Immun. 2016 March; 53:183-193).

Logistic regression was conducted for GOS as the outcome variable, and ordinal logistic regression was conducted for DRS as the outcome variable. Proportionality assumptions were met for all ordinal logistic regression models. All variables were tested for interactions before inclusion in the multivariate analysis.

Results

Biomarker data for 2 weeks-3 month averages were not predictive of outcomes at 6 months. However, significant findings for 12-month outcomes are provided in Tables 1-2.

Table 1 shows that higher levels of IL-6 and its receptor are with worse outcome, while higher levels of sgp130 are associated with better outcome. Table 1 also suggests that higher ratios (i.e. higher sgp130 and lower sIL6R) are associated with better outcome. Table 2 models shows similar results with an alternative global outcome tool.

TABLE 1

Multivariate models for 12-month DRS
(Modeled towards Poor Outcome)

| Multivariate Model | OR(95% CI) | P value |
|---|---|---|
| Age | 0.961 (0.920, 1.003) | 0.0697 |
| Gender | 0.277 (0.074, 1.042) | 0.0575 |
| sgp130 (2 wk-3 mo) | 0.806 (0.650, 1.001) | 0.0507 |
| IL6 (2 wk-3 mo) | 1.514 (1.201, 1.908) | 0.0004 |
| IL6R (2 wk-3 mo) | 1.274 (1.201, 1.908) | 0.0267 |
| Age | 0.964 (0.925, 1.005) | 0.0832 |
| Gender | 0.269 (0.072, 0.998) | 0.0497 |
| sgp130:sIL6R Ratio (2 wk-3 mo) | 0.817 (0.675, 0.989) | 0.0382 |
| IL6 (2 wk-3 mo) | 1.539 (1.220, 1.941) | 0.0003 |

TABLE 2

Multivariate models for 12-month GOS
(Modeled towards Poor Outcome)

| Multivariate Model | OR(95% CI) | P value |
|---|---|---|
| Age | 0.980 (0.941, 1.020) | 0.3209 |
| Gender | 0.191 (0.048, 0.750) | 0.0177 |
| sgp130 (2 wk-3 mo) | 0.818 (0.653, 1.026) | 0.0821 |
| IL6 (2 wk-3 mo) | 1.332 (1.066, 1.664) | 0.0118 |
| IL6R (2 wk-3 mo) | 1.241 (0.992, 1.552) | 0.0593 |
| Age | 0.982 (0.943, 1.021) | 0.3549 |
| Gender | 0.174 (0.044, 0.695) | 0.0133 |
| sgp130:sIL6R Ratio (2 wk-3 mo) | 0.802 (0.653, 0.985) | 0.0358 |
| IL6 (2 wk-3 mo) | 1.364 (1.087, 1.712) | 0.0073 |

These results suggest that subacute peripheral markers have a significant predictive capacity for long-term clinical outcomes. Interestingly, sgp130:sIL-6R ratios and IL-6 independently predict 12-month outcomes for DRS and GOS at 12 months post-injury. The odds ratio of <1 for sgp130:sIL-6R ratios in both models suggest that with increasing sgp130:sIL-6R ratios, an individual has greater odds of experiencing good outcome. These results suggest that molar excess of sgp130 in patients with severe TBI may have a protective capacity and resolve chronic inflammation and are worth exploring in preclinical models as well as simulating in in silico models that were generated to reflect chronic inflammatory processes after TBI.

FIGS. 35-38 depict sgp130:sIL-6R levels by outcome. Mean sgp130:sIL-6R levels have a decreasing trend with more severe injuries, identifying that higher sgp130 levels relative to sIL-6R may be protective in the context of TBI.

Discussion

IL-6 signaling has been shown to have pleiotropic functions. Certain studies show IL-6 protects against septic shock and directs resolution of acute inflammation, potentially through the role of IL-6 classical signaling (Barton et al., Infect. Immun. 61, 1496-1499 (1993)). However, cytokines of the IL-6 family elicits a detrimental response in the context of chronic inflammation through uncontrolled trans-signaling. This work begins to identify that the preferential binding of sgp130 to the IL-6/sIL-6R complex may selectively block progression of inflammation through the inhibition of IL-6 signaling by the sIL-6R after severe TBI, as higher relative relationship between sgp130:sIL-6R impacts outcomes at 12-months. These results have implications for understanding how sgp130 potentially serves as a modifiable target for prevention and/or resolution of chronic inflammation post-TBI. sgp130 may be a more selective modifiable target than IL-6R antagonists which bind both soluble and membrane bound receptors (Maes et al., Expert Opin. Ther. Targets 18, 495-512 (2014)), particularly at low dose (Garbers et al., J. Biol. Chem. 286, 42959-42970 (2011)).

Example 3: Sgp130 Moderates the Relationship Between Chronic IL-6/sIL-6R Complex in Differentiating Outcome after Severe TBI Biomarker data were deciled for multivariate analyses. GOS was dichotomized to reflect a good (GOS=4/5) vs. poor (GOS=2/3)) outcome for scores obtained at 6 and 12 months. DRS was categorized into three groups, 1) good (DRS=0-3), 2) moderate (DRS=4-14), and 3) poor (DRS=15-29) for both 6 and 12-month scores. Simple logistic regression was conducted for GOS as the outcome variable, and ordinal logistic regression was conducted for DRS as the outcome variable. Proportionality assumptions were met for all ordinal logistic regression models. All variables were tested for interactions before inclusion in the multivariate analyses. Demographic and injury characterization of population by 12-month GOS are shown in Tables 3 and 4.

TABLE 3

Demographical and injury characterization of population by 12-month GOS

| Variable | 12-Month GOS Good (n = 62) | 12 Month GOS Poor (n = 20) | P value |
|---|---|---|---|
| Age, Mean (SE) | 37.08 (2.17) | 32.30 (2.86) | p = 0.3176 |
| Sex, Men (%) | 54 (87.10) | 13 (65.00) | p = 0.0430 |
| Race, n (%) | | | p = 0.0850 |
| Caucasian | 57 (75.61) | 17 (85.00) | |
| African-American | 5 (8.06) | 1 (5.00) | |
| GCS best in 24, Median (IQR) | 8 (3.5) | 6 (2) | p = 0.0234 |
| ISS, Mean (SE) | 31.13 (1.55) | 39.11 (2.73) | p = 0.0160 |
| Length of Stay, Mean (SE) | 18.26 (1.45) | 28.76 (3.69) | p = 0.0017 |
| MOI, n (%) | | | |
| MVA | 18 (45.00) | 9 (50.00) | |
| Fall/jump | 6 (15.20) | 1 (5.56) | |
| Assault/fight | 0 (0.00) | 1 (5.56) | |
| Truck | 1 (2.50) | 0 (0.00) | |
| Bus | 1 (2.50) | 0 (0.00) | |
| Off-road vehicle | 4 (10.00) | 2 (11.11) | |
| Motorcycle | 9 (22.50) | 3 (16.67) | |
| Bicycle | 1 (2.50) | 1 (5.56) | |
| Other | 0 (0.00) | 1 (5.56) | |
| Injury Type, n (%) | | | |
| SDH | 26 (66.67) | 11 (61.11) | p = 0.6829 |
| SAH | 21 (53.85) | 15 (83.33) | p = 0.0319 |
| DAI | 12 (30.77) | 5 (27.78) | p = 0.8185 |
| EDH | 7 (17.95) | 3 (16.67) | p = 0.9058 |
| Contusion | 16 (41.03) | 6 (33.33) | p = 0.5792 |
| IVH | 7 (17.95) | 3 (16.67) | p = 1.0000 |
| ICH | 12 (30.77) | 9 (50.00) | p = 0.1618 |
| Other | 1 (2.56) | 1 (5.56) | p = 0.5357 |

TABLE 4

Demographical and injury characterization of population by 12-month DRS

| Variable | 12-Month DRS Good (n = 56) | 12-Month DRS Moderate (n = 20) | 12-Month DRS Poor (n = 5) | P value |
|---|---|---|---|---|
| Age, Mean (SE) | 38.27 (2.33) | 31.6 (2.93) | 27.00 (2.77) | p = 0.1577 |
| Sex, Men (%) | 49 (87.10) | 12 (60.00) | 5 (100.00) | p = 0.0252 |
| Race, n (%) | | | | p = 0.1248 |
| Caucasian | 51 (97.07) | 18 (90.00) | 4 (80.00) | |
| African-American | 5 (8.93) | 1 (5.00) | 0 (0.00) | |
| GCS best in 24, Median (IQR) | 8 (5) | 7 (3) | 6 (0) | p = 0.0072 |
| ISS, Mean (SE) | 31.45 (1.74) | 37.22 (2.70) | 34.80 (6.20) | p = 0.3219 |
| Length of Stay, Mean (SE) | 16.76 (1.10) | 27.61 (3.65) | 33.00 (8.80) | p = 0.0038 |
| MOI, n (%) | | | | |
| MVA | 16 (47.06) | 8 (44.44) | 3 (60.00) | |
| Fall/jump | 5 (14.71) | 0 (0.00) | 1 (20.00) | |
| Assault/fight | 0 (0.00) | 1 (5.56) | 0 (0.00) | |
| Truck | 0 (0.00) | 1 (5.56) | 0 (0.00) | |
| Bus | 0 (0.00) | 1 (5.56) | 0 (0.00) | |
| Off-road vehicle | 4 (11.56) | 2 (11.11) | 0 (0.00) | |
| Motorcycle | 8 (23.53) | 3 (16.67) | 1 (20.00) | |
| Bicycle | 1 (2.94) | 1 (5.56) | 0 (0.00) | |
| Other | 0 (0.00) | 1 (5.56) | 0 (0.00) | |
| Injury Type, n (%) | | | | |
| SDH | 22 (66.67) | 11 (61.11) | 3 (60.00) | p = 0.9162 |
| SAH | 19 (57.58) | 12 (66.67) | 4 (80.00) | p = 0.6489 |
| DAI | 11 (33.33) | 4 (22.22) | 2 (40.00) | p = 0.6111 |
| EDH | 6 (18.18) | 3 (16.67) | 1 (20.00) | p = 1.0000 |
| Contusion | 13 (39.39) | 5 (27.78) | 3 (60.00) | p = 0.4457 |
| IVH | 6 (18.18) | 3 (16.67) | 1 (20.00) | p = 1.0000 |
| ICH | 12 (36.36) | 8 (44.44) | 1 (20.00) | p = 0.7065 |
| Other | 1 (3.03) | 1 (5.56) | 0 (0.00) | p = 1.0000 |

Logistic regression models showed that biomarker data for 2 weeks-3 months averages were not predictive of outcomes at 6 months. However, significant findings for 12-month outcomes were observed and are shown in Tables 5 and 6.

TABLE 5

Multivariate models for 12-month DRS

| Multivariate Model (N = 81) | OR (95% CI) | P value |
|---|---|---|
| Age | 0.961 (0.920, 1.003) | 0.0697 |
| Sex (Reference = Male) | 3.609 (0.960, 13.574) | 0.0575 |
| sgp130 | 0.806 (0.650, 1.001) | 0.0507 |
| IL6 | 1.514 (1.201, 1.908) | 0.0004 |
| SIL6R | 1.274 (1.028, 1.579) | 0.0267 |
| Age | 0.964 (0.925, 1.005) | 0.0832 |
| Sex (Reference = Male) | 3.719 (1.002, 13.805) | 0.0497 |
| sgp130:sIL6R Ratio | 0.817 (0.675, 0.989) | 0.0382 |
| IL6 | 1.539 (1.220, 1.941) | 0.0003 |

TABLE 6

Multivariate models for 12-months GOS

| Multivariate Model (N = 82) | OR (95% CI) | P value |
|---|---|---|
| Age | 0.980 (0.941, 1.020) | 0.3209 |
| Sex (Reference = Male) | 5.247 (1.333, 20.646) | 0.0177 |
| sgp130 | 0.818 (0.653, 1.026) | 0.0821 |
| IL6 | 1.332 (1.066, 1.664) | 0.0118 |
| SIL6R | 1.241 (0.992, 1.552) | 0.0593 |
| Age | 0.982 (0.943, 1.021) | 0.3549 |
| Sex (Reference = Male) | 5.734 (1.439, 22.842) | 0.0133 |
| sgp 130: sIL 6R Ratio | 0.802 (0.653, 0.985) | 0.0358 |
| IL6 | 1.364 (1.087, 1.712) | 0.0073 |

Sub-acute peripheral markers had a significant predictive capacity for long-term clinical outcomes. sgp130:sIL-6R ratios & IL-6 independently predicted 12-month outcomes for DRS and GOS. The odds ratio of <1 for sgp130:sIL-6R ratios in both models indicated increased sgp130:sIL-6R ratios are linked with greater odds of experiencing good outcome. In both models, women have increased odds for experiencing poor outcome.

Post-Hoc analysis of sgp130: sIL-6R ratios by outcome group were shown in FIGS. 37-38. sgp130:sIL-6R ratios decreased with more severe injuries, providing evidence that higher sgp130 levels, relative to sIL-6R, may be protective in the context of TBI.

Certain pro- and anti-inflammatory cytokines have been studied in the acute phase after TBI. Certain work has identified several serum cytokines that are elevated in the first year post-injury. Serum IL-1β, IL-6, IL-8, IL-10, and TNFα levels are all elevated chronically. High pro-inflammatory burden with IL-6, relative to anti-inflammatory IL-10 is significantly associated with worse global outcome. IL-6 signaling has pleiotropic inflammatory functions. IL-6 protects against septic shock and directs resolution of acute inflammation. However, IL-6 family cytokines elicit a detrimental response in the context of trans-signaling and chronic inflammation. Specifically, chronic serum IL-6 signaling is a dominant mechanism for pathogenic roles on BBB disruption after injury and may potentially be an indicator of IL-6 trans-signaling occurring within the brain.

sgp130 can mitigate the adverse effects of IL-6/sIL-6R. In Crohn's Disease, high plasma sgp130 can specifically block sIL-6R dependent IL-6 actions. Responses via the membrane bound IL-6R remain unaffected. Both in vitro and in vivo inflammatory models show trans-signaling inhibition with administration of an fc dimerized version of sgp130 (sgp130fc). sgp130fc caused suppression of colitis activity and apoptosis in patients with Crohn's Disease. STAT3 phosphorylation, a major signal transducer downstream of the initial IL-6/sIL-6R complex formation, decreased after administration of recombinant sgp130 in mice with hepatocellular carcinoma.

This study begins to characterize both sgp130 and IL-6/sIL-6R in a clinical population with TBI. sgp130:sIL-6R ratios influence global outcome by attenuating the IL-6/sIL-6R complex. It was hypothesized that the preferential binding of sgp130 to sIL-6R selectively blocks progression of inflammation by inhibiting IL-6-sIL-6R trans-signaling after severe TBI. These results have novel implications for how sgp130 potentially serves as a modifiable target for prevention and/or resolution of chronic inflammation post-TBI. IL-6-sIL-6R binding elicits a detrimental response in the context of chronic inflammation through uncontrolled trans-signaling.

Example 4: Sgp130 Moderates the Relationship Between Chronic IL-6sIL-6R Complex in Differentiating Outcome after TBI Group-based Trajectory (TARJ) analysis was conducted to measure endogenous sgp130 and sIL-6R levels. sgp130 is implicated in protection against detrimental trans-signaling while sIL-6R was implicated in trans-signaling. Group-based TRAJ analysis of IL-6 family soluble receptor molecules revealed that there are subpopulations with differential expression of IL-6 signaling molecules which modulate its bioactivity (FIGS. 39A-39B, Table 7).

TABLE 7

Group-based TRAJ analysis for sgp130a and sIL-6R

| | n (% of Cohort) | Posterior Probability |
|---|---|---|
| sgp 130 TRAJ Group | | |
| LOW | 90 (50.8) | 0.9308 |
| HIGH | 86 (49.2) | 0.9355 |
| SIL-6R TRAJ Group | | |
| LOW | 80 (44.9) | 0.9656 |
| HIGH | 98 (55.1) | 0.9564 |

The expression levels of soluble receptors-sgp130 and sIL-6R were then integrated into a ratio to represent that relative balance of classical vs. trans-signaling and regulatory capacity of sgp130 on sIL-6R (FIG. 40, Table 8). Group-based TRAJ analysis measured endogenous low and high profiles of sgp130:sIL-6R ratios, which serve as a joint metric to gauge degree of trans & classical signaling that has ensued. The sgp130:sIl-6R ratio can be a stratification method for patient outcome prognostication. TRAJ analysis of sgp130:sIL-6R ratio yielded two distinct groups: one persisting at below control levels of 6.5 and one above. Separating two groups with a cut-point ratio of 6.5 became relevant later to delineate chronic outcomes.

TABLE 8

Group-based TRAJ analysis for sgp 130a:sIL-6R ratio

| sgp130:sIL-6R TRAJ Group | n (% of Cohort) | Posterior Probability |
|---|---|---|
| LOW | 81 (47.2) | 0.9772 |
| HIGH | 95 (52.8) | 0.9588 |

When sIL-6R expression level was lower than 22000 pg/mL, a characteristic of the low TRAJ, a moderately strong positive correlation with sgp130 expression to regulate its activity was observed. In contrast, when sIL-6R exceeds this threshold, a characteristic of the high TRAJ, a significant rise in sgp130 to the same degree was not observed. This correlational data suggests that with excess sIL-6R bioavailability, intervention with supplemental sgp130 may be needed to mitigate trans-signaling that may ensue.

IL-6 levels were not directly correlated with either soluble molecule, sgp130 or sIL-6R. This implies that complex regulatory mechanisms may exist to modulate IL-6 bioactivity and that the expression level of an IL-6 soluble receptor (either sIL-6R or sgp130) is not at a 1:1 ratio with that of IL-6 itself. This implicates differential signaling by IL-6 to a variety of target cells in the TBI injury response. This finding also suggests a shift in soluble receptor signaling and complex formation of IL-6 and its family of soluble receptor molecules.

Stratified inflammatory profiles of low and high sIL-6R groups and low and high sgp130:sIL-6R groups were analyzed (FIG. 41). High sIL-6R TRAJ individuals experienced significantly higher rates of high NLR, headache, and also overall cognitive impairment. sgp130 as an independent TRAJ metric was not significantly concordant to unfavorable acute and chronic phenomena event ratios. sgp130:sIL-6R ratio has greater capacity than sgp130 alone to differentiate some chronic outcomes including headache specifically. This ratio is also the chronic readout of lymphopenia and neutrophilia experienced acutely. Specificity to headache post-TBI may be due to the well-known relationships between IL-6 and migraine associated with blood brain barrier dysfunction. Chronic sIL-6R sgp130:sIL-6R profiles can serve as (1) an indicator of IL-6 interactions (classical & trans-signaling) and (2) an additional inflammatory predictor for outcomes including: PTD, cognitive impairment, headache, seizure.

Chronic inflammation treelet analysis was produced (FIG. 42). This treelet did not include sIL-6R or sgp130 to eliminate weight contribution to associated treelet cluster scores. Over the first 6 months following TBI, serum inflammatory marker production clusters into unique expression patterns that map to five main areas of immunity. The specific cohort (n=165) this analysis pertained to the data available for 0-6-month post-TBI. Means were available for all 31 inflammatory markers in serum. Metrics contained 5 clusters optimized with a cut-point of 15.

Individual Treelet Cluster (TC) scores representing components of immunity and their breakdown by "treatment group" were also measured and presented (FIGS. 43A-43B). The high sIL-6R TRAJ and low sgp130:sIL-6R ratio TRAJ, a proposed risk profile, associated with significantly elevated soluble receptor expression as shown by higher mean TC3 scores. All other TC scores were non-significant by sIL-6R and sgp130:sIL-6RTRAJ. Notably, only the TC4 is related to sIL-6R and sgp130:sIL-6R ratios and represent soluble receptor related immune response. And all TC scores were not significant by spg130 TRAJ. IL-6 levels by sIL-6R TRAJ Group at 6 months post-injury (FIG. 43C) were measured. IL-6 levels in low TRAJ Group were varied (FIG. 43C). IL-6 levels by sgp130:sIL-6R TRAJ Group at 6 months post-injury (FIG. 43D) were also measured but there was no significant difference, which demonstrated the buffering effect of sgp130 on IL-6 relationships to sIL-6R levels. The cortisol levels by sIL-6R TRAJ Group (FIG. 43E) and by sgp130: sIL-6R TRAJ Group (FIG. 43F) were measured, but no significant difference was observed.

Example 5: Targeting Soluble IL-6 Receptor Signaling to Alleviate Chronic Conditions Post-TBI It was shown that peripheral and CNS sIL-6R signaling contributes to BBB permeability and failure to resolve the acute innate neuroinflammatory response that occurs after TBI. It was also shown that sIL-6R signaling contributes to complication risk after TBI including for the development and persistence of Post-traumatic Headache, Cognitive Deficits, Epilepsy, Depression. It was hypothesized that (1) adverse effects of sIL-6R (trans-signaling) can be moderated by sgp130; (2) sgp130 expression level alone or in combination with sIL-6R can be an effective biomarker discriminating complication (poor outcome) risk; and (3) sgp130 may be an effective immunotherapy for TBI repair and recovery.

The study (1) identified risk groups for Headache, depression, cognitive dysfunction, seizure using sgp130/sIL6R, (2) used the sgp130:sIL6R and/or sIL-6R to generate a biomarker cut point to treat patients at risk for headache, depression, cognitive dysfunction, seizure and (3) used sgp130 as a treatment affecting behavioral performance after experimental TBI in rodents and modifying IL-6 family biomarker levels.

Headache and TBI. The relationship between headache and soluble IL-6R signaling was investigated. Certain studies have indicated that 18-58% of those suffering TBI would have significant headache at 1 year following the trauma. And post-traumatic headache (PTH) is a predictor of overall outcome after concussion. PTH has features of migraine, and patients are commonly categorized by the presence or absence of these features. Family and premorbid history of migraine may increase risk for PTH. The prospective cohort study for individuals with moderate to severe TBI was conducted. Seventy-seven adults with moderate and severe TBI were tested. Group-based TRAJ analysis was used to track monthly headache symptoms over the first-year post-injury. Biomarker values for sgp130, IL-6, sIL-6R over first year post-injury were measured. Descriptive statistics and multivariate ROC were employed to analyze the data.

Longitudinal headache profile analysis showed two distinct groups with HA, and they looked similar at 3 months. But one group resolved and the other did (FIG. 9). sgp130: sIL-6R ratios over time by headache TRAJ groups showed clear differences in sgp130:sIL-6R ratios between those with chronic headache and those who resolve (FIG. 15). Chronic headaches associated with a sgp130:sIL-6R ratio of less than 6.5. This indicates that the soluble signaling pathways play an important role here. sgp130:sIL-6R ratios were similar between resolve groups and uninjured controls (FIG. 16). Resolvers generally are similar to other groups demographically. A headache prediction model as shown in FIG. 17 was created. The model took into account age, sex (men=reference), GCS, pre-injury history of alcoholism (no=reference), and pre-injury history of headaches (no=reference)(OR=0.241; 95% CI: [0.087,0.669]p=0.006)

(FIG. 17). The model has 19% improvement in headache prediction with the biomarker sgp130:sIL-6R ratio (model with sgp130:sIL-6R with AUC 0.91).

Cognitive impairment and TBI. The cognitive serum study was designed as a prospective cohort study for individuals with moderate to severe TBI. About 164 adults were recruited. Cognitive assessments were done at 6 months and 12 months after TBI. Biomarker values for sgp130, IL-6, sIL-6R were measured over first year post-injury. Statistical approach included descriptive statistics and multivariate ROC. Logistic regression 6-month overall cognitive impairment (FIG. 22) was measured. Higher sgp130:sIL-6R ratios equal more mild impairment and high IL-6 levels indicates more severe impairment. Injury severity and years of education are typical factors impacting cog impairment, despite these impairments already being adjusted for age, sex, and education as a part of the composite scoring strategy. Serum sgp130:sIL-6R ratio associations with cognition (FIGS. 25A-25C) were measured in the enrolled subjects. The cut point for sgq130:sIL-6R was about 6.5. A sgp130:sIL-6R cut point of 6.5 remains relevant in differentiating cognitively impaired from unimpaired TBI populations, and is easily contextualized as ratio level of controls. The overall cognitively impaired group was below sgp130:sIL-6R control ratio of 6.5 especially during Q1. Those without overall cognitive impairment were closer to control levels of sIL-6R (22,000 pg/ml) especially during Q1 (FIG. 25D).

Epilepsy and TBI. Seizures are the major cause of death in the TBI patient population. Individuals with TBI have a 50-times increased risk for dying from a seizure compared to heathy age, sex, and race-matched controls. Certain work has involved generating prognostic models to predict PTE risk for ~2000 individuals with moderate to severe TBI at both one and two years after injury. SDH, intra-parenchymal fragment, craniotomy, craniectomy, seizure during acute hospitalization, preinjury incarceration. IL-1β levels during acute care and IL-1β genetics were associated with time to first seizure after TBI. Acute seizures can increase IL-6 levels in serum. Consistently raising sgp130 levels for PTE patient may be a treatment or a preventative. Cox proportional hazards regression on IL-6 family biomarkers at month 0-3 by time until first seizure to 1 year (FIG. 27) were measured. Models were adjusted for craniectomy and/or craniotomy. Epilepsy prediction model was created (FIG. 28, 1 year PTE (Y/N) Logistic Regression Model, month 0-3 sgp130+age, GCS compared to base model of age, GCS, SDH, and Depressed Skull Fx).

Biosusceptibility—depression after TBI. PTD is the most common psychological problem following TBI (Prevalence: 6-77%). PTD has been associated with poorer cognition, aggression, greater functional disability, poorer recovery and higher rates of suicide. Reduced effectiveness of SSRIs in PTD has been suggested in the context of increased inflammatory burden. Interleukin-6 (IL-6) has emerged as a potent biomarker for depression as it is elevated plasma for patients with clinical depression: findings confirmed by meta-analyses. Certain PTD biomarker studies have shown acute CSF sICAM, sVCAM, sFas were associated with PTD at 6-month. Acute CSF IL-7, IL-8 were associated with PTD at 12-month. Serum BDNF levels at 6-month and 12-month were associated with PTD at 6-month and 12-month.

Post-traumatic depression and soluble IL-6R signaling study was conducted. The study was designed as a prospective cohort study for individuals with moderate to severe TBI. About 155 adults were enrolled. Trajectory analysis was conducted to track monthly depressive symptoms over the first-year post-injury. PTD Status at 6 and 12 months post-injury was measured. Premorbid depression covariate was measured. Biomarker values for sgp130, IL-6, sIL-6R over first year post-injury were measured. Statistical approaches included descriptive statistics, and multivariate Regression and ROC. Linear regression to 12-month PHQ-9 total scores (FIG. 32) and mean IL-6 at 0-3 months stratified by sgp130 and PTD status at 12-month (FIG. 33) were measured. The data showed that depression is associated with higher IL-6 levels in the setting of low SGP130 levels, suggesting treating people with sgp130 below threshold of 130K pg/mL and increased IL-6 levels. In the context of PTD, there are complex IL-6 signaling cascades which may explain limited progress in the field at characterizing IL-6 pathophysiology implicated in depression. The relative and temporal relationships between IL-6 and its related soluble molecules sgp130 and sIL-6R should be considered. Similar results were obtained when people who had pre-morbid depression were excluded, and based on that exclusion, the model for sensitivity analysis were re-run.

IL-6 family proteins (including sIL-6R, sgp130, IL-6, and sgp130:sIL6R) are promising markers for predicting risk for multiple chronic conditions, including PTH, PTD, cognitive impairments, & epilepsy. Drug development as well as pharmacokinetic/pharmacodynamic studies for a humanized sgp130 protein for clinical consumption are performed. sgp130 can be used as a treatment intervention. It has been reported that a molar excess of sgp130 restricted the expression of the IL-6/sIL-6R complex. Silico modeling work including biomathematical approach for temporal dynamics and intervention simulation are performed. Sgp130 can mitigate the adverse effects of IL-6/sIL-6R by inhibiting trans-signaling. In Crohn's Disease, high plasma sgp130 can specifically block sIL-6R dependent IL-6 actions. Responses via the membrane bound IL-6R (classical signaling) remain unaffected. Both in vitro and in vivo inflammatory models show trans-signaling inhibition with administration of an fc dimerized version of sgp130 (sgp130fc). Sgp130fc caused suppression of colitis activity and apoptosis in patients with Crohn's Disease. STAT3 phosphorylation, a major signal transducer downstream of the initial IL-6/sIL-6R complex formation, decreased after administration of recombinant sgp130 in mice with hepatocellular carcinoma.

Example 6: Clinical Trials

To plan for clinical trials, the absolute risk reduction (ARR) and numbers needed to treat (NNT) constructs were adapted and applied to approximate potential treatment effects with sgp130. ARR equals to control event rate deducted by experimental event rate. The control group refers to endogenous "risk" profile while the experimental group refers to endogenous "non-risk or reduced risk" profile. NNT refers to the number of patients who need specific treatment to prevent one additional poor outcome. The ideal NNT is 1. NNT equals to the inverse of ARR. Here, the high risk TRAJ groups (with profiles of either low sgqp130:sIL-6R or high sIL-6R) was used as the no treatment and the low risk TRAJ groups (with profiles of either high sgqp130:sIL-6R or low sIL-6R) was used as the treatment group to approximate treatment effects (FIG. 44, Table 9). The absolute risk reduction referred to endogenous expression "no/reduced risk" profile (high sgp130:sIL-6R, low sIL-6R) vs. "risk" profile (low sgp130:sIL-6R, high sIL-6R). Treatment effects for NLR suggested that elevated NLR may persist into the post-acute and chronic phases of recovery.

TABLE 9

Associated unfavorable conditions, ARR and NNT for both low and high risk TRAJ groups.

| Endogenous Risk TRAJ Profile | Associated Unfavorable Conditions | Absolute Risk Reduction (ARR) | Numbers Needed to Treat (NNT) |
|---|---|---|---|
| Low sgp130:sIL-6R | High NLR | 20% | n = 5 |
| | Chronic Headaches | 33% | n = 3 |
| High sIL-6R | High NLR | 12% | n = 8 |
| | Overall Cognitive Impairment | 17% | n = 6 |
| | Chronic Headaches | 26% | n = 4 |

The temporal screening scheme leveraged knowledge of inflammatory trajectory courses for the early stratification of individuals and likely responders to the proposed treatments over their injury recovery courses (FIG. 45). The clinical trial pre-screen and monitoring of individuals on a high NLR course (ratio>10) is done during acute/post-acute case through three weeks post-TBI. The clinical trial also screens during the post-acute period for individuals on low spg130:sIL-6R trajectory with a ratio less than 6.5 and high sIL-6R (more than 22,000 pg/ml). The relationship between acute NLR and mean IL-6 family soluble molecules over the period of 1 to 6 months post-TBI was studied (FIG. 46A for sgp130 and FIG. 46B for IL-6R). High NLR group associated with maladaptive IL-6 soluble signaling manifested in the chronic phase (low sgp130 and high sIL-6R). Thus, NLR level can be leveraged as acute care proxy for IL-6 pathophysiology. The peripheral immune cell trajectories of the presently disclosed clinical population on to their endogenous chronic (m0-6) sIL-6R and sgp130:sIL-6R profiles is assessed High Neutrophil:Lymphocyte Ratio TRAJ had moderately strong concordance to the pathophysiological, exacerbated sIL-6R and sgp130:sIL-6R states. The best capture of this High sIL-6R and sgp130:sIL-6R state was High NLR, which is a novel pre-screening metric to guide early post-acute administration of sgp130 (FIG. 46C).

Biomarkers were also tested to gauge treatment effectiveness (FIGS. 47A-47L). A sgp130:sIL-6R ratio<6.5 was implicated in multiple chronic outcomes including headache, depression, and overall cognitive impairment. Individuals with low sgp130:sIL-6R profiles should be treated to achieve ratios >6.5 (comparable to high ratio TRAJ) (FIGS. 47A-47C). IL-6 levels in low TRAJ Group (FIG. 43C) were variable. There was no significant difference of IL-6 levels between low and high TRAJ Groups, demonstrating the buffering effect of sgp130 on IL-6 relationships to sIL-6R levels. (FIG. 43D).

sIL-6R levels alone have discriminatory capacity for poor outcome. It was suggested that sIL-6R levels in excess of 22.00 pg/mL are not well tolerated by endogenous spg130 buffering of trans-signaling; therefore, individuals with these levels higher than 22, 0000 pg/ml of sIL-6R, a characteristic of low ratio TRAJ, should be treated with excess spg130 to bind free sIL-6R.

Figure 47H:
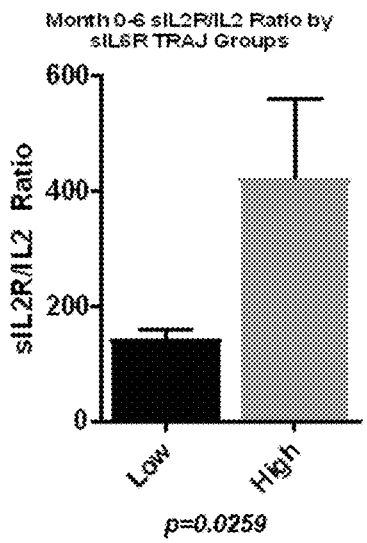
Figure 47I:
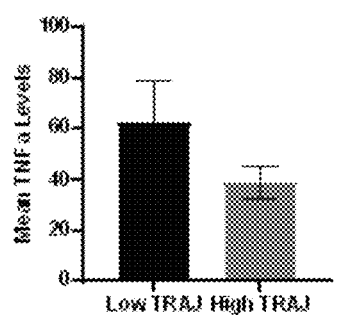
Figure 47J:
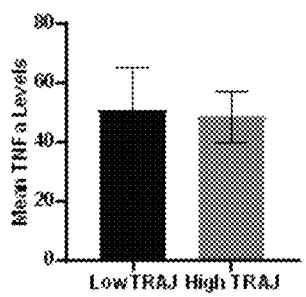
Figure 47K:
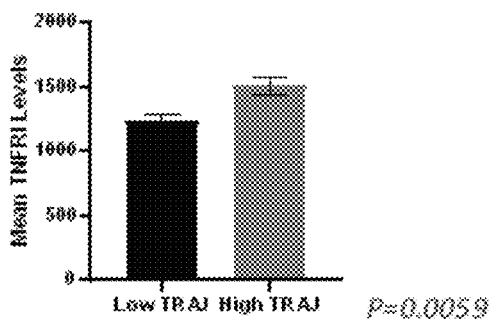
Figure 47L:
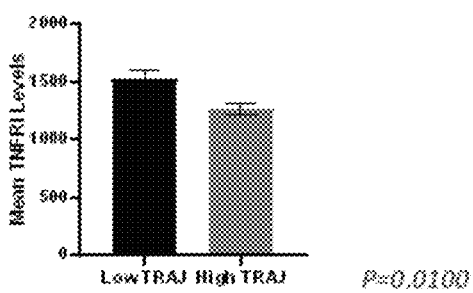

Il-2 and IL-2RA were also measured (FIGS. 47D-47G). Soluble receptor excess was driving the potential treatment relationships. Individuals in the high sIL6R TRAJ had significantly higher levels of sIL2R/IL2 Ratio, indicating this ratio as a potential readout for treatment effectiveness and as a potential contributor to IL-6 family related associations with TBI related impairments (FIG. 47H).

The NLR level in the post-acute phase may change with therapy and can be monitored, as well as neutrophil specific expression levels of IL-6 family molecules.

TNFα and TNFRI were also measured (FIGS. 47I-47L). Soluble TNFR1 load and binding was driving relationships and may be an additional marker of IL-6 family signaling on TBI related impairments.

sIL-6R is a potent effector of lymphocyte counts early after TBI as well as discriminator of multiple outcomes. sIL-6R, its ratio with SGP130, and SGP130 alone are associated with various secondary conditions, including cognitive, pain, mood and epilepsy and early white cell counts. spg130 can be an effective treatment across multiple outcomes based on NNT calculations, including for treatment effect readouts including IL-6 family related biomarkers as well as NLR.

sIL-6R was a potent effector of lymphocyte counts early after TBI as well as discriminator of multiple outcomes. sIL-6R, its ratio with SGP130, and SGP130 alone were associated with various secondary conditions, including cognitive, pain, mood and epilepsy and early white cell counts. SGP130 may be an effective treatment across multiple outcomes based on NNT calculations, including for treatment effect readouts including IL-6 family related biomarkers as well as NLR.

Example 7: Pre-Clinical Studies in Animal Models

The presently disclosed studies have also tested Fc-spg130 as treatment in mice and rat. CCI mice N=58 (severe) and sham with vehicle or sgp130 Rx 3 week study was performed. The regimens for sgp130 s.q. were 1 ug for the high dose and 0.25 ug for the low dose given on D1, D4, D7, D10 and D13. Mice had an average weight of 30 g. Novel object behavior, Morris water maze, and flow cytometry were performed. Blood was collected at sac, IL-6, sIL-6R, and sgp130 were measured. Brain was harvested, and ELISA on IL-6, sIL-6R, sgp130 was performed. N=48 rat CCI (severe) and sham with vehicle or sgp130 Rx 1 week study was performed. Motor testing, AST, and Y-maze were measured. Blood was collected and ELISA on IL-6, sIL-6R, sgp130 were measured. The brain was harvested, and ELISA on IL-6, sIL6R, sgp130 were measured. sIL6R complexes with ELISA is measured to evaluate mechanism.

CCI rats N=48 (severe) and sham with vehicle or sgp130 Rx 1 week study was performed. The regimens for sgp130 i.p. were 3 ug for the high dose (about 10 µg/kg) and 0.5 ug for the low dose (about 1.7 µg/kg) given on D1, D4 and D7. Rats had an average weight of 300 g. Motor testing beam balance, beam walk days 0-6 post injury, AST (acoustic startle response), Y-maze: (novel arm time/testing) and sucrose preference testing were performed. Blood was collected at sac, IL-6, sIL-6R, and sgp130 were measured. Brain was harvested, and ELISA on IL-6, sIL-6R, sgp130 was performed.

CCI in rats resulted in transient decrease in beam balance latencies (FIG. 48). Low dose and particularly high dose sgp130 administered at day 1 post-surgery reduced the severity of the beam balance deficit (FIG. 48). High dose sgp130 mice tend to return to baseline latency 3 days sooner than CCI VEH group overall (p=0.08) and significant reductions were noted D2 (Tukey's comparison: p<0.05) (FIG. 48). But from day 3 to day 6, the differences were not significant. CCI VEH versus Sham VEH had a p value of 0.0078 at day 1 and a p value of 0.0237 at day 2. CCI VEH versus CCI Low Dose had a p value of 0.1811 at day 1 and a p value of 0.5891 at day 2. CCI VEH versus CCI High Dose had a p value of 0.1905 at day 1 and a p value of 0.0402 at day 2. Sham VEH vs CCI Low Dose had a p value of 0.5329 at day 1 and a p value of 0.7239 at day 2. Sham VEH vs CCI High Dose had a p value of 0.2872 at day 1 and a p value of 0.8368 at day 2. CCI Low Dose vs CCI High Dose had a p value of 0.9948 at day 1 and a p value of 0.8403 at day 2.

CCI in rats resulted in transient increase in beam walking latencies (FIG. 49). High dose sgp130 administered at day 1 post-surgery reduced the severity of the beam walk deficit (FIG. 49). Shams did significantly better than CCI regardless of treatment overall. However, High dose sgp130 rats did not differ from sham by d5, while CCI vehicle did not differ from sham until the last day of testing (D6). These results may indicate modest treatment effect on motor performance. The differences at day 0 were not significant CCI VEH versus Sham VEH had different p values on different days (D1: $p<0.0001$; D2: $p<0.0001$; D3: $p<0.0001$; D4: $p=0.0013$; D5: $p=0.0387$; D6: $p=0.1997$). CCI VEH versus CCI Low Dose had different p values on different days (D1: $p=0.9944$; D2: $p=0.9567$; D3: $p=0.1011$; D4: $p=0.5942$; D5: $p=0.7296$; D6: $p=0.9997$). CCI VEH versus CCI High Dose had different p values on different days (D1: $p=0.9900$; D2: $p=0.6489$; D3: $p=0.2295$; D4: $p=0.4477$; D5: $p=0.2762$; D6: $p=0.3772$). Sham VEH versus CCI Low Dose had different p values on different days (D1: $p<0.0001$; D2: $p<0.0001$; D3: $p=0.0013$; D4: $p=0.0702$; D5: $p=0.1338$; D6: $p=0.2457$). Sham VEH versus CCI High Dose had different p values on different days (D1: $p<0.0001$; D2: $p<0.0001$; D3: $p=0.0004$; D4: $p=0.0153$; D5: $p=0.0748$; D6: $p=0.2842$). CCI Low Dose versus CCI High Dose had different p values on different days (D1: $p=0.9474$; D2: $p=0.9483$; D3: $p=0.9658$; D4: $p=0.9999$; D5: $p=0.8388$; D6: $p=0.4469$).

CCI in rats resulted in transient reduction in beam walking scores (FIG. 50). High dose CCI sgp130 group returned to baseline function 2 days sooner than CCI vehicle group (FIG. 50).

The sucrose preference test for rodents is based on a natural preference for sweets, with the assumption that preference is proportional to (hedonic) pleasure that the animal experiences with consumption. Typically, a two-bottle testing paradigm is used, where one drinking bottle contains sweetened solution and the other plain water. The amount of sweetened solution and plain water consumed across the testing period (duration of test typically 1-24 h) was measured. The time of day that the test was initiated is typically close to the beginning of the dark phase. The animals should be habituated to the testing conditions (e.g., test cage, time of test, having a choice of two bottles, potentially also to drinking the sweetened solution) prior to the test.

CCI in rats resulted in a reduced preference for the sucrose bottle (FIG. 51). Particularly, high dose SGP improved preference for sucrose bottle (FIG. 51). The differences on day 0 and day 6 were not significant. CCI VEH versus Sham VEH had different p values on different days (D1: $p<0.0001$; D2: $p<0.0001$; D3: $p=0.0009$; D4: $p=0.1247$; D5: Significant, but no p-value given). CCI VEH vs CCI Low Dose had different p values on different days (D1: $p=0.9544$; D2: $p=0.9967$; D3: $p=0.6956$; D4: $p=0.2064$; D5: Significant, but no p-value given). CCI VEH versus CCI High Dose had different p values on different days (D1: $p=0.9398$; D2: $p=0.3842$; D3: $p=0.8729$; D4: $p=0.1799$; D5: Significant, but no p-value given). Sham VEH versus CCI Low Dose had different p values on different days (D1: $p<0.0001$; D2: $p<0.0001$; D3: $p=0.0189$; D4: $p=0.2064$; D5: n/a). Sham VEH versus CCI High Dose had different p values on different days (D1: $p<0.0001$; D2: $p=0.0.0015$; D3: $p=0.0163$; D4: $p=0.1799$; D5: n/a). CCI Low Dose versus CCI High Dose had different p values on different days (D1: $p=0.9999$; D2: $p=0.5407$; D3: $p=0.9912$; D4: $p=0.7076$; D5: n/a).

For CCI mouse model, acquisition latency group comparison (FIG. 52) was performed. CCI Low Dose and CCI High Dose each was with significantly lower latencies than CCI vehicle ($p<0.03$ both comparisons; two factor RMANOVA). CCI VEH vs CCI Low Dose had significantly lower latency D18 ($p<0.05$, single factor ANOVA). CCI VEH versus Sham VEH had different p values on different days (D14: $p=0.0041$; D15: $p=0.0018$; D16: $p=0.0330$; D17: $p=0.1017$; D18: $p=0.0104$). CCI VEH versus CCI Low Dose had different p values on different days (D14: $p=0.9509$; D15: $p=0.2884$; D16: $p=0.5953$; D17: $p=0.5548$; D18: $p=0.0248$). CCI VEH versus CCI High Dose had different p values on different days (D14: $p=0.7692$; D15: $p=0.2304$; D16: $p=0.9254$; D17: $p=0.9203$; D18: $p=0.1275$). Acquisition PZTA group comparison (FIG. 53) was also performed. Decreased PZTA in sgp130 treated mice (CCI Low Dose vs CCI VEH) was in connection to lowered anxiety behavior ($p=0.0005$). The low dose group performed significantly better than the CCI vehicle group on day 17 ($p=0.032$). And the differences at day 18 were not significant. CCI VEH versus Sham VEH had different p values on different days (D14: $p=0.0403$; D15: $p=0.0009$; D16: $p=0.1233$; D17: $p=0.0302$). CCI VEH versus CCI Low Dose had different p values on different days (D14: $p=0.7031$; D15: $p=0.2310$; D16: $p=0.1136$; D17: $p=0.2061$). CCI VEH versus CCI High Dose had different p values on different days (D14: $p=0.5260$; D15: $p=0.9642$; D16: $p=0.9951$; D17: $p=0.6133$).

Lymphocytes group comparison was also performed. sgp130 can support lymphocyte counts and help prevent lymphopenia at 21 days post injury (FIG. 54). B-cell fraction was impacted by TBI and rescued by sgp130 treatment, specifically high dose sgp130 on D21 (FIG. 55). sgp130 (any dose) had rescue effect on IL-12, IL-10, GM-CSF, MIP-1b (FIG. 56). Low dose spg130 rescued effect on IL-17; high dose sgp130 reduced TNF-α and IL-6 (FIG. 56). This is important in considering combination therapies that might increase these traditionally pro-inflammatory markers (e.g. IL-7).

Sgp130 had a possible slight rescue effect on IL-12 as dosage increased in rats (FIG. 57). Any dose of sgp130 reduced TNFα and IL-1b levels. sgp130 treatment reduced IL-2 levels. Reduced IL-2 may reduce inflammatory elements such as NK production in response to injury and lead to increased Treg production. MCP-1 is a protein in the chemokine family. Decreasing levels with sgp130 treatment may be a result of reductions in inflammation as a whole brought about by the treatment.

Biomarker levels can be dependent on brain region and hemisphere. In rat right hippocampus tissues, sgp130 had a rescue effect on IFNγ, IL-10, MIP-1a, IL-2, Fractalkine and RANTES, and low doses of sgp130 reduced IL-6 levels and TNF-α (FIG. 71A). In rat left hippocampus tissues, sgp130 had a variable rescue effect on IFNγ, Il-10, MIP-1a, IL-2, Fractalkine and RANTES (FIG. 71B). Right and left hippocampal tissues had similar patterns of IFNγ, IL-10 and MIP-1a levels. In rat right striatum tissues, sgp130 had a rescue effect on MIP-2 and MIP-1a, and both dose of sgp130 reduced IL-6 levels, TNF-α and IL-1β (FIG. 72A). In rat left striatum tissues, sgp130 had a rescue effect on Fractalkine, IL-2 and VEGF, and both dose of sgp130 reduced IL-1b levels (FIG. 72B). Right and left striatum tissues had similar IL-1b patterns. CCI was administered to the right side of the rat brain.

Sgp130 has a broad restorative effect on many different endpoints, including motor, anhedonia (rodent behavior similar to depression), cognitive performance. In addition, there is a restorative effect of sgp130 on lymphocytes which may be relevant to the sIL6R associations with other soluble receptors known to impact lymphocytes (e.g. sTNFR). sgp130 treatment has a significant impact on inflammation, including reduction of IL-6 levels and TNF levels.

Example 8: Longitudinal Characterization of Headache after TBI and Potential Immunological Target Certain studies have focused on calculating incidence and identifying distinct types of headaches after a TBI with follow-up at 3, 6, and 12 months (Stacey et al., Journal of Neurotrauma. 2016; 34(8):1558-1564; Hoffman et al., J Neurotrauma. 2011; 28(9):1719-1725; Lucas et al., Cephalalgia. 2014; 34(2):93-102). The most commonly identified headache type is migraine, followed by tension-type headaches (Stacey et al., Journal of Neurotrauma. 2016; 34(8): 1558-1564; Lucas et al., Cephalalgia. 2014; 34(2):93-102; Finkel et al., Headache: The Journal of Head and Face Pain. 2017; 57(5):719-728). Impact on daily life has also been assessed at 3, 6, and 12 months, and disability is concomitant with headaches at these time points (Stacey et al., Journal of Neurotrauma. 2016; 34(8):1558-1564). Characteristics of pain and other symptoms associated with headaches, such as vision changes, pain type, location, duration, or severity have not yet been assessed longitudinally in a TBI population.

The pathophysiological mechanisms of headaches after TBI are poorly understood, but inflammation represents a common pathway implicated in both headaches and TBI, presenting the potential for targeted treatment. An inflammatory response is rapidly elicited in response to a brain injury that can have both beneficial and deleterious effects. The brain mounts a local innate immune response and peripheral leukocytes are recruited acutely to injury sites resulting in cellular and tissue damage and the release of endogenous factors that activate pathways that ultimately result in the release of inflammatory markers, including the pro-inflammatory cytokine interleukin (IL)-6 (Corrigan et al., Journal of Neuroinflammation. 2016; 13:264; Kumar et al., Brain, Behavior, and Immunity. 2015; 45:253-262). Acute IL-6 upregulation is associated with tissue regeneration and prevention of neuron apoptosis (Penkowa et al., Glia. 2000; 32(3):271-285). Sustained upregulation of IL-6 contributes to adverse outcomes in animal model of brain inflammation (Eugster et al., European Journal of Immunology. 1998; 28(7):2178-2187) and elevated levels are well-documented after TBI in humans (Bell et al., Journal of Neurotrauma. 1997; 14(7):451-457; Kossmann et al., Brain Research. 1996; 713(1-2):143-152). IL-6 is an important component of the acute innate response after injury, and high levels of IL-6 for the first week post-injury are associated with unfavorable outcomes (Kumar et al., Brain, Behavior, and Immunity. 2015; 45:253-262).

The role of IL-6 in the sub-acute and chronic phase after TBI is less understood. In one prospective cohort study, serum cytokine load, including IL-6, was found to be elevated over 3 months after a TBI and elevated cytokine load was associated with unfavorable global outcomes at 6 and 12 months (Kumar et al., The Journal of head trauma rehabilitation. 2015; 30(6):369-381). IL-6 is involved in classical signaling and trans-signaling, the latter of which is responsible for harmful downstream effects. In trans-signaling, IL-6 binds to its soluble receptor (sIL-6R), which is readily detected at sites of inflammation. The activity of this complex is blocked by the soluble form of glycoprotein130 (sgp130)(Jones et al., J Clin Invest. 2011; 121(9):3375-3383). In patients with cluster headaches, serum levels of IL-2 receptors were found to be elevated relative to controls with no cluster headaches; however, IL-6, sIL-6R, and sgp130 levels did not differ between headache groups (Empl et al., Headache: The Journal of Head and Face Pain. 2003; 43(1):63-68). Following trauma, sIL-6R is released from neutrophils, but sgp130 antagonizes the IL-6 trans-signaling. Certain studies have failed to examine the relationships between these two IL-6 family soluble receptors and headaches in TBI patients, and none of the acute changes that occur post-injury have been adequately associated with headache in a way that can inform therapeutic decision-making.

Headaches after TBI represent one of the most prevalent impairments impacting quality of life for patients with TBI (Stacey et al., Journal of Neurotrauma. 2016; 34(8):1558-1564; Hoffman et al., J Neurotrauma. 2011; 28(9):1719-1725). Though anti-inflammatory treatments have been beneficial in certain acute migraine treatment (Headache. 2018 June; 58(6):811-826) and in alleviating pain and moderating headache severity in the general population (Codispoti et al., Headache. 2001 July-August; 41(7):665-79; Lipton et al., Arch Intern Med. 2000; 160(22):3486-3492), these treatments may not be effective for headaches or migraines after TBI (Leung et al., Pain Physician. 2016 February; 19(2): E347-54; Minen et al., Curr Neurol Neurosci Rep. 2016; 16(11):100; Theeler et al., Headache. 2013; 53(6):881-900). Nevertheless, non-steroidal anti-inflammatory drugs are prescribed as a treatment for headaches after TBI, suggesting the need for more clinical studies to evaluate specific inflammatory mechanisms implicated with headaches after TBI (Kamins et al., Headache. 2018 June; 58(6):811-826). Certain studies have also gathered limited data on longitudinal patterns of headaches and relationships with other common TBI impairments. To this end, the present disclosure characterized headache phenotypes over time and to describe associations of these phenotypes with other co-occurring post-TBI conditions. As inflammation is implicated both in headaches and in TBI, the present disclosure tested the hypothesis that relative levels of the inflammatory biomarkers sgp130 and sIL-6R underlie the pathophysiology of chronic headache over time after TBI.

Material and Methods

Participants were recruited as a part of a prospective cohort study. Informed consent was obtained. Participants were approached for enrollment in an acute care hospital, rehab hospital, or outpatient clinic. Patients were included if they had a non-penetrating closed head injury verified with TBI-related ICD-9 diagnosis code and/or sufficient medical documentation of medical or functional complications on day of injury, including positive anatomic neuroimaging findings or focal neurologic signs. Patients were excluded if they (i) were older than 79 years; (ii) had a penetrating head injury; (iii) had an untreated endocrine disorder; (iv) had an autoimmune disorder; (v) had a history of significant neurological or neurodegenerative disease; (vi) had documented history of previous TBI or stroke; or (vii) were a prisoner. Demographic, serum samples, headache and other outcome data were collected monthly across the first year. There were n=79 individuals with data from a headache questionnaire at two or more of the monthly time points. N=2 of those individuals refused blood for various reasons. As a reference group for inflammatory marker concentrations, 18 healthy adult controls with no prior history of TBI provided a single serum sample.

Demographic and clinical variables collected from medical chart review included: age, BMI, sex, Glasgow Coma Score (GCS), race, mechanism of injury, pre-injury history of anxiety, pre-injury history of depression, pre-injury history of alcoholism, pre-injury history of headache, smoking status, and illicit drug use status. Smoking and illicit drug use statuses were dichotomized into two groups: never users and ever users.

Serum samples (n=77 subjects, n=240 samples) were collected monthly by trained research coordinators. Samples were centrifuged, aliquoted, and stored at −80° C. until pulled for batch analysis.

Inflammatory markers were measured using a Luminex™ bead array assay (Millipore, Billerica, Massachusetts). The markers included in this study (IL-6, sgp130, and sIL-6R) were part of larger assays containing several markers. Signal detection uses a microsphere tagged with fluorescent-labelled markers to analyze protein binding. The minimum detectable concentrations for IL-6, sgp130, and sIL-6R were 0.11 pg/mL, 6 pg/mL and 9 pg/mL, respectively. The observed inter- and intra-assay coefficients of variation (CV) for the assay containing IL-6 were <5% and <20%, respectively. For the assay containing sgp130 and sIL-6R, the inter- and intra-assay CV were <10% and <15%, respectively. Due to missing data at some monthly time points, serum sgp130 and sIL-6R averages were calculated over three month increments, and the ratio of these mean values was used for analysis.

Serum cortisol levels were measured using a commercial ELISA kit (Salivary Cortisol ELISA Kit. Salimetrics. https://www.salimetrics.com/assay-kit/salivary-cortisol-elisa-kit) according to manufacturers' instruction. Samples were run for each of the monthly time points using the ELISA technique. To avoid matrix effects with this assay, serum samples were diluted 1:36. Although the it was developed and validated for saliva, an experiment using serum cortisol showed an excellent profile of linearity with serial dilution, and recovery (90-110%) for standards with a range of dilution 1:20 to 1:40. Among the 96 wells in each plate, 10 wells were used in duplicate to evaluate intra-plate reliability, and an additional 6 wells were used to evaluate inter-plate reliability. Otherwise, all samples were evaluated in singlet to conserve sample volume. Throughout all plates, the observed intra- and inter-plate CV were <5% and <6%, respectively.

The primary outcome of interest was headache status over the first year post-injury. A monthly headache questionnaire was administered, and headache status (yes/no) was identified. Information on vision changes and face or arm skin sensations with onset of headache were also obtained as a part of the headache questionnaire. Headache location, pain types, duration, severity, and frequency measures were other measures included in the questionnaire.

Certain studies have used serum cortisol levels as an indicator of stress after trauma (Ranganathan et al., Brain Injury. 2016; 30(4):452-461). Trauma-induced physical stress can incite increased cortisol levels in plasma, which can be attributed to increased cortisol secretion rates (King et al., Ann Surg. 1970; 172(6):975-984). Thus, serum cortisol levels were determined monthly as an indicator of stress. Quarterly averages of these levels were used for analysis.

At 6 and 12 month visits, questions were asked regarding a person's return to normal functioning using a Percent Back to Normal Questionnaire (Patrick et al., J Gen Intern Med. 1988; 3(3):218-223). Participants were asked to rate their functioning relative to prior their injuries. Patients self-reported a percentage back to normal (i) overall; (ii) in physical function; (iii) in cognitive function; and (iv) emotionally, where "normal" was defined as function pre-injury.

The Generalized Anxiety Disorder (GAD-7) questionnaire (Spitzer et al., Arch Intern Med. 2006; 166(10):1092-1097) was used to assess anxiety at each monthly visit. GAD-7 evaluates seven statements regarding anxiety with the following responses and corresponding scores: "not at all" (0), "several days" (1), "more than half the days" (2), and "nearly every day" (3). These responses were summed, and quarterly averages of the scores were used for analysis.

Post-traumatic depression (PTD) was assessed using the Patient Health Questionnaire (PHQ-9) (Kroenke et al., Psychiatric Annals. 2002; 32(9):509-515). PHQ-9 scores the nine DSM-IV criteria from "not at all" (0) to "nearly every day" (3). PHQ-9 scores were collected monthly, and a PTD status was assigned based on the endorsement of ≥5 symptoms, with at least one being one of the cardinal depression symptoms, depressed mood or anhedonia. This definition of PTD has shown strong validity in TBI populations (Fann et al., J Head Trauma Rehabil. 2005; 20(6):501-511). A quarterly PTD variable was created for analysis. If a person had PTD in any of the corresponding 3 months, the PTD for that quarter was "yes". If a person did not have PTD in each of the corresponding 3 months, the PTD for that quarter was "no".

Fatigue was assessed using two questionnaires: PROMIS-Fatigue (PROMIS) (Cella et al., Med Care. 2007; 45(5 Suppl 1):S3-S11) and Fatigue Severity Scale (FSS) (Krupp et al., Arch Neurol. 1989; 46(10):1121-1123). The PROMIS questionnaire evaluates eight fatigue variables on a 1-5 frequency Likert scale, ranging from "never" to "always" or "not at all" to "very much", depending on the question. The FSS questionnaire consists of nine statements regarding fatigue, and the patient self-reports agreement with each on a 1-7 Likert scale, which are summed for a total score. Lower numbers indicate disagreement with a statement, and higher numbers indicates agreement with the statement. Both questionnaires were administered monthly, and quarterly averages of each were used for analysis.

Statistical analyses were performed using SAS™ Version 9.4. Group-based trajectory analysis (TRAJ) was used to identify subgroups of the population with different temporal patterns of headache status across the first year. TRAJ groups were generated using the PROC TRAJ SAS Macro and fit using a Bernoulli distribution. TRAJ was used to identify meaningful clinical subgroups, mapping the developmental course of headaches status in this TBI population. The model with the lowest Bayesian Information Criterion was used to ascertain the number of groups and each group's polynomial order. The fit of the model was confirmed by evaluating at the posterior probability for each group.

Due to missing data at some monthly time points, serum sgp130 and sIL-6R averages were calculated over three-month increments and the ratio of these mean values was used for analysis. The quarterly ratios of sgp130 and sIL-6R (sgp130:sIL-6R) were tested for bivariate associations with covariates. Means were computed to describe continuous demographic and clinical covariates, and Pearson correlations with the ratio were determined. Headache TRAJ groups were also tested for bivariate associations with sgp130:sIL-6R and covariates. Means were computed to describe continuous variables and nonparametric Mann Whitney U tests were conducted. For categorical variables, frequency measures were used, and Chi-Square tests or Fisher's Exact tests were conducted appropriately. The quarterly mean differences in sgp130:sIL-6R between TRAJ groups were tested using the Kruskal-Wallis Test.

Multivariable logistic regression was used to assess relationships between sgp130:sIL-6R and TRAJ groups, while controlling for relevant covariates. To control for confounding, age was included in the model. Certain studies have demonstrated associations between sex differences in immune responses after TBI (Caplan et al., Journal of Neuroscience Research. 95(1-2):509-517), between GCS and inflammation profiles (Schneider et al., Neuroimmunomodulation. 2012; 19(6):377-385), and between pre-injury substance abuse and post-injury outcomes (Halker et al., Neurology. 2011; 76 (Issue 7, Supplement 2):S37-S43). There are also established relationships between the development of headaches after TBI and both sex and pre-injury history of headaches (Hoffman et al., J Neurotrauma. 2011; 28(9):1719-1725). Thus, an a priori decision was made to control for several other covariates in the model including sex, GCS, pre-injury history of alcoholism, and pre-injury history of headaches.

To determine if headache TRAJ group was associated with secondary outcome variables, nonparametric Mann Whitney U tests were conducted for continuous variables and Chi-Square tests were conducted for categorical variables. The significance level was set at $\alpha=0.05$.

Results

Characterization of the Cohort

FIG. 58 outlines demographic and clinical variables for the TBI cohort. The mean age of the cohort was 40.18, compared to a mean age of 29.85 in the non-injured control group. This cohort is predominantly male (72.2%), compared to a 43.75% male non-injured control group. Both the cohort and the non-injured control group were predominantly white individuals (95.5% and 71.88%, respectively). The most common mechanism of injury was a motor vehicle accident, followed by falls. FIG. 58 also outlines associations of the demographic and clinical variables with sgp130: sIL-6R. The only statistically significant association was a strong, negative correlation between illicit drug use status and sgp130:sIL-6R (mean difference=−0.825; p=0.027).

Trajectory Groups

In the presently disclosed cohort, three trajectory group profiles (low, resolve, and chronic) were identified for headache status over time for the first year post-injury. Monthly headache status (percentage of those who endorsed headache) for each TRAJ group are graphed in FIG. 59. The average group posterior probability was 0.845 for the low TRAJ group, 0.890 for the resolve TRAJ group, and 0.891 for the chronic TRAJ group.

The maximum prevalence of headache endorsement among individuals in the low TRAJ group (n=21) was 9.09% (n=1) in month 1. No individuals in the low TRAJ group endorsed headaches at any other month, except 8.33% (n=2) in month 11. The resolve TRAJ group (n=23) consists of individuals who endorse having headaches in the first several months, but the percentage of those who endorse headaches in the resolve TRAJ groups declines linearly after month 2. The chronic TRAJ group (n=35) follows a cubic trajectory consisting of individuals who have headaches that persist through 12 months post-injury. The percentage of those who endorsed headaches was always above 55% in the chronic TRAJ group.

The Effect of TBI on Sgp130:sIL-6R

Individuals with a TBI can have lower sgp130:sIL-6R levels than non-injury controls. Thus, a one-sided p-value was used. The effect of TBI on sgp130:sIL-6R is graphed in FIG. 60. Individuals with a TBI (n=77) have lower levels of sgp30:sIL-6R in all four quarters post-injury compared to controls with no injury (n=18). Ibis difference is statistically significant in quarters 1, 3, and 4 (p=0.039, 0.032, and 0.031, respectively).

Determining the Sgp130:sIL-6R Cut Point

To use sgp130:sIL-6R as a diagnostic predictor of symptomatic TRAJ group membership (resolve and chronic), the ratio was dichotomized into high and low sgp130:sIL6R ratios. A cut-point of 5.9 was determined by examining the distribution of sgp130:sIL-6R by symptomatic TRAJ groups as seen in FIG. 61. Quarter 1 sgp130:sIL-6R was used because the trajectory between the resolve and chronic TRAJ groups diverges after month 3. The distribution of the low TRAJ group was not considered for determining the cut-point since nearly all these individuals do not exhibit headache throughout the time course. The sensitivity and specificity to predict headache TRAJ group (resolve vs chronic) were 74.1% and 61.9%, respectively.

FIG. 62 outlines demographic and clinical variables by TRAJ group. The mean age of the low TRAJ group was higher than the resolve and chronic TRAJ groups (p=0.047). Individuals in the chronic TRAJ group had a greater pre-injury history of alcoholism (p=0.099), but this difference was not statistically significant.

Biomarker Relationships to Headache TRAJ Group

The average levels of IL-6 did not differ by TRAJ group in any quarter (data not shown, p≥0.214 for all quarters). The sgp130:sIL-6R quarterly averages stratified by TRAJ group are graphed in FIG. 63. Individuals in the chronic TRAJ group had significantly lower sgp130:sIL-6R ratios than among individuals in the low and resolve TRAJ groups in quarters 1 and 2 (p=0.005 and 0.013, respectively). The sgp130:sIL-6R quarterly averages of the TRAJ groups with headache symptoms in quarter 1 (the resolve and chronic TRAJ groups) are graphed in FIG. 64. Individuals in the resolve TRAJ group had similar sgp130:sIL-6R ratios to non-injury controls at all quarterly time points (p>0.05 all comparisons). In contrast, individuals in the chronic TRAJ group had significantly lower sgp130:sIL-6R ratios at all quarterly time points (p<0.05 all comparisons).

In order to compare the TRAJ groups that are symptomatic in the first quarter, a binary logistic regression model was run with the resolve and chronic TRAJ groups only (FIG. 65). The probability of chronic TRAJ group was modelled relative to resolve TRAJ. Quarter 1 sgp130:sIL-6R was assessed as a continuous independent variable in the initial logistic regression model for headache TRAJ group. In the unadjusted model, a one standard deviation increase in quarter 1 sgp130:sIL-6R protects against chronic headache TRAJ membership compared to resolve by 73.8% [OR=0.262; 95% CI: 0.104-0.660; p=0.005]. After controlling for age, sex, GCS, pre-injury history of alcoholism, and pre-injury history of headaches, a one standard deviation increase in quarter 1 sgp130:sIL-6R protects against chronic headache TRAJ membership compared to resolve by 75.9% [OR=0.241; 95% CI: 0.087-0.669; p=0.006].

Characterization of Headache

Between individuals in the resolve and chronic TRAJ groups, there were no differences in vision changes (19% and 28%, respectively, p=0.526), nor in skin sensations (27% and 34%, respectively, p=0.579) prior to the onset of a headache. The most frequently reported headache locations among individuals in the resolve TRAJ group were the front, and the left and right temples, reported an average of 7.96%, 6.82%, and 6.82% of the months, respectively. The most frequently reported headache locations among individuals in the chronic TRAJ group were the back, front, and the right temple, reported an average of 19.79%, 19.08%, and 14.90% of the months, respectively. The most frequently reported pain types associated with headaches among individuals in the resolve TRAJ group were pressure (16.29%), constant (12.88%), throbbing (11.37%), and tightness (10.32% of the months). The most frequently reported pain types associated with headaches among individuals in the chronic trajectory group were pressure (34.76%), constant (28.03%), pounding (24.51%), and throbbing (23.53% of the months).

The number of days with a headache reported by individuals each month were averaged by quarter and these averages are graphed in FIG. 66A, stratified by TRAJ group. The mean number of headache days per month reported by individuals in the chronic TRAJ group was 22 days in quarter 1, 14.4 days in quarter 2, 21.8 days in quarter 3, and 16.4 days in quarter 4.

The severity of headaches was reported by individuals to be mild (1), moderate (2), or severe (3). These monthly severity reports were averaged by quarter and these averages are graphed in FIG. 66B, stratified by TRAJ group. There were no significant differences in reported severity between individuals in the resolve and chronic TRAJ groups, but the mean severity for those in the chronic TRAJ group always trended higher than the mean severity for individuals in the resolve TRAJ group.

Associations Between Headache Trajectory Group and Secondary Outcomes

Mean percent back to normal was reported at 6 and 12-month visits, and the results are shown in FIG. 67. The average total percent back to normal was not significantly different between the three headache TRAJ groups at either 6 months (p=0.063) or at 12 months (p=0.113), but individuals in the resolve TRAJ group trended lower than individuals in the low TRAJ group at both 6 months (76.2% vs. 88.6%) and at 12 months (84.6% vs. 88.2%). Those in the chronic TRAJ group trended lower than individuals in both the low and resolve TRAJ groups at both 6 months (72.3%) and 12 months (78.1%). The average reported physical percent back to normal at 6 months were significantly lower for individuals in the resolve and chronic TRAJ groups (65.9% vs. 72.6%) than those in the low TRAJ group (87.7%; p=0.023). By 12 months, individuals in the resolve TRAJ group reported on average a physical percent back to normal that was similar to the physical percent back to normal reported by those in the low TRAJ group (87.5% vs. 89.4%). The percentage reported by those in the resolve TRAJ group remained significantly lower (74.7%, p=0.016). A similar temporal pattern was also seen in the average reported emotional percent back to normal. At 6 months, emotional percent back to normal showed no trends in differences among groups. At 12 months, individuals in the low TRAJ group reported 89.9% back to normal emotionally, individuals in the resolve TRAJ group reported 92.3%, and those in the chronic TRAJ group reported 82.3% (p=0.075). Similar trends were also seen in the average cognitive percent back to normal, but the differences were not significant at either 6 months (low: 83.8%; resolve: 82.5%; chronic; 71.0%, p=0.093) or 12 months (low: 90.1%; resolve: 87.9%; chronic; 80.6%, p=0.127).

Mean GAD-7 scores are provided in FIG. 68, row a, stratified by headache TRAJ group. Scores for individuals in the resolve TRAJ group decreased over time, and the difference between groups was significant in quarter 3 (low: 1.90; resolve: 3.36; chronic: 4.61, p=0.021). This trend continued into quarter 4, in which individuals in the low and resolve TRAJ groups scored significantly lower than those in the chronic group (low: 1.60; resolve: 2.96; chronic: 3.72, p=0.031).

The number and percentage of individuals with PTD each quarter are provided in FIG. 68, row b, stratified by headache TRAJ group. There was a significant difference between TRAJ groups in quarter 4, in which there were significantly more individuals with PTD in the chronic TRAJ group (n=11, 37.9%) compared to the low (n=1, 5.9%) and resolve groups (n=4, 19.1%; p=0.040). Notably, the percentage of individuals with PTD in low and resolve TRAJ groups roughly decreased over the four quarters, whereas the percentage of individuals with PTD in the chronic TRAJ group roughly increased from quarter 1 (n=7, 29.2%) to 2 (n=12, 44.4%), and then remained high in quarters 3 (n=11, 39.3%) and 4 (n=11, 37.9%).

PROMIS scores were averaged quarterly and the mean scores are provided in FIG. 68, row c, stratified by headache TRAJ group. There was a significant difference in PROMIS scores between TRAJ groups in quarter 1 scores (p=0.002). Individuals in the low TRAJ group had the lowest mean PROMIS score compared to individuals in the resolve and chronic TRAJ groups in the first quarter (11.89 vs. 18.65 and 16.05), the second quarter (12.52 vs. 14.53 and 16.26; p=0.066), the third quarter (12.47 vs. 14.53 and 15.87; p=0.071) and the fourth quarter (11.41 vs. 12.94 and 14.83; p=0.068).

Mean FSS scores are provided in FIG. 68, row d, stratified by headache TRAJ group. There was a significant difference in FSS scores between TRAJ groups in quarter 1 scores (p=0.004); individuals in the low TRAJ group had the lowest mean FSS score compared to individuals in the resolve and chronic TRAJ groups (16.43 vs. 27.73 and 24.67). A similar pattern between groups existed the fourth quarter (14.94 vs. 19.27 and 22.44; p=0.070).

There was a statistically significant difference between TRAJ groups in Quarter 3 (p=0.049), in which individuals in the chronic TRAJ group had higher average levels of cortisol (167.2 ng/mL) than did those in the low and resolve TRAJ groups (142.2 and 143.3 ng/mL). This pattern was also seen in quarter 2 (152.8 vs. 140.8 and 131.6 ng/mL); p=0.127), but the difference between groups was not statistically significant.

DISCUSSION

Headache after TBI is an important public health issue, as it is one of the most common impairment after TBI and is the most common secondary headache disorder. Yet few studies have identified temporal profiles of headaches and biological correlates. Certain studies have examined post-traumatic headache longitudinally, but only in 3 month intervals or more (Stacey et al., Journal of Neurotrauma. 2016; 34(8): 1558-1564; Hoffman et al., J Neurotrauma. 2011; 28(9): 1719-1725 Lucas et al., Cephalalgia. 2014; 34(2):93-102). The present disclosure used group-based trajectory analysis with monthly time points to uncover three clinically relevant and meaningful headache profiles. The present disclosure identified an inflammatory marker, sgp130:sIL-6R, that is highly relevant prognostic marker for chronic headache trajectory after TBI.

Chronic daily headache (CDH) is defined as a 3-month history of headaches occurring for at least 15 days per month (Halker et al., Neurology. 2011; 76 (Issue 7, Supplement 2):S37-S43). The present disclosure observed that the number of days with headache in a month experienced by individuals in the chronic TRAJ group almost always averages above this 15 days per month mark. Treating CDH in general populations can be incredibly complex and difficult (Halker et al., Neurology. 2011; 76 (Issue 7, Supplement 2):S37-S43; Levin J H et al., R I Med J (2013). 2014 Feb. 3; 98(2):22-5). Current practice recommends lifestyle changes such as moderating caffeine intake, increasing physical activity, improving sleep hygiene and diet (Levin J H et al., R I Med J (2013). 2014 Feb. 3; 98(2):22-5). Furthermore, no randomized clinical trials have been conducted to date on treatments for headaches after TBI.

The International Classification of Headache Disorders-3 (ICHD-3) acknowledges that there are no specific features known to distinguish the types of headaches attributed to trauma or injury to the head or neck, and does not distinguish between type, such as migraine or tension-type headaches, despite differences in triggers, symptoms, and treatments (Headache Classification Committee of the International Headache Society (IHS), Cephalalgia 2018, Vol. 38(1) 64-73). Currently, the ICHD-3 diagnoses acute post-traumatic headache if the headaches occur within the first three months and persistent post-traumatic headache if they continue to occur. In the presently disclosed study, the resolve and chronic TRAJ groups experience differences in types of headaches, besides the acute versus persistent distinctions.

For example, those in the resolve TRAJ group experienced headaches most commonly in the right and left temples, whereas those in the chronic TRAJ group experienced them most commonly in the back and front of the head. Further, those in the resolve TRAJ group frequently reported tightness while those in the chronic TRAJ group did not. Those in the chronic TRAJ group frequently reported pounding sensations, whereas those in the resolve TRAJ group did not. Although differences in the reported severity of headaches does not differ between groups, the reported severity in the chronic TRAJ groups trends above resolve TRAJ throughout the first year. In general, the headaches of those in the chronic TRAJ group not only persist longer, but are also more frequent, more migraine-like, and may also be more severe with respect to pain. These nuanced differences between individuals with chronic versus resolving headaches may be important to include in ICHD classification systems.

A component of the present disclosure was the investigation into biological correlates of headache trajectory. Certain studies have suggested that IL-6 itself can serve as a biomarker of inflammatory burden after a TBI, and intrinsic brain mechanisms such as inflammation due to innate and adaptive immune responses impact outcomes after TBI (Kumar et al., Brain, Behavior, and Immunity. 2015; 45:253-262). No human studies have considered the ratio between sIL-6R and sgp130 and its clinical implications for headaches, despite a need to better understand post-traumatic headaches (Kamins et al., Headache. 2018 June; 58(6):811-826). The present disclosure assesses these relationships longitudinally after injury in a moderate to severe TBI population and evaluates the associations of the sgp130:sIL-6R ratio with outcomes.

In classical IL-6 signaling, IL-6 binds to its alpha receptor (IL-6R), which is not involved in signal transduction and is not expressed on all cells in the body. When the IL-6/IL-6R complex associates with the widely-expressed G-protein130, signal transduction is possible. Downstream effects of classic IL-6 signaling are primarily beneficial. However, IL-6 can also bind a soluble form of the IL-6 receptor (sIL-6R) and initiate a process known as trans-signaling in which the IL-6/sIL-6R complex activates the ubiquitously expressed membrane-bound gp130 (Scheller et al., Signal Transduction. 2006; 6(4):240-259). Trans-signaling is responsible for the detrimental effects of IL-6, as it increases the half-life and bioavailability of IL-6 and can lead to chronic inflammation (Hunter et al., Nature Immunology. 2015; 16(5):448-457). In serum, the IL-6/sIL-6R complex is limited by the presence of the soluble form of G-protein130 (sgp130), which blocks IL-6/sIL-6R trans-signaling. Sgp130 has no effect on signal transmission via the classical IL-6 signaling processes (Scheller et al., Signal Transduction. 2006; 6(4):240-259). Therefore, in post-TBI inflammation, sgp130 may be a therapeutic target for the prevention of adverse effects of trans-signaling by blocking chronic IL-6 effects that are mediated via sIL-6R.

Individuals with TBI in the present disclosure had significantly lower levels of sgp130:sIL-6R but similar levels of IL-6 across groups. Importantly, the quarter 1 sgp130:sIL-6R levels of those in the chronic TRAJ group were lower than the quarter 1 sgp130:sIL-6R of those in the low TRAJ group, and significantly lower still than the quarter 1 sgp130:sIL-6R levels of those in the resolve TRAJ group. Those in the resolve TRAJ group have quarter 1 sgp130:sIL-6R similar to levels in the non-injury controls. Thus, it is possible that an increase in sgp130 relative to sIL-6R in this resolve TRAJ group of individuals with a TBI acts to prevent the deleterious effects of trans-signaling, which is associated with poor global outcomes through twelve months post-injury (Kumar et al., The Journal of head trauma rehabilitation. 2015; 30(6):369-381). As the effect of sgp130 is inhibitory to the potent effects of sIL-6R on the activity of IL-6, sgp130 is a potential novel immunotherapy target for headaches and its associated post-injury outcomes.

This research has clinical and translational implications. For example, the present disclosure proposes a potential clinical decision tree in FIG. 69 based on the results of this study. If an individual does not report a headache in the first quarter, the present disclosure suggests that this individual would likely follow a trajectory similar to that of a member of the low TRAJ group, and can therefore follow usual care. An individual that reports a headache in the first quarter and has a sgp130:sIL-6R ratio equal to or above 5.9, the present disclosure suggests that this individual might resemble a member of the resolve TRAJ group and that their headaches taper off in subsequent months. Finally, an individual that reports a headache in the first quarter and has a sgp130:sIL-6R ratio below 5.9, the present disclosure suggests that this individual would likely resemble a member of the chronic TRAJ group and can therefore qualify for immunotherapy treatment. However, this decision tree is theoretical and these suggestions need to be tested.

Those with migraines and chronic headache are twice as likely to have comorbidities such as depression, anxiety, chronic pain, and are at higher risk for cardiovascular and respiratory events (Özge et al., Curr Pain Headache Rep. 2013; 17(12):382). The low sgp130:sIL-6R ratio and the presence of headaches in first three months after TBI are associated with several unfavorable outcomes. Specifically, the present disclosure found that an individual's membership in the chronic TRAJ group was associated with poorer outcomes after TBI. These individuals had worse reported percent back to normal measures, especially in the physical function area. Those with headaches in the first quarter (both the resolve and chronic TRAJ groups) had worse fatigue scores in those first three months, as measured by both the FSS and PROMIS questionnaires. Then in the third quarter, those in the chronic TRAJ group had higher cortisol levels, elevated levels of which exacerbate inflammation and are associated with more unfavorable outcomes and worse Glasgow Outcome Scores (Santarsieri et al., Brain Behav Immun. 2015; 45:15-27). In the third quarter, those in the chronic TRAJ group also had higher anxiety, which continued into the fourth quarter after injury, at which time the chronic TRAJ group also exhibited higher frequencies of post-traumatic depression. Certain studies have found that persistent IL-6 elevation can lead the individual with a TBI to experience worse outcomes (Kumar et al., Brain, Behavior, and Immunity. 2015; 45:253-262). The results of the present disclosure suggest that these unfavorable outcomes for the individuals in the chronic TRAJ group may have been due to the chronic lack of inhibition of IL-6 by low levels of sgp130 relative to sIL-6R during the first three months post-injury.

Certain studies have shown that TBI outcomes are associated with genetic variation (Hoh et al., Journal of Neurotrauma. 2010; 27(8):1413-1427; Weaver et al., Brain Imaging and Behavior. 2014; 8(3):420-434; Wagner et al., Brain Injury. 2012; 26(13-14):1658-1669; Failla et al., Neurorehabilitation and Neural Repair. 2015; 29(3):234-246). Genetic variations can potentially be associated with differences in pain responses after injury for these headache profiles. Additionally, headaches have long been associated with seizures; they are typical episodic neurological disorders and have some shared genetic mutations, such as the neuronal voltage-gated sodium channel SCN1A (Scheffer et al., Brain. 1997; 120 (Pt 3):479-490; Dichgans et al., The Lancet. 2005; 366(9483):371-377). Studying these associations longitudinally in a TBI population can elicit important relationships between these two post-injury outcomes.

The present disclosure provides a comprehensive, longitudinal characterization of headaches after TBI, and its comorbid impairments. The identification of a biological correlate of headaches after TBI has implications for the treatment and rehabilitation of individuals with TBI.

Example 9: Administration of Sgp130 to Human Subjects

Individuals with moderate to severe traumatic brain injuries (TBI) are more susceptible to secondary injury complications which are characterized by acute innate immune responses. These conditions, including headaches, cognitive impairment, seizures and depression, have led many in the field to characterize TBI as a chronic condition. Despite increasing knowledge regarding acute secondary injury mechanisms, less is known about the chronic phase and the mechanisms underlying these persistent impairments. The present disclosure has shown that pro-inflammatory mediators, including interleukin (IL) 6 in the sub-acute phase, as associated with worse global outcomes at 6 and 12 months (Kumar et al., J Head Trauma Rehabil. 2015; 30(6):369-381). A prolonged inflammatory response into the chronic phase post-injury may be detrimental to long-term recovery and may propagate some of these conditions over time post-TBI.

After injury, there are various signaling mechanisms that exist between inflammatory pathways which serve as activators of the hypothalamic-pituitary-adrenal (HPA) axis. IL-6 can stimulate HPA axis into a state of chronic stress with contributes to poor recovery after injury (Maes et al., Expert Opin. Ther. Targets 18, 495-512 (2014)). Cytokine receptors for IL-6 exist both in the membrane-bound form to a variety of tissue targets and in the soluble form. IL-6 binding to its membrane bound receptor is termed classical signaling (Rose-John et al., J Leukoc Biol. 2006; 80(2):227-236; Morieri et al., Mediators Inflamm. 2017; 2017: 1396398). Once IL-6 binds to its membrane bound receptor, a signaling complex is formed with membrane bound glycoprotein (gp130) (Morieri et al., Mediators Inflamm. 2017; 2017:1396398). This complex can have anti-inflammatory effects by controlling the innate immune response (Hoge et al., J Immunol. 2013; 190(2):703-711).

Conversely, certain studies also suggest IL-6 can bind to its soluble receptor (sIL-6R) and perpetuate the chronic inflammatory state through alternative trans-signaling (Rose-John et al., J Leukoc Biol. 2006; 80(2):227-236). The different mechanisms of soluble receptors versus membrane bound receptors stems from their ability to bind to different types of cells. The membrane bound receptors are active in hepatocytes and lymphocytes, however, soluble receptors can bind to any cell (Morieri et al., Mediators Inflamm. 2017; 2017:1396398). Soluble gp130 (sgp130) has inhibitory effects on the IL-6/IL-6R, which implies that sgp130 can attenuate trans-signaling induced IL-6 cascades (Rose-John et al., J Leukoc Biol. 2006; 80(2):227-236; Jostock et al., Eur J Biochem. 2001; 268(1):160-16). Furthermore, certain studies have shown a molar excess of sgp130 restricts the expression of the IL-6/sIL-6R (Jostock et al., Eur J Biochem. 2001; 268(1):160-16; Rose-John et al., Immunity. 2004; 20(1):2-4). In order to elucidate these effects on long-term outcome, more needs to be done to understand regulatory mechanisms of sgp130 to the IL-6 cytokine family.

There is growing importance in the relationships between neuroinflammation and the HPA axis. HPA axis dysregulation is demonstrated in several maladaptive central nervous system (CNS) outcomes such as anxiety, panic and bi-polar disorders (Abelson et al., Depress Anxiety. 2007; 24(1):66-76; Van Houdenhove et al., Med Hypotheses. 2009; 72(6): 701-705; Daban et al., Psychiatr Clin North Am. 2005; 28(2):469-480; Lenze et al., Am J Geriatr Psychiatry Off J Am Assoc Geriatr Psychiatry. 2011; 19(5):482-490). IL-6 signaling can stimulate the HPA axis and elevated levels of IL-6 and sIL-6R has been studied in cortisol-linked disorders such as depression and PTSD (Maes et al., Expert Opin Ther Targets. 2014; 18(5):495-512; Baker et al., Neuroimmunomodulation. 2001; 9(4):209-217). Sustained elevated cortisol levels and IL-6 signaling can lead to a disruption of gap junction proteins in the blood-brain-barrier (BBB), which may allow for an exchange of cytokines from the periphery to the CNS and vice versa, which is something that would not usually occur (Rochfort et al., Microvasc Res. 2015; 100:48-53). Chronic IL-6 signaling has a role in pathogenic roles involved in BBB disruption after injury (Burton et al., J Neuroinflammation. 2011; 8:54), and may indicate trans-signaling is occurring in the brain. However, the inflammatory state propagated by Il-6 has a dichotomous role in the body post-injury. IL-6 can help mediate septic shock, yet resolve acute inflammation, the former of which can have detrimental effects on recovery, particularly if inflammation is sustained into the chronic phase post-injury (Barton et al., *Infect Immun.* 1993; 61(4):1496-1499; Rose-John et al., *J Leukoc Biol.* 2006; 80(2):227-236).

IL-6 soluble receptor signaling can be a mechanism that hinders neuro-repair and prolongs inflammation in the first few months after TBI, which contributes to secondary conditions after TBI, and influences neuro-recovery.

The present disclosure suggests that sIL-6R is associated with various poor outcomes. Elevated sIL-6R levels are associated with poor secondary outcomes including post-traumatic headache (PTH) and overall cognitive impairment. Furthermore, in the context of post-traumatic depression (PTD), there are IL-6 signaling cascades to consider which may explain limited progress in the field at characterizing IL-6 pathophysiology implicated in depression. The results indicate that in the context of low sgp130 levels, depression is associated with higher IL-6 levels. The present disclosure demonstrated the IL-6 family cytokines (sIL-6R, agp130, IL-6 and sgp130:sIL6) are promising markers for predicting risk of multiple chronic secondary conditions, including PTH, PTD and cognitive impairments. Sgp130 levels are increased among those with PTE, suggesting that sgp130 may be higher as a compensatory response to help resolve seizure development or reduce epileptogenesis. The rodent data indicates sgp130 has a broad restorative impact on motor, anhedonia and cognitive performance as well as lymphocyte counts. FIG. 73 shows a drug development pipeline schematic for sgp130.

Clinical Administration Guidelines:
Participant Recruitment & Screening for Studies Study participants are recruited prospectively during their in-patient rehabilitation stay following TBI. Of note, women are not enrolled into initial feasibility study due to risk to fetus if pregnant, and due to potential risks to children being nursed and due to relatively low numbers of women with moderate to severe TBI relative to men. For initial feasibility studies, the goals are to identify a relatively homogenous group of likely responders for treatment; therefore, biological sex and age are restricted. Women are included in safety and efficacy studies and utilizes experience with this study to ensure a safe study design for including women and also older/younger adults.

Feasibility Study Inclusion: men, 25 to 50 years old, best GCS score≤12 during first 24 hours post admission, positive radiologic findings indicative of TBI, clinically screened as having functional capacity to participate in symptom assessment batteries, informed consent (via subject or appropriate proxy) received within two months of injury or end of rehabilitation stay (whichever occurs first), initial dose received 72 hours before discharge from rehabilitation. Study inclusion is prioritized to "likely responders", for feasibility studies. That is, patients having had acute care infection illness who are without signs/symptoms of active infection at the time of enrollment.

Safety and Efficacy Study Inclusion: men and women ages 18 to 75 are included if best GCS score<12 during first 24 hours post admission, positive radiologic findings indicative of TBI, clinically screened as having functional capacity to participate in symptom assessment batteries, informed consent (via subject or appropriate proxy) received within two months of injury. For safety and efficacy purposes, studies are conducted that include both women and men in a wider age group.

Exclusion: While siltuximab is not a selective drug, the present disclosure can mirror some of the inclusion/exclusion criteria based on certain previous work to evaluate its safety and efficacy. Certain studies that administer siltuximab exclude participation if the patient has had prior exposure to IL-6 or IL-6R targeted therapies (A Study to Evaluate the Efficacy and Safety of CNTO328 Plus Best Supportive Care in Multicentric Castleman's Disease—Tabular View—ClinicalTrials.gov; S0354, Anti-IL-6 Chimeric Monoclonal Antibody in Patients With Metastatic Prostate Cancer That Did Not Respond to Hormone Therapy—Tabular View—ClinicalTrials.gov; A Safety, Efficacy and Pharmacokinetic Study of Siltuximab (CNTO 328) in Participants With Solid Tumors—Full Text View—ClinicalTrials.gov). Furthermore, the most common adverse effects with siltuximab were rashes, pruritus, upper respiratory tract infection, increased weight and hypoeruricemia (Treatment with SYLVANT®. SYLVANT®. https://www-.sylvant.com/treatment). These are all factors to consider when testing a humanized recombinant sgp130 for administration in accordance with the present disclosure.

Feasibility Studies

The present disclosure proposes that by administering humanized recombinant sgp130 therapy to individuals with moderate-to-severe TBI, chronic inflammation would be reduced which, in turn, would result in better long-term outcomes and neuro-recovery.

Safety and Efficacy Studies:

The present disclosure uses endophenotype and symptoms data from feasibility studies to refine administration parameters for safety and efficacy studies. Combination therapy with other immunological targets may be useful in modulating treatment effects to minimize adverse symptoms and side effects as well as shape immune response to optimize therapeutic effects.

Primary/Secondary Outcome Measures:
Readouts for Intervention Feasibility:
  Numbers screened to make enrollment targets.
  Clinical and biological tolerance of recombinant sgp130.
  IL-6, sIL-6R, sgp130 and cortisol at enrollment and treatment.
  Routine measurements of absolute lymphocyte counts (ALC), absolute neutrophil counts (ANC), NLR.
  Post-enrollment and treatment infection rates.
  Hospital resource utilization metrics: hospital readmissions, Emergency Room Visits, relevant doctor appointments.
  Global health status (Glasgow outcome Scale) at 6 months post-injury, including mortality.
Readouts for Clinical Safety:
  Clinical and biological tolerance of sgp130.
  IL-6, sIL-6R, sgp130 and cortisol at enrollment and treatment and post-treatment.
  Inflammatory immune panel at enrollment, treatment, and post-treatment.
  Routine measurements of absolute lymphocyte counts (ALC), absolute neutrophil counts (ANC), NLR.
  Routine CBC, full metabolic and electrolyte panel.
  Global health status (Glasgow outcome Scale) at 6 and 12 months post-injury, including mortality.
  Post-enrollment and treatment infection rates.
  Hospital resource utilization metrics: hospital readmissions, Emergency Room Visits, relevant doctor appointments.
Behavioral/Clinical Readouts for Treatment Effectiveness:
  Global health status (Glasgow outcome Scale) at 6, 12 and 24 months post-injury, including mortality.
  PHH Incidence at 6, 12 and 24 months post-injury (for men) based on testosterone and Luteinizing hormone levels.
  Post-traumatic Headaches Incidence is assessed using a brief questionnaire over the months following treatment. It assesses whether headaches occur, where the pain is located, how severe the pain is, how long the headaches last and how frequently they occur.

Seizure Incidence is monitored using self-report methods and/or medical record abstractions.

Depression and Anxiety: 6 and 12 and 24 months post injury. The Patient Health Questionnaire (PHQ)-9, a validated screening tool for major depression, is used to assess presence and severity of depressive symptoms (Donders et al., *Arch Phys Med Rehabil.* 2017; 98(12): 2514-2519). Component questions include energy levels, concentration, and mood. The Generalized Anxiety Disorder (GAD)-7 is administered to screen for anxiety symptoms (Plummer et al., *Gen Hosp Psychiatry.* 2016; 39:24-31).

Fatigue: 6 and 12 and 24 months post injury. The Patient Reported Outcomes Measurement Information System (PROMIS) Fatigue scale is utilized at six-months post injury to assess fatigue symptoms affecting daily life activities and participation (Carlozzi et al., *Arch Phys Med Rehabil.* 2011; 92(10 Suppl):S52-60). Standardized T-scores are generated for analysis with a mean=50 and SD=10.

Neuropsychological Assessment: A Brief Test of Adult Cognition by Telephone (BTACT) is administered as a battery to characterize functioning of episodic memory, working memory, reasoning, verbal fluency, and executive function (Lachman et al., *Assessment.* 2014; 21(4): 404-417). Standardized T-scores are generated for analysis with a mean=50 and SD=10.

Behavioral Assessment: The Behavioral Assessment Screening Tool (BAST) is administered as a self-report composite measure of behavioral and emotional symptoms using validated individual assessments of cognitive control and emotional state (Juengst et al., *Disabil Rehabil.* 2019; 41(10):1200-1206).

Functional Outcome and Disability: Global recovery is assessed using the Glasgow Outcome Scale (GOS) scoring (Jennett et al., *Lancet Lond Engl.* 1975; 1(7905):480-484). The Disability Rating Scale (DRS) scoring system is used as a more granular assessment of recovery: 1) arousal & awareness, 2) cognitive ability for self-care, 3) physical dependence, 4) psychosocial adaptability for work, housework, or school (Rappaport et al., *Arch Phys Med Rehabil.* 1992; 73(7):628-634). TBI-Quality of Life (TBI-QOL) (Tulsky et al., *J Head Trauma Rehabil.* 2016; 31(1):40-51) and cognitive/motor scales of the Functional Independence Measure (FIM) (Tulsky et al., *J Head Trauma Rehabil.* 2016; 31(1):40-51) are assessed.

Quantifiable Biological Readouts for Treatment Effectiveness:

Consider serum as well as CNS derived exosomes for proteomic biomarkers.

IL-6, sIL6-R, sgp130 and cortisol: taken at enrollment and treatment and post treatment.

Inflammatory immune panel: taken at enrollment, treatment, and post-treatment that includes other soluble receptors, pro-inflammatory and anti-inflammatory markers etc.

Weekly cellular markers: measurements of absolute lymphocyte counts (ALC), absolute neutrophil counts (ANC), NLR.

Lymphocyte Cell type specific quantification: T-CD4+, T-CD8+.

Quantification of IL-6 receptor: soluble and membrane CD126 expression, genetic expression.

Quantification of circulating sgp130: during and post treatment.

Example 10: Treelet Methods Used Herein

Treelet transform (TT) is a statistical tool of dimension reduction (Gorst-Rasmussen et al., Stata Journal. 2012; 12(1):130-146; Gorst-Rasmussen et al., Am J Epidemiol. 2011; 173(10):1097-1104; Lee A B, Nadler B. Treelets—A Tool for Dimensionality Reduction and Multi-Scale Analysis of Unstructured Data). TT can be applied to structure high-dimensional data (i.e. data with a high number of variables) with variable redundancy (i.e. where a large number of variables can be represented by a smaller subset). By conducting principal components analysis (PCA) in a hierarchical clustering framework, TT produces clusters of variables, which can be summarized using a treelet cluster score to represent cluster membership. In the TT tree, the two most strongly correlated variables join, and a local PCA is conducted to derive a sum score for these two variables. This process is repeated until all components have joined into a single "branch". A cut-level is then determined using cross-validation to determine meaningful clusters. Treelet is said to produce clusters that reflect the underlying structure of the data as a whole.

TT can be performed using STATA and R statistical software. Inclusion in TT analysis requires complete data for all variables (or components) and that data be stored. TT requires the specification of 1) the number of clusters and 2) a cut-level at which components significantly cluster. Deriving the number of clusters is a data-driven process, dependent both upon the number of components contained in a cluster (preferred ≥2 components in a cluster) and the sparsity of data desired. For a given number of clusters, a K-fold cross-validation process identifies the optimal cut-point that maximizes the variance explained by the TT clusters while reducing variables into a meaningfully sparse number of components. TT generates a dendrogram as a visual representation of the hierarchical joining of the input variables.

TT was performed in a group of 159 individuals with moderate-to-severe-TBI to identify five clinically/biologically meaningful clusters of inflammatory markers (n=31). The present disclosure identified that inflammation markers generally cluster in unique patterns that likely represent five arms of immunity. Treelet cluster scores represent levels of inflammatory markers for a given cluster, acting as a general quantitative measurement of unique immune function within each cluster. These clusters represent the overall state of inflammatory arms of adaptive immunity, innate immunity, allergy immunity, soluble receptors, and chemokines. Further, they represent a novel approach to identifying inflammatory markers that vary as a function of sTNFR1 TRAJ group membership and IL-7 TRAJ group membership.

This methodology was applied in the context of grouping international classification of disease codes for purposes of outcome assessment in a TBI population (Kumar et al., J Head Trauma Rehabil. 2018; 33(1):15-24, the content of which is incorporated by reference in its entirety).

Example 11: Group Based Trajectory Methods Used Herein

Group-based trajectory modelling (GBTM or TRAJ) is a statistical methodology that can be used to analyze the evolution of a measure over time among groups of individuals, identifying distinct longitudinal groups. GBTM requires determining 1) distribution of the input data, 2) number of distinct groups (or trajectories) that may exist in the data, and 3) the polynomial order of each trajectory. An exemplary group-based trajectory modeling is disclosed in Nagin et al., Ann Nutr Metab. 2014; 65(2-3):205-210, and the content of which is incorporated by reference herein in its entirety.

The SAS procedure PROC TRAJ and the Stata add-on Traj are able to conduct GTBM. GBTM does not require complete observations for an individual at all time-points. In certain embodiments, at least two longitudinal data points are collected for a participant's inclusion in biomarker GBTM. GBTM can be applied to continuous, categorical, or dichotomous variables by specifying the distribution as censored normal, zero-inflated Poisson, or Bernoulli distribution respectively. To begin GBTM, fit a one group model to a quartic polynomial order. Additional groups of the quartic polynomial order are then added. The Bayes factor is used to assess improved performance across two GBTM models, comparing the BIC of each model using the equation $e^{BIC1-BIC2}$. A higher BIC value is preferred, with a Bayes factor ≥10 is generally considered a meaningful difference between two models. A combination of BIC & Bayes factor model fit diagnostics with clinical/content expertise should be used to identify the number of groups. After determining the number of groups, the polynomials of each group should be lowered, until the highest order polynomial for each group is significant (typically $\alpha=0.05$). Once groups have been fit to the appropriate polynomial, average poster probabilities (APP's) are generated for each group as the APP for group membership, ranging from 0 to 1 with higher values indicating better model fit. Values greater than 0.7 are recommended for each groups APP.

Exemplary applications of GBTM are disclosed in Kumar et al., Brain Behav Immun. 2015; 45:253-262; Munoz et al., Front Mol Neurosci. 2017; 10:44; Santarsieri et al., Brain Behav Immun. 2015; 45:15-27; Wagner et al., J Neurotrauma. 2011; 28(6):871-888; and Niyonkuru et al., J Neurotrauma. 2013; 30(11):938-945, and the contents of which are incorporated herein by references.

The present disclosure discloses GBTM identified unique pairs of trajectories of sgp130, sIL6R, and a ratio of sgp130: sIL6R. Each pair of trajectories feature generally linear (zero-order) longitudinal trajectories, with a "high" trajectory group (consistently above levels in uninjured controls) and a "low" trajectory group (consistently below or equal to uninjured controls). TRAJ groups were used for certain analyses in outcome estimation, patient stratification, cut points, anticipated treatment effects and risk reduction etc.

The present disclosure applied TRAJ group analyses for SGP130 and sIL-6R as novel method of stratifying patients for potential treatment, assessing risk for TBI related impairments and as a group selection strategy for graphing other inflammatory markers (e.g. chemokines, soluble receptors etc.) that vary as a function of treatment.

Example 12: Biomarkers Gauging Likely Responders & Treatment Effectiveness (IL-6) GOS Neurorecovery Regression Model The Glasgow Outcome Scale (GOS) is a widely utilized tool that classifies outcome into five categories: 5=good recovery; 4=moderate disability; 3=severe disability; 2=persistent vegetative state; and 1=death. Among survivors, patients are often grouped GOS 2/3 vs. GOS group 4/5. GOS and extended GOS represents global capacities and impairments in the areas of cognition, behavior, mood, fatigue, sleep and other impairments that contribute to overall neurorecovery. GOS and extended GOS are primary variables for most acute care clinical trials to date, none of which have successfully shown to have broad efficacy value.

The present disclosure created an GOS neurorecovery regression model to identify biomarkers that can gauge likely responders and the effectiveness of treatment (N=129, AUC=0.651). The variables and their ORs and p-values for the model are shown in FIG. 70B. IL-6-sIL6R interaction graph (FIG. 70A) illustrates the relationship between IL-6-sIL6R complex signaling and universal outcome post-TBI. Individuals with high IL-6 and sIL6R levels experienced greatest odds for poor outcome. It supports that elevated IL-6-sIL6R complex formation and trans-signaling in patients with poor outcome.

The direction of the relationship from IL-6 to GOS switched at 22.714 ng/mL of sIL6R. When sIL6R level was lower than 22.714 ng/mL, the level of IL-6 was positively associated with an improved recovery. When sIL6R level was higher than 22.714 ng/mL, the level of IL-6 was positively associated with a poor recovery.

Various publications are cited herein, the contents of which are hereby incorporated by reference in their entireties.

Although the presently disclosed subject matter and its advantages have been described in detail, it should be understood that various changes, substitutions and alterations can be made herein without departing from the spirit and scope of the present disclosure. Moreover, the scope of the present application is not intended to be limited to the particular embodiments of the process, machine, manufacture, and composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods, or steps.

Various patents, patent applications, publications, product descriptions, protocols, and sequence accession numbers are cited throughout this application, the presently disclosed subject matter of which are incorporated herein by reference in their entireties for all purposes.

What is claimed is:

1. A method of treating a traumatic brain injury (TBI), or treating or reducing the risk of a TBI-associated impairment in a subject in need thereof, comprising administering to the subject a sgp130, wherein the TBI-associated impairment is selected from the group consisting of posttraumatic headache (PTH), posttraumatic depression (PTD), cognitive deficits, posttraumatic epilepsy (PTE), seizure, anxiety, depression, fatigue, insomnia and combinations thereof.

2. The method of claim 1, wherein the method improves outcome of TBI in the subject as measured by a Glasgow Outcome Scale (GOS) score.

3. The method of claim 2, wherein the method reduces long-term disability in the subject.

4. The method of claim 1, wherein the method reduces sIL-6R mediated trans-signaling in the subject.

5. The method of claim 1, wherein the sgp130 comprises a sgp130/Fc dimer.

* * * * *